(12) United States Patent
Sun

(10) Patent No.: US 11,466,300 B2
(45) Date of Patent: Oct. 11, 2022

(54) METHOD FOR PRODUCING N-ACETYL-D-GLUCOSAMINE AND/OR D-GLUCOSAMINE SALT BY MICROBIAL FERMENTATION

(71) Applicant: Lan Sun, Nanjing (CN)

(72) Inventor: Lan Sun, Nanjing (CN)

( * ) Notice: Subject to any disclaimer, the term of this patent is extended or adjusted under 35 U.S.C. 154(b) by 326 days.

(21) Appl. No.: 16/091,865

(22) PCT Filed: Apr. 14, 2017

(86) PCT No.: PCT/CN2017/080653
§ 371 (c)(1),
(2) Date: Oct. 5, 2018

(87) PCT Pub. No.: WO2017/174040
PCT Pub. Date: Dec. 10, 2017

(65) Prior Publication Data
US 2020/0308615 A1    Oct. 1, 2020

(30) Foreign Application Priority Data

Apr. 5, 2016  (CN) .......................... 201610208203.9
Apr. 5, 2017  (CN) .......................... 201710217604.5

(51) Int. Cl.
| | |
|---|---|
| *C07K 14/195* | (2006.01) |
| *C12P 19/26* | (2006.01) |
| *C12N 9/10* | (2006.01) |
| *C12N 9/12* | (2006.01) |
| *C12N 9/80* | (2006.01) |
| *C12N 9/90* | (2006.01) |
| *C12N 15/70* | (2006.01) |
| *C12N 9/78* | (2006.01) |
| *C12N 9/88* | (2006.01) |
| *C12P 19/02* | (2006.01) |
| *C12N 1/20* | (2006.01) |
| *C12R 1/19* | (2006.01) |

(52) U.S. Cl.
CPC ............ *C12P 19/26* (2013.01); *C12N 9/1029* (2013.01); *C12N 9/1205* (2013.01); *C12N 9/78* (2013.01); *C12N 9/80* (2013.01); *C12N 9/88* (2013.01); *C12N 9/90* (2013.01); *C12N 15/70* (2013.01); *C12P 19/02* (2013.01); *C12Y 203/01157* (2013.01); *C12Y 207/0106* (2013.01); *C12Y 305/01025* (2013.01); *C12Y 305/99006* (2013.01); *C12Y 401/03003* (2013.01); *C12Y 501/03009* (2013.01); *C12Y 501/03014* (2013.01); *C12Y 504/02001* (2013.01); *C12Y 504/0201* (2013.01); *C12N 1/205* (2021.05); *C12R 2001/19* (2021.05)

(58) Field of Classification Search
CPC .. C12P 19/26; C12P 19/02; C12Y 305/99006; C12Y 401/03003; C12Y 501/03009; C12Y 207/0106; C12Y 305/01025; C12Y 501/03014; C12Y 206/01016; C12N 9/1029; C12N 9/78; C12N 15/70; C12N 1/205; C12R 2001/19; C07K 14/195
See application file for complete search history.

(56) References Cited

U.S. PATENT DOCUMENTS

| | | | |
|---|---|---|---|
| 6,372,457 B1 | 4/2002 | Berry et al. | |
| 7,332,304 B2 * | 2/2008 | Deng | .................... C12N 15/52 435/15 |

FOREIGN PATENT DOCUMENTS

| | | |
|---|---|---|
| CN | 104059872 A | 9/2014 |
| CN | 104293724 A | 1/2015 |
| WO | 2004003175 A2 | 1/2004 |

OTHER PUBLICATIONS

International Search Report dated Jun. 28, 2017 from corresponding PCT Application No. PCT/CN2017/080653.

* cited by examiner

*Primary Examiner* — Lynn Y Fan

(74) *Attorney, Agent, or Firm* — Grogan, Tuccillo & Vanderleeden, LLP

(57) ABSTRACT

This Invention discloses a method for production of N-Acetyl-D-Glucosamine and/or D-Glucosamine Salt by microbial fermentation. The method is intended to manufacture N-Acetyl-D-Glucosamine and/or D-Glucosamine Salt in higher efficiency and higher yield, by increasing the effects of N-Acetyl-D-Mannosamine Kinase.

12 Claims, 1 Drawing Sheet
Specification includes a Sequence Listing.

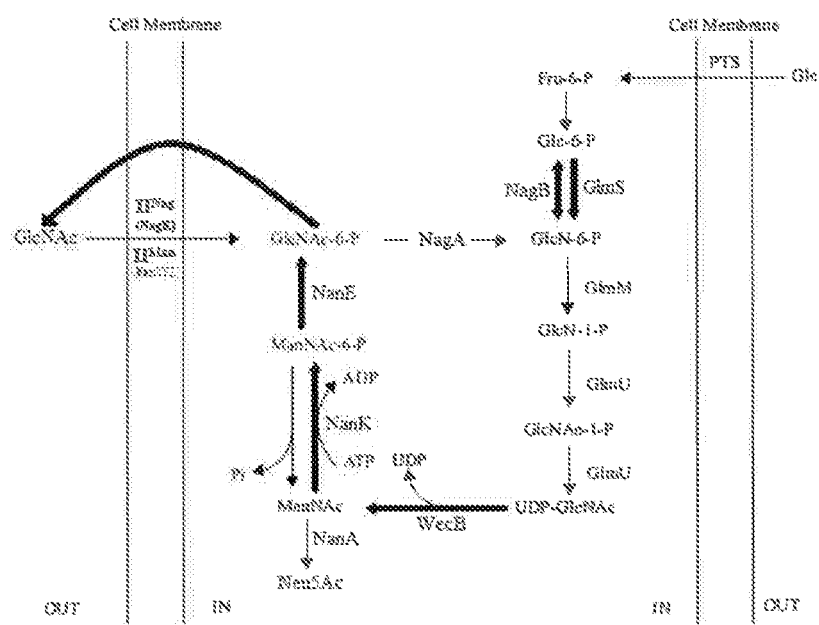

US 11,466,300 B2

METHOD FOR PRODUCING N-ACETYL-D-GLUCOSAMINE AND/OR D-GLUCOSAMINE SALT BY MICROBIAL FERMENTATION

CROSS REFERENCE TO RELATED APPLICATIONS

This is a national stage application under 35 U.S.C. § 371 (c) of prior-filed, co-pending, PCT application serial number PCT/CN2017/080653, filed on Apr. 14, 2017, which claims priority to Chinese patent application number 201610208203.9, filed Apr. 5, 2016, and Chinese patent application number 201710217604.5, filed Apr. 5, 2017, the entire contents of which are incorporated herein in their entireties.

SEQUENCE LISTING

The instant application contains a sequence listing which has been submitted in ASCII format via EFS-web and is hereby incorporated by reference in its entirety. Said ASCII copy, created on May 30 2020 is 45 KB in size.

FIELD OF TECHNOLOGY

This invention belongs to the field of microbial fermentation. Specifically, this invention relates with production of N-Acetyl-D-Glucosamine by microbial fermentation, and further preparation method of D-Glucosamine Salt.

BACKGROUND TECHNOLOGY

N-Acetyl-D-Glucosamine (NAG or GlcNAc), also called N-Acetyl-Glucosamine or N-AcetylGlucosamine, is a basic constituent unit for multiple important polysaccharides in biological cells, and has an important physiological function in organisms. N-Acetyl-D-Glucosamine may be used clinically to: Increase the function of human immune system; inhibit growth of malignancy or fibrocytes; treatment effectively various inflammations; and be as a low-heat sweetener in diabetic patients, and a food additive for infants and young children; and so on. Hydrolysis of N-Acetyl-D-Glucosamine may be used to produce D-Glucosamine Hydrochloride, which may be used as a food additive for fighting and preventing cancer, and lowering blood lipids and blood pressure, and is presently a third-generation food additive with healthcare function in chitin health food series. Moreover, N-Acetyl-D-Glucosamine is a major raw material for synthesis of Chlorozotocin, a anticancer agent; as a biochemical reagent, it may also be used as an immune adjuvant for resisting bacterial infection, and an activating agent for counteracting influenza viruses in human body.

Now all over the world, a lot of patients suffer from, arthritis pain to different extents. In the United States only, there are 33 millions of patients suffering from arthritis and arthralgia; in our country, more than more than 0.15 billions of patients suffering arthritis and arthralgia. As D-Glucosamine products have special therapeutic and healthcare effects against arthritis and arthralgia, it has been used extensively, and now has become a very important raw material in domestic and foreign markets.

It is believed that N-Acetyl-D-Glucosamine has similar effects to D-Glucosamine. It is know that intake of N-Acetyl-D-Glucosamine can induce production of new cartilage and block episodes of osteoarthritis, or is used to treat osteoarthritis in some cases. As D-Glucosamine is bitter while N-acetyl-D-Glucosamine is 50% sweet of sucrose and is easily ingested. Therefore, N-acetyl-D-Glucosamine has aroused concern as alternative of D-Glucosamine.

Presently, Glucosamine is mainly derived from biological extract at home and abroad. Biological extraction is mainly to extract chitin or chitosan from shrimp and crab shells and then hydrolyzed by concentrated hydrochloric acid, or extract from citrate slags by acid or alkali. The annual output is approximately 20,000 tons. However, when extracted from shrimp and crab shells, each ton of the product is accompanied with a great amount of waste residue, and more than 100 tons of waste water; when extracted from citrate residue, each ton of the product is accompanied with 30-50 tons of waste acid residue—the process is a high-pollution process and has been prohibited in many places. Moreover, Glucosamine extracted from aquatic shells is not suitable for patients sensitive to aquatic products in whom it may result in severe allergy problems or even life-threatening. Besides, the biological extraction and purification processes are complicated, and the product smells fishy and is unstable. Moreover, due to environmental pollution, it is inevitable that Glucosamine extracted from shrimp and crab shells may be contaminated by heavy metals.

Therefore, Glucosamine produced by biological extraction method cannot meet the needs of people in quantity and quality; it has to develop a new alternative method. If it is produced by chemical synthesis method, there are the following three shortcomings: High production cost; severe environmental pollution; and potential safety risks. Now the method has been cancelled at home and abroad. In comparison, the microbial fermentation method for production of Glucosamine is a good route, in which, glucose and inorganic salts are as raw materials, and undergo liquid fermentation by excellent strains, and separation, concentration, and purification to directly product Glucosamine. No noxious gas is produced during production. Glucosamine produced by fermentation method does not smell fishy, and the production resources are not limited. As well, strain improvement is carried out by metabolic engineering, with high output, and great potential for large-scale industrial production. Therefore, the microbial fermentation method for production of Glucosamine has a significant revolution to replace conventional biological extraction, and has an advantage in the cost and make a contribution to environmental protection in reducing pollution of three wastes.

The routine methods of microbial fermentation for production of N-Acetyl-D-Glucosamine include: Method (for example, U.S. Pat. No. 5,998,173, "Process for producing N-acetyl-D-glucosamine") to produce N-Acetyl-D-Glucosamine from chitin manufactured from shrimp shells by enzymatic degradation; the enzymes are produced microbially; Method (for example, US20030073666A1, "N-acetyl-D-glucosamine and process for production of N-acetyl-D-glucosamine") to produce N-Acetyl-D-Glucosamine from chitin manufactured and purified from fungal residue (such as fungal residue of *Aspergillus niger*, used by citrate fermentation) by enzymatic degradation or acid-partial hydrolysis; the enzymes are produced microbially (by *Trichoderma*); method (for example, US20110059489A1, "Method for fermentative production of N-acetyl-D-glucosamine by microorganism") to produce N-Acetyl-D-Glucosamine by fermentation of *Trichoderma*, using directly glucose as carbon source, other than chitin and chitosan oligosaccharide produced from fungal residue or shrimp shells; method (for example, JP2004283144A, "Method for producing glucosamine and N-acetylglucosamine") to produce N-Acetyl-D-Glucosamine from incubation of Chlorella cells infected with *Chlorovirus*, or of recombinant *Escherichia coli* introduced with the gene of *Chlorovirus*; method (for example, U.S. Pat. No. 6,372,457, "Process and materials for production of glucosamine"; WO2004/003175, "Process and materials for production of glucosamine and N-acetylglucosamine") to produce D-Glucosamine or N-Acetyl-D-Glucosamine by fermentation, using genetically modified microorganism, particularly genetically modified *Escherichia coli*.

The method for production of N-acetyl-D-glucosamine from degradation of chitin derived from the shells of shellfish such as crab and shrimp, by microorganism or by enzymes produced microbially, is relatively conventional, and has the problems of low yield, high cost, and insufficient animal source, etc. The method for production of N-acetyl-D-glucosamine from incubation of chlorella cells infected with *Chlorovirus* is of complicated operation, etc., as it is involved with the step of crushing cells to obtain N-acetyl-D-glucosamine. The method for production of N-acetyl-D-glucosamine by *Trichoderma*, using glucose as carbon source, had the advantages of requiring no chitin or chitin oligosaccharide as carbon source, produced from the shells of shellfish or from fungi dregs. However, as the fungi such as *Trichoderma* are of low fermentation temperature (27° C.), long term (10 days), and relatively low yield (15 mg/mL), and thus are of long production cycle, high cost, and easy contamination, seriously restricting industrial application of the method.

Clearly, aiming at the increasing market demand for Glucosamine, the method to produce N-Acetyl-D-Glucosamine by genetically modified microorganism is an important method with application potential to realize large-scale industrialization. New, genetically modified microorganism may be obtained by multiple modes, such as gene recombination, gene transfer, gene mutation, gene deletion, gene overexpression, or change to metabolic pathway, etc.

U.S. Pat. No. 6,372,457, a United State patent, discloses the method and materials to produce D-Glucosamine by microbial fermentation. This Invention is involved with genetically modified microorganism for the method for production Glucosamine, as well as recombinant nucleic acid molecules, and proteins produced by the said recombinant nucleic acid molecules. The said genetically modified microorganism in this Invention are mainly involved with the genetic modification increasing the activities of Glucosamine-6-Phosphate Synthase, including multiple gene mutations or amino acid deletion and substitution. However, the patient is not involved with changes of Glucosamine-6-Phosphate Synthase gene promoter replacement or deletion, leading to decreased or increased activities of Glucosamine-6-Phosphate Synthase. Moreover, the patient is mainly intended to produce D-Glucosamine, the only one target product, by genetic modification of Glucosamine-6-Phosphate Synthase, and is not involved with production of N-Acetyl-D-Glucosamine. Furthermore, as D-Glucosamine is quite unstable in fermentation broth, degradation products may be possibly toxic to microorganism. This production mode of D-Glucosamine by genetic modification is of very low yield, and is restricted in practical application.

The biosynthetic method for production of D-Glucosamine and N-Acetyl-D-Glucosamine is disclosed in WO2004/003175. The method is to produce Glucosamine and/or N-Acetyl-D-Glucosamine by fermentation of genetically modified microorganism. This Invention also discloses the genetically modified microorganism for production of Glucosamine and N-Acetyl-D-Glucosamine. Additionally, this Invention also describes the recovery method of N-Acetyl-D-Glucosamine produced by fermentation method, including method for production of high-purity N-Acetyl-D-Glucosamine. This Invention also discloses the method for production of D-Glucosamine from N-Acetyl-D-Glucosamine. The said genetically modified microorganism in this Invention are mainly involved with the genetic modification increasing the activities of Glucosamine-6-Phosphate Acetyltransferase. The expression of yeast Glucosamine-6-Phosphate Acetyltransferase gene (GNA1) in *Escherichia coli* may acetylate Glucosamine-6-Phosphate into Acetylglucosamine-6-Phosphate, which has been reported and demonstrated in previous literatures (Mio T1, Yamada-Okabe T, Arisawa M, Yamada-Okabe H: *Saccharomyces cerevisiae* GNA1, an essential gene encoding a novel acetyltransferase involved in UDP-N-acetylglucosamine synthesis, *J Biol Chem.*, 1999 Jan. 1; 274(1):424-9).

CONTENTS OF THE INVENTION

Aiming at the metabolic pathway of N-Acetyl-D-Glucosamine, this Invention uses a new genetic modification method to transform microorganism, and utilizes such microorganism to produce more efficiently N-Acetyl-D-Glucosamine (GlcNAc) and/or D-Glucosamine Salt in higher yield.

Specifically speaking, by increasing the effects of N-Acetyl-D-Mannosamine Kinase (NanK), this Invention may strengthen phosphorylation of N-Acetyl-D-Mannosamine (ManNAc) in microorganism into N-Acetyl-D-Mannosamine-6-Phosphate (ManNAc-6-P), so that microorganism may produce more efficiently N-Acetyl-D-Glucosamine (GlcNAc) and/or D-Glucosamine in a higher yield.

On top of the above contents, this Invention is further involved with one or more of the following contents:

1. By increasing the effects of N-Acetyl-D-Mannosamine-6-Phosphate Epimerase (NanE) in microorganism, strengthen transformation of N-Acetyl-D-Mannosamine-6-Phosphate (ManNAc-6-P) in microorganism into N-Acetyl-D-Glucosamine-6-Phosphate (GlcNAc-6-P), excreted into extracellular domain to become N-Acetyl-D-Glucosamine (GlcNAc), so that microorganism may produce more efficiently N-Acetyl-D-Glucosamine (GlcNAc) and/or D-Glucosamine Salt in a higher yield.

2. By increasing the effects of D-Glucosamine-6-Phosphate Deaminase (NagB) in microorganism, and meanwhile decreasing preferably the effects of Glucosamine-6-Phosphate Synthase (GlmS, also called L-Glutamine-D-fructose-6-Phosphate Aminotransferase), strengthen amination of Glucose-6-Phosphate (Glc-6-P) in microorganism to D-Glucosamine-6-Phosphate (GlcN-6-P). The reaction catalyzed by D-Glucosamine-6-Phosphate Deaminase (NagB) is reversible, while that catalyzed by Glucosamine-6-Phosphate Synthase (GlmS) is irreversible, but has a severe problem for product inhibition. When the NagS-catalyzed reaction proceeds in the direction from Glc-6-P to produce GlcN-6-P, its function is the same as that of GlmS, and may replace GlmS, without any problem for product inhibition. Increase effects of NagS, accelerate the NagS-catalyzed reaction to proceed in the direction from Glc-6-P to GlcN-6-P, meanwhile decrease preferably the effects of GlmS, mitigate the product inhibition problem of GlmS, to achieve the purpose of increasing GlcN-6-P, so that such microorganism may produce more efficiently N-Acetyl-D-Glucosamine (GlcNAc) and/or D-Glucosamine Salt in a higher yield.

3. By increasing the effects of Glucosamine-6-Phosphate Synthase (GlmS, also called L-Glutamine-D-Fructose-6-Phosphate Aminotransferase) in microorganism, and meanwhile decreasing the effects of D-Glucosamine-6-Phosphate Deaminase (NagS), strengthen amination of Glucose-6-Phosphate (Glc-6-P) in microorganism to D-Glucosamine-6-Phosphate (GlcN-6-P). The reaction catalyzed by D-Glucosamine-6-Phosphate Deaminase (NagS) is reversible. When the NagS-catalyzed reaction proceeds in the direction from Glc-6-P to GlcN-6-P, its function is opposite to that of GlmS, and may offset the effects of GlmS. Decreasing the effects of NagS, block the NagS-catalyzed reaction to proceed in the direction from GlcN-6-P of Glc-6-P, and meanwhile overexpress GlmS, accelerate GlmS-catalyzed amination of Glc-6-P to GlcN-6-P, to achieve the purpose of increasing GlcN-6-P, so that microorganism may produce more efficiently N-Acetyl-D-Glucosamine (GlcNAc) and/or D-Glucosamine Salt in a higher yield.

4. By increasing the effects of UDP-N-Acetyl-D-Glucosamine-2-Epimerase (WecB), strengthen transformation of UDP-N-Acetyl-D-Glucosamine (UDP-GlcNAc) in microorganism into N-Acetyl-D-Mannosamine (ManNAc), so that microorganism may produce more efficiently N-Acetyl-D-Glucosamine (GlcNAc) and/or D-Glucosamine Salt in a higher yield.

5. By reducing the effect of an enzyme or protein in the microorganism associated with the re-intake of the target product into the cell or the degradation of the beneficial intermediate, and increasing the sugar conversion rate and the N-acetyl-D-glucosamine production in the microorganism, thereby allowing the microorganism to produce N-acetyl-D-glucosamine (GlcNAc) and/or D-glucosamine salts with higher efficiency and higher yields. This includes but not limited to one or more of the following:

(1) Decreasing the effect of mannose transporter EIIM, P/IIIman (Mannose transporter EIIM, P/IIIMan, ManXYZ) in microorganisms to prevent hexose transport such as N-acetyl-D-glucosamine (GlcNAc) from being transported back into the cell for degradation.

(2) Reducing the effect of N-acetylneuraminic acid lyase (NanA) in microorganisms to prevent degradation of N-acetyl-D-mannosamine (ManNAc) in microorganisms.

(3) Reducing the effect of N-acetyl-glucosamine-6-phosphate deacetylase (NagA) in microorganisms to prevent the conversion of N-acetyl-D-glucosamine-6-phosphate (GlcNAc-6-P) in microorganisms to D-glucosamine-6-phosphate (GlcN-6-P).

(4) Reducing the effect of N-acetyl-D-glucosamine specific enzyme IINag (NagE) in microorganisms to prevent N-acetyl-D-glucosamine (GlcNAc) from being transported into the cells for degradation.

(5) Enhancing the effect of phosphoglucosamine mutase (GlmM) in microorganisms to increase the conversion of D-glucosamine-6-phosphate (GlcN-6-P) to D-glucosamine-1-phosphate (GlcN-1-P).

(6) Increasing the effect of bifunctional enzyme N-acetyl-D-glucosamine-1-phosphate uridine transferase (bifunctional N-acetyl glucosamine-1-phosphate uridyltransferase/glucosamine-1-phosphate acetyl transferase, GlmU) to increase the conversion of D-glucosamine-1-phosphate (GlcN-1-P) in microorganisms to N-acetyl-D-glucosamine-1-phosphate (GlcNAc-1-P), and the further conversion to UDP-N-acetyl-D-glucosamine (UDP-GlcNAc).

Based on one implementation scheme of this Invention, this Invention is involved with the method for production of N-Acetyl-D-Glucosamine (GlcNAc) and/or D-Glucosamine Salt by microbial fermentation, which includes:

A) Cultivating a microorganism in a fermentation medium, said microorganism contains at least one genetic modification that may increase the effects of N-Acetyl-D-Mannosamine Kinase (NanK) in microorganism; and B) Collecting of N-Acetyl-D-Glucosamine (GlcNAc) produced in the cultivation step A).

Preferably further include C) Deacetylation of N-Acetyl-D-Glucosamine (GlcNAc) to produce D-Glucosamine Salt.

In this Invention, the genetic modification to increase the effects of N-Acetyl-D-Mannosamine Kinase (NanK) in microorganism are selected from: a) increased effects of N-Acetyl-D-Mannosamine Kinase (NanK) in microorganism; and/or b) overexpression of N-Acetyl-D-Mannosamine Kinase (NanK) in microorganism.

A technician in this field may understand that, to increase the effects of N-Acetyl-D-Mannosamine Kinase (NanK) in microorganism, it may be realized by screening for a gene mutant encoding N-Acetyl-D-Mannosamine Kinase (NanK) with increased activities. The screening for a NanK gene mutant may be achieved by error-prone PCR technology to produce a high-frequency mutant gene. To increase the effects of N-Acetyl-D-Mannosamine Kinase (NanK) in microorganism, it may also be realized by increasing its gene copies or replacing it with a promoter with a higher expression level than that of the natural promoter, for overexpression of N-Acetyl-D-Mannosamine Kinase (NanK). In a specific implementation scheme, the microorganism are transformed by molecules of at least recombinant nucleic acid, containing at least one genetic modification that may increase the effects of N-Acetyl-D-Mannosamine Kinase (NanK) in microorganism.

In a preferably optimized implementation scheme, the microorganism is transformed with at least one recombinant nucleic acid molecule comprising a nucleic acid sequence encoding N-Acetyl-D-Mannosamine Kinase (NanK).

On the other hand, the nucleic sequence encoding N-Acetyl-D-Mannosamine Kinase (NanK) contains at least one genetic modification that may increase the activities of N-Acetyl-D-Mannosamine Kinase (NanK). Preferably the said genetic modification contains one or more substitutions at the following corresponding sites of SEQ ID NO: 17: Substitution of glutamine at site 36 by arginine, substitution of isoleucine at Site 103 by methionine, and substitution of arginine at Site 223 by serine. More preferably, the nucleic acid sequence encoding the said N-Acetyl-D-Mannosamine Kinase (NanK) is SEQ ID NO: 26; the amino acid sequence of the said N-Acetyl-D-Mannosamine Kinase (NanK) is SEQ ID NO: 27.

On the other hand, at least approximately 30% (more preferably at least approximately 50%, further more preferably at least approximately 70%, further more preferably at least approximately 80%, and further more at least approximately 90%, and most preferably at least approximately 95%) of the amino acid sequence of the said N-Acetyl-D-Mannosamine Kinase (NanK) is the same as that of SEQ ID NO: 17, where the said N-Acetyl-D-Mannosamine Kinase (NanK) is active.

On the other hand, the said N-Acetyl-D-Mannosamine Kinase (NanK) has the amino acid sequence of SEQ ID NO: 17.

On the other hand, the gene copies in the recombinant nucleic acid molecules, encoding N-Acetyl-D-Mannosamine Kinase (NanK), are increased.

On the other hand, the recombinant nucleic acid molecules contain an endogenous promoter, with a higher expression level of promoters, enhancers, and fusion sequences, etc., than those of natural endogenous promoters. Preferably, the recombinant nucleic acid molecules contains a higher expression level of promoters than that of natural endogenous promoters, such as HCE promoter, gap promoter, trc promoter, and T7 promoter, etc.; more preferably, the recombinant nucleic acid molecules contain trc promoter. trc promoter is a combined promoter of trp promoter and lac promoter, with a higher transcription efficiency than that of trp, and with strong promoter characteristics to be regulated by lad repressor protein.

In this Invention, microorganism transformed by recombinant nucleic acid molecules transform are selected from free type (that is to say, recombinant nucleic acid molecules are mounted into plasmids) and integrated type (that is to say, recombinant nucleic acid molecules are integrated into the genomes of microorganism). Preferably, recombinant nucleic acid molecules are integrated into the genomes of microorganism.

In another preferably optimized implementation scheme, the microorganism contain at least one genetic modification of the natural endogenous promoter to the gene encoding N-Acetyl-D-Mannosamine Kinase (NanK). Preferably, the natural endogenous promoter with the gene encoding N-Acetyl-D-Mannosamine Kinase (NanK) is replaced by a promoter with a higher expression level, such as HCE promoter, gap promoter, trc promoter, or T7 promoter, etc.; more preferably, the natural endogenous promoter with the gene encoding N-Acetyl-D-Mannosamine Kinase (NanK) is replaced by trc promoter.

Based on the preferably optimized implementation scheme, the said microorganism contains one or more of the following genetic modifications:

(1) Contain at least one genetic modification that may increase the effects of N-Acetyl-D-Mannosamine-6-Phosphate Epimerase (NanE) in microorganism;

(2) Contain at least one genetic modification that may increase the effects of D-Glucosamine-6-Phosphate Deaminase (NagB) in microorganism, and preferably contain at least one genetic modification that may decrease the effects of Glucosamine-6-Phosphate Synthase (GlmS);

(3) Contain at least one genetic modification that may increase the effects of D-Glucosamine-6-Phosphate Synthase (GlmS) in microorganism, and preferably contain at lest one genetic modification that may decrease the effects of D-Glucosamine-6-Phosphate Deaminase (NagB)

(4) Contain at least one genetic modification that may increase the effects of UDP-N-Acetyl-D-Glucosamine-2-Epimerase (WecB) in microorganism;

In respect to the above (1), the genetic modification increasing the effects of N-Acetyl-D-Mannosamine-6-Phosphate Epimerase (NanE) in microorganism is selected from a) increasing the effects of N-Acetyl-D-Mannosamine-6-Phosphate Epimerase (NanE) in microorganism; and/or b) overexpression of N-Acetyl-D-Mannosamine-6-Phosphate Epimerase (NanE) in microorganism.

A technician in this field may understand that, to increase the effects of N-Acetyl-D-Mannosamine-6-Phosphate Epimerase (NanE) in microorganism, it may be realized by screening for a gene mutant encoding N-Acetyl-D-Mannosamine-6-Phosphate Epimerase (NanE) with increased activities. The screening for a NanE gene mutant may be achieved by error-prone PCR technology to produce a high-frequency mutant gene. To increase the effects of N-Acetyl-D-Mannosamine-Phosphate Epimerase (NanE) in microorganism, it may also be realized by increasing its gene copies or replacing it with a promoter with a higher expression level than that of the natural promoter, for overexpression of N-Acetyl-D-Mannosamine-6-Phosphate Epimerase (NanE). In a specific implementation scheme, the microorganism are transformed by molecules of at least recombinant nucleic acid molecules, containing at least one genetic modification that may increase the effects of N-Acetyl-D-Mannosamine-6-Phosphate Epimerase (NanE) in microorganism.

In a preferably optimized implementation scheme, the microorganism are transformed by molecules of recombinant nucleic acid, containing one nucleotide sequence encoding N-Acetyl-D-Mannosamine-6-Phosphate Epimerase (NanE).

On the other hand, the nucleotide sequence encoding N-Acetyl-D-Mannosamine-6-Phosphate Epimerase (NanE) contains at least one genetic modification that may increase the activities of N-Acetyl-D-Mannosamine-6-Phophate Epimerase (NanE). Preferably the said genetic modification contains one or more substitutions at the following corresponding sites of SEQ ID NO: 29: Substitution of cysteine at Site 133 by arginine, and substitution of tyrosine at Site 187 by histidine. More preferably, the nucleic acid sequence encoding N-Acetyl-D-Mannosamine-6-Phosphate Epimerase (NanE) is SEQ ID NO: 56; the amino acid sequence of the said N-Acetyl-D-Mannosamine-6-Phosphate Epimerase (NanE) is SEQ ID NO: 57.

On the other hand, at least approximately 30% (more preferably at least approximately 50%, further more preferably at least approximately 70%, further more preferably at least approximately 80%, and further more at least approximately 90%, and most preferably at least approximately 95%) of the amino acid sequence of the said N-Acetyl-D-Mannosamine-6-Phosphate Epimerase (NanE) is the same as that of SEQ ID NO: 29, where the said N-Acetyl-D-Mannosamine-6-Phosphate Epimerase (NanE) is active.

On the other hand, the said N-Acetyl-D-Mannosamine-6-Phosphate Epimerase (NanE) has the amino acid sequence of SEQ ID NO: 29.

On the other hand, the gene copies in the recombinant nucleic acid molecules, encoding N-Acetyl-D-Mannosamine-6-Phosphate Epimerase (NanE), are increased.

On the other hand, the recombinant nucleic acid molecules contain an endogenous promoter, with a higher expression level of promoters, enhancers, and fusion sequences, etc., than those of natural endogenous promoters. Preferably, the recombinant nucleic acid molecules contains a higher expression level of promoters than that of natural endogenous promoters, such as HCE promoter, gap promoter, trc promoter, and T7 promoter, etc.; more preferably, the recombinant nucleic acid molecules contain trc promoter.

In this Invention, microorganism transformed by recombinant nucleic acid molecules transform are selected from free type (that is to say, recombinant nucleic acid molecules are mounted into plasmids) and integrated type (that is to say, recombinant nucleic acid molecules are integrated into the genomes of microorganism). Preferably, recombinant nucleic acid molecules are integrated into the genomes of microorganism.

In another preferably optimized implementation scheme, the microorganism contain at least one genetic modification of the natural endogenous promoter to the gene encoding N-Acetyl-D-Mannosamine-6-Phosphate Epimerase (NanE). Preferably, the natural endogenous promoter with the gene encoding N-Acetyl-D-Mannosamine-6-Phosphate Epimerase (NanE) is replaced by a promoter with a higher expression level, such as HCE promoter, gap promoter, trc promoter, or T7 promoter, etc.; more preferably, the natural endogenous promoter with the gene encoding N-Acetyl-D-Mannosamine-6-Phosphate Epimerase (NanE) is replaced by trc promoter.

In respect to the above (2), the genetic modification increasing the effects of D-Glucosamine-6-Phosphate Deaminase (NagB) in microorganism is selected from a) increasing the effects of D-Glucosamine-6-Phosphate Deaminase (NagB) in microorganism; and/or b) overexpression of D-Glucosamine-6-Phosphate Deaminase (NagB) in microorganism.

A technician in this field may understand that, to increase the effects of D-Glucosamine-6-Phosphate Deaminase (NagB) in microorganism, it may be realized by screening for a gene mutant encoding D-Glucosamine-6-Phosphate Deaminase (NagB) with increased activities. The screening for a NanG gene mutant may be achieved by error-prone PCR technology to produce a high-frequency mutant gene. To increase the effects of D-Glucosamine-Phosphate Deaminase (NanB) in microorganism, it may also be realized by increasing its gene copies or replacing it with a promoter with a higher expression level than that of the natural promoter, for overexpression of D-Glucosamine-6-Phosphate Deaminase (NanB). In a specific implementation scheme, the microorganism are transformed by molecules of at least one recombinant nucleic acid, containing at least one genetic modification that may increase the effects of D-Glucosamine-6-Phosphate Deaminase (NanB) in microorganism.

In a preferably optimized implementation scheme, the microorganism are transformed by molecules of at least recombinant nucleic acid, containing one nucleotide sequence encoding D-Glucosamine-6-Phosphate Deaminase (NanB).

On the other hand, the nucleotide sequence encoding D-Glucosamine-6-Phosphate Deaminase (NanS) contains at least one genetic modification that may increase the activities of D-Glucosamine-6-Phosphate Deaminase (NanB).

On the other hand, the gene copies in the recombinant nucleic acid molecules, encoding D-Glucosamine-6-Phosphate Deaminase (NanB), are increased.

On the other hand, the recombinant nucleic acid molecules contain an endogenous promoter, with a higher expression level of promoters, enhancers, and fusion sequences, etc., than those of natural endogenous promoters. Preferably, the recombinant nucleic acid molecules contains a higher expression level of promoters than that of natural endogenous promoters, such as HCE promoter, gap promoter, trc promoter, and T7 promoter, etc.; more preferably, the recombinant nucleic acid molecules contain trc promoter.

In this Invention, microorganism transformed by recombinant nucleic acid molecules transform are selected from free type (that is to say, recombinant nucleic acid molecules are mounted into plasmids) and integrated type (that is to say, recombinant nucleic acid molecules are integrated into the genomes of microorganism). Preferably, recombinant nucleic acid molecules are integrated into the genomes of microorganism.

In another preferably optimized implementation scheme, the microorganism contain at least one genetic modification of the natural endogenous promoter to the gene encoding D-Glucosamine-6-Phosphate Deaminase (NanB). Preferably, the natural endogenous promoter with the gene encoding D-Glucosamine-6-Phosphate Deaminase (NanB) is replaced by a promoter with a higher expression level, such as HCE promoter, gap promoter, trc promoter, or T7 promoter, etc.; more preferably, the natural endogenous promoter with the gene encoding D-Glucosamine-6-Phosphate Deaminase (NanB) is replaced by trc promoter.

In this Invention, the genetic modifications decreasing the effects of Glucosamine-6-Phosphate Synthase (GlmS) in microorganism are selected from a) decreasing effects of Glucosamine-6-Phosphate Synthase (GlmS) in microorganism; and/or b) reducing expression of Glucosamine-6-Phosphate Synthase (GlmS) in microorganism, including but not limited to: Partial or complete deletion, or partial or complete deactivation of the endogenous gene encoding Glucosamine-6-Phosphate Synthase (GlmS), and/or partial or complete deletion, or partial or complete deactivation of the natural endogenous promoter with the gene encoding Glucosamine-6-Phosphate Synthase (GlmS). Preferably, the genetic modification decreasing the effects of Glucosamine-6-Phosphate Synthase (GlmS) in microorganism is complete deletion (loss) of the natural endogenous promoter with the gene encoding Glucosamine-6-Phosphate Synthase (GlmS) in microorganism.

In a specific implementation scheme, the microorganism are transformed by molecules of at least one recombinant nucleic acid, containing at least one genetic modification that may decrease the effects of Glucosamine-6-Phosphate Synthase (GlmS) in microorganism.

In respect to the above (3), the genetic modification increasing the effects of D-Glucosamine-6-Phosphate Synthase (GlmS) in microorganism is selected from a) increasing the effects of D-Glucosamine-6-Phosphate Synthase (GlmS) in microorganism; and/or b) overexpression of D-Glucosamine-6-Phosphate Synthase (GlmS) in microorganism.

A technician in this field may understand that, to increase the effects of D-Glucosamine-6-Phosphate Synthase (GlmS) in microorganism, it may be realized by screening for a gene mutant encoding D-Glucosamine-6-Phosphate Deaminase (NagB) with increased activities. The screening for a GlmS gene mutant may be achieved by error-prone PCR technology to produce a high-frequency mutant gene. To increase the effects of Glucosamine-Phosphate Synthase (GlmS) in microorganism, it may also be realized by increasing its gene copies or replacing it with a promoter with a higher expression level than that of the natural promoter, for overexpression of Glucosamine-6-Phosphate Synthase (GlmS). In a specific implementation scheme, the microorganism are transformed by molecules of at least one recombinant nucleic acid, containing at least one genetic modification that may increase the effects of D-Glucosamine-6-Phosphate Synthase (NanS) in microorganism.

In a preferably optimized implementation scheme, the microorganism are transformed by molecules of at least recombinant nucleic acid, containing one nucleotide sequence encoding Glucosamine-6-Phosphate Synthase (GlmS).

On the other hand, the nucleotide sequence encoding Glucosamine-6-Phosphate Synthase (GlmS) contains at least one genetic modification that may increase the activities of D-Glucosamine-6-Phosphate Synthase (GlmS).

On the other hand, the gene copies in the recombinant nucleic acid molecules, encoding D-Glucosamine-6-Phosphate Synthase (GlmS), are increased.

On the other hand, the recombinant nucleic acid molecules contain an endogenous promoter, with a higher expression level of promoters, enhancers, and fusion sequences, etc., than those of natural endogenous promoters.

Preferably, the recombinant nucleic acid molecules contains a higher expression level of promoters than that of natural endogenous promoters, such as HCE promoter, gap promoter, trc promoter, and T7 promoter, etc.; more preferably, the recombinant nucleic acid molecules contain trc promoter.

In this Invention, microorganism transformed by recombinant nucleic acid molecules transform are selected from free type (that is to say, recombinant nucleic acid molecules are mounted into plasmids) and integrated type (that is to say, recombinant nucleic acid molecules are integrated into the genomes of microorganism). Preferably, recombinant nucleic acid molecules are integrated into the genomes of microorganism.

In another preferably optimized implementation scheme, the microorganism contain at least one genetic modification of the natural endogenous promoter to the gene encoding Glucosamine-6-Phosphate Synthase (GlmS). Preferably, the natural endogenous promoter with the gene encoding Glucosamine-6-Phosphate Synthase (GlmS) is replaced by a promoter with a higher expression level, such as HCE promoter, gap promoter, trc promoter, or T7 promoter, etc.; more preferably, the natural endogenous promoter with the gene encoding Glucosamine-6-Phosphate Synthase (GlmS) is replaced by trc promoter.

In this Invention, the genetic modifications decreasing the effects of D-Glucosamine-6-Phosphate Deaminase (NagB) in microorganism are selected from a) decreasing effects of D-Glucosamine-6-Phosphate Deaminase (NagB) in microorganism; and/or b) reducing expression of D-Glucosamine-6-Phosphate Deaminase (NagB) in microorganism, including but not limited to: Partial or complete deletion, or partial or complete deactivation of the endogenous gene encoding D-Glucosamine-6-Phosphate Deaminase (NagB), and/or partial or complete deletion, or partial or complete deactivation of the natural endogenous promoter with the gene encoding Glucosamine-6-Phosphate Deaminase (NagB). Preferably, the genetic modification decreasing the effects of D-Glucosamine-6-Phosphate Deaminase (NagB) in microorganism is complete deletion (loss) of the natural endogenous promoter with the gene encoding D-Glucosamine-6-Phosphate Deaminase (NagB) in microorganism.

In a specific implementation scheme, the microorganism are transformed by molecules of at least one recombinant nucleic acid, containing at least one genetic modification that may decrease the effects of D-Glucosamine-6-Phosphate Deaminase (NanB) in microorganism.

In respect to the above (4), the genetic modification increasing the effects of UDP-N-Acetyl-D-Glucosamine-2-Epimerase (WecB) in microorganism is selected from a) increasing the effects of UDP-N-Acetyl-D-Glucosamine-2-Epimerase (WecB) in microorganism; and/or b) overexpression of UDP-N-Acetyl-D-Glucosamine-2-Epimerase (WecB) in microorganism.

A technician in this field may understand that, to increase the effects of UDP-N-Acetyl-D-Glucosamine-2-Epimerase (WecB) in microorganism, it may be realized by screening for a gene mutant encoding UDP-N-Acetyl-D-Glucosamine-2-Epimerase (WecB) with increased activities. The screening for a WecB gene mutant may be achieved by error-prone PCR technology to produce a high-frequency mutant gene. To increase the effects of UDP-N-Acetyl-D-Glucosamine-2-Epimerase (WecB) in microorganism, it may also be realized by increasing its gene copies or replacing it with a promoter with a higher expression level than that of the natural promoter, for overexpression of UDP-N-Acetyl-D-Glucosamine-2-Epimerase (WecB). In a specific implementation scheme, the microorganism are transformed by molecules of at least recombinant nucleic acid molecules, containing at least one genetic modification that may increase the effects of UDP-N-Acetyl-D-Glucosamine-2-Epimerase (WecB) in microorganism.

In a preferably optimized implementation scheme, the microorganism are transformed by molecules of recombinant nucleic acid, containing one nucleotide sequence encoding UDP-N-Acetyl-D-Glucosamine-2-Epimerase (WecB).

On the other hand, the nucleotide sequence encoding UDP-N-Acetyl-D-Glucosamine-2-Epimerase (WecB) contains at least one genetic modification that may increase the activities of UDP-N-Acetyl-D-Glucosamine-2-Epimerase (WecB). Preferably the said genetic modification contains one or more substitutions at the following corresponding sites of SEQ ID NO: 50: Substitution of cysteine at Site 34 by serine, substitution of histidine at site 145 by aspartate, substitution of cysteine at Site 226 by phenylalanine, and substitution of valine at Site 245 by glycine. More preferably, the nucleic acid sequence encoding UDP-N-Acetyl-D-Glucosamine-2-Epimerase (WecB) is SEQ ID NO: 58; the amino acid sequence of the said UDP-N-Acetyl-D-Glucosamine-2-Epimerase (WecB) is SEQ ID NO: 59.

On the other hand, at least approximately 30% (more preferably at least approximately 50%, further more preferably at least approximately 70%, further more preferably at least approximately 80%, and further more at least approximately 90%, and most preferably at least approximately 95%) of the amino acid sequence of the said UDP-N-Acetyl-D-Glucosamine-2-Epimerase (WecB) is the same as that of SEQ ID NO: 50, where the said UDP-N-Acetyl-D-Glucosamine-2-Epimerase (WecB) is active.

On the other hand, the said UDP-N-Acetyl-D-Glucosamine-2-Epimerase (WecB) has the amino acid sequence of SEQ ID NO: 50.

On the other hand, the gene copies in the recombinant nucleic acid molecules, encoding UDP-N-Acetyl-D-Glucosamine-2-Epimerase (WecB), are increased.

On the other hand, the recombinant nucleic acid molecules contain an endogenous promoter, with a higher expression level of promoters, enhancers, and fusion sequences, etc., than those of natural endogenous promoters. Preferably, the recombinant nucleic acid molecules contains a higher expression level of promoters than that of natural endogenous promoters, such as HCE promoter, gap promoter, trc promoter, and T7 promoter, etc.; more preferably, the recombinant nucleic acid molecules contain trc promoter.

In this Invention, microorganism transformed by recombinant nucleic acid molecules transform are selected from free type (that is to say, recombinant nucleic acid molecules are mounted into plasmids) and integrated type (that is to say, recombinant nucleic acid molecules are integrated into the genomes of microorganism). Preferably, recombinant nucleic acid molecules are integrated into the genomes of microorganism.

In another preferably optimized implementation scheme, the microorganism contain at least one genetic modification of the natural endogenous promoter to the gene encoding UDP-N-Acetyl-D-Glucosamine-2-Epimerase (WecB). Preferably, the natural endogenous promoter with the gene encoding DP-N-Acetyl-D-Glucosamine-2-Epimerase (WecB) is replaced by a promoter with a higher expression level, such as HCE promoter, gap promoter, trc promoter, or T7 promoter, etc.; more preferably, the natural endogenous promoter with the gene encoding UDP-N-Acetyl-D-Glucosamine-2-Epimerase (WecB) is replaced by trc promoter.

Based on the preferably optimized implementation scheme, the said microorganism contains one or more of the following genetic modifications:

(1) Contain at least genetic modification that may decrease the effects of Mannose transporter EIIM, P/III$^{man}$ (ManXYZ) in microorganism;

(2) Contain at least one genetic modification that may decrease the effects of N-Acetylneuraminate Lyase (NanA) in microorganism;

(3) Contain at least one genetic modification that may decrease the effects of N-Acetyl-D-Glucosamine-6-Phosphate Deactylase (NagA) in microorganism;

(4) Contain at least one genetic modification that may decrease the effects of N-Acetyl-D-Glucosamine Specific Enzyme II$^{Nag}$ (NagE) in microorganism;

(5) Contain at least one genetic modification that may increase the effects of PhosphoGlucosamine Mutase (GlmM) in microorganism;

(6) Contain at least one genetic modification that may increase the effects of bifunctional N-acetyl Glucosamine-1-Phosphate Uridyltransferase (GlmU) in microorganism;

In respect to the above (1), the genetic modifications decreasing the effects of Mannose transporter EIIM, P/III$^{man}$ (ManXYZ) in microorganism include but not limited to: Partial or complete deletion, or partial or complete deactivation of the endogenous gene encoding Mannose transporter EIIM, P/III$^{man}$ (ManXYZ), and/or partial or complete deletion, or partial or complete deactivation of the natural endogenous promoter with the gene encoding Mannose transporter EIIM, P/III$^{man}$ (ManXYZ). Preferably, the genetic modification decreasing the effects of Mannose transporter EIIM, P/III$^{man}$(ManXYZ) in microorganism is complete deletion (loss) of the endogenous gene encoding EIIM, P/III$^{man}$(ManXYZ) in microorganism. In a specific implementation scheme, the microorganism are transformed by molecules of at least one recombinant nucleic acid, containing at least one genetic modification that may decrease the effects of Mannose transporter EIIM, P/III$^{man}$ (ManXYZ) in microorganism.

In respect to the above (2), the genetic modifications decreasing the effects of N-Acetylneuraminate Lyase (NanA) in microorganism include but not limited to: Partial or complete deletion, or partial or complete deactivation of the endogenous gene encoding N-Acetylneuraminate Lyase (NanA), and/or partial or complete deletion, or partial or complete deactivation of the natural endogenous promoter with the gene encoding N-Acetylneuraminate Lyase (NanA). Preferably, the genetic modification decreasing the effects of N-Acetylneuraminate Lyase (NanA) in microorganism is complete deletion (loss) of the natural endogenous gene encoding N-Acetylneuraminate Lyase (NanA) in microorganism. In a specific implementation scheme, the microorganism are transformed by molecules of at least recombinant nucleic acid, containing at least one genetic modification that may decrease the effects of N-Acetylneuraminate Lyase (NanA) in microorganism.

In respect to the above (3), the genetic modifications decreasing the effects of N-Acetyl-D-Glucosamine-6-Phosphate Deactylase (NagA) in microorganism include but not limited to: Partial or complete deletion, or partial or complete deactivation of the endogenous gene encoding N-Acetyl-D-Glucosamine-6-Phosphate Deactylase (NagA), and/or partial or complete deletion, or partial or complete deactivation of the natural endogenous promoter with the gene encoding N-Acetyl-D-Glucosamine-6-Phosphate Deactylase (NagA). Preferably, the genetic modification decreasing the effects of N-Acetyl-D-Glucosamine-6-Phosphate Deactylase (NagA) in microorganism is complete deletion (loss) of the natural endogenous promoter with the gene encoding N-Acetyl-D-Glucosamine-6-Phosphate Deactylase (NagA) in microorganism. In a specific implementation scheme, the microorganism are transformed by molecules of at least one recombinant nucleic acid, containing at least one genetic modification that may decrease the effects of N-Acetyl-D-Glucosamine-6-Phosphate Deactylase (NagA) in microorganism.

In respect to the above (4), the genetic modifications decreasing the effects of N-Acetyl-D-Glucosamine Specific Enzyme II$^{Nag}$ (NagE) in microorganism include but not limited to: Partial or complete deletion, or partial or complete deactivation of the endogenous gene encoding N-Acetyl-D-Glucosamine Specific Enzyme II$^{Nag}$ (NagE), and/or partial or complete deletion, or partial or complete deactivation of the natural endogenous promoter with the gene encoding N-Acetyl-D-Glucosamine Specific Enzyme II$^{Nag}$ (NagE). Preferably, the genetic modification decreasing the effects of N-Acetyl-D-Glucosamine Specific Enzyme II$^{Nag}$ (NagE) in microorganism is complete deletion (loss) of the natural endogenous promoter with the gene encoding N-Acetyl-D-Glucosamine Specific Enzyme II$^{Nag}$ (NagE) in microorganism. In a specific implementation scheme, the microorganism are transformed by molecules of at least one recombinant nucleic acid, containing at least one genetic modification that may decrease the effects of N-Acetyl-D-Glucosamine Specific Enzyme II$^{Nag}$ (NagE) in microorganism.

In respect to the above (5), the genetic modification increasing the effects of PhosphoGlucosamine Mutase (GlmM) in microorganism is selected from a) increasing the effects of PhosphoGlucosamine Mutase (GlmM) in microorganism; and/or b) overexpression of PhosphoGlucosamine Mutase (GlmM) in microorganism.

A technician in this field may understand that, to increase the effects of PhosphoGlucosamine Mutase (GlmM) in microorganism, it may be realized by screening for a gene mutant encoding PhosphoGlucosamine Mutase (GlmM) with increased activities. The screening for a GlmM gene mutant may be achieved by error-prone PCR technology to produce a high-frequency mutant gene. To increase the effects of PhosphoGlucosamine Mutase (GlmM) in microorganism, it may also be realized by increasing its gene copies or replacing it with a promoter with a higher expression level than that of the natural promoter, for overexpression of PhosphoGlucosamine Mutase (GlmM). In a specific implementation scheme, the microorganism are transformed by molecules of at least one recombinant nucleic acid, containing at least one genetic modification that may increase the effects of PhosphoGlucosamine Mutase (GlmM) in microorganism.

In a preferably optimized implementation scheme, the microorganism are transformed by molecules of at least recombinant nucleic acid, containing one nucleotide sequence encoding PhosphoGlucosamine Mutase (GlmM).

On the other hand, the nucleotide sequence encoding PhosphoGlucosamine Mutase (GlmM) contains at least one genetic modification that may increase the activities of PhosphoGlucosamine Mutase (GlmM).

On the other hand, the gene copies in the recombinant nucleic acid molecules, encoding PhosphoGlucosamine Mutase (GlmM), are increased.

On the other hand, the recombinant nucleic acid molecules contain an endogenous promoter, with a higher expression level of promoters, enhancers, and fusion sequences, etc., than those of natural endogenous promoters. Preferably, the recombinant nucleic acid molecules contains a higher expression level of promoters than that of natural endogenous promoters, such as HCE promoter, gap promoter, trc promoter, and T7 promoter, etc.; more preferably, the recombinant nucleic acid molecules contain trc promoter.

In this Invention, microorganism transformed by recombinant nucleic acid molecules transform are selected from free type (that is to say, recombinant nucleic acid molecules are mounted into plasmids) and integrated type (that is to say, recombinant nucleic acid molecules are integrated into the genomes of microorganism). Preferably, recombinant nucleic acid molecules are integrated into the genomes of microorganism.

In another preferably optimized implementation scheme, the microorganism contain at least one genetic modification of the natural endogenous promoter to the gene encoding PhosphoGlucosamine Mutase (GlmM). Preferably, the natural endogenous promoter with the gene encoding PhosphoGlucosamine Mutase (GlmM) is replaced by a promoter with a higher expression level, such as HCE promoter, gap promoter, trc promoter, or T7 promoter, etc.; more preferably, the natural endogenous promoter with the gene encoding PhosphoGlucosamine Mutase (GlmM) is replaced by trc promoter.

In respect to the above (6), the genetic modification increasing the effects of bifunctional N-acetyl Glucosamine-1-Phosphate Uridyltransferase (GlmU) in microorganism is selected from a) increasing the effects of bifunctional N-acetyl Glucosamine-1-Phosphate Uridyltransferase (GlmU) in microorganism; and/or b) overexpression of bifunctional N-acetyl Glucosamine-1-Phosphate Uridyltransferase (GlmU) in microorganism.

A technician in this field may understand that, to increase the effects of bifunctional N-acetyl Glucosamine-1-Phosphate Uridyltransferase (GlmU) in microorganism, it may be realized by screening for a gene mutant encoding of bifunctional N-acetyl Glucosamine-1-Phosphate Uridyltransferase (GlmU) with increased activities. The screening for a GlmU gene mutant may be achieved by error-prone PCR technology to produce a high-frequency mutant gene. To increase the effects of bifunctional N-acetyl Glucosamine-1-Phosphate Uridyltransferase (GlmU) in microorganism, it may also be realized by increasing its gene copies or replacing it with a promoter with a higher expression level than that of the natural promoter, for overexpression of bifunctional N-acetyl Glucosamine-1-Phosphate Uridyltransferase (GlmU). In a specific implementation scheme, the microorganism are transformed by molecules of at least recombinant nucleic acid molecules, containing at least one genetic modification that may increase the effects of bifunctional N-acetyl Glucosamine-1-Phosphate Uridyltransferase (GlmU) in microorganism.

In a preferably optimized implementation scheme, the microorganism are transformed by molecules of at least recombinant nucleic acid, containing one nucleotide sequence encoding bifunctional N-acetyl Glucosamine-1-Phosphate Uridyltransferase (GlmU).

On the other hand, the nucleotide sequence encoding bifunctional N-acetyl Glucosamine-1-Phosphate Uridyltransferase (GlmU) contains at least one genetic modification that may increase the activities of bifunctional N-acetyl Glucosamine-1-Phosphate Uridyltransferase (GlmU).

On the other hand, the gene copies in the recombinant nucleic acid molecules, encoding bifunctional N-acetyl Glucosamine-1-Phosphate Uridyltransferase (GlmU), are increased.

On the other hand, the recombinant nucleic acid molecules contain an endogenous promoter, with a higher expression level of promoters, enhancers, and fusion sequences, etc., than those of natural endogenous promoters. Preferably, the recombinant nucleic acid molecules contains a higher expression level of promoters than that of natural endogenous promoters, such as HCE promoter, gap promoter, trc promoter, and T7 promoter, etc.; more preferably, the recombinant nucleic acid molecules contain trc promoter.

In this Invention, microorganism transformed by recombinant nucleic acid molecules transform are selected from free type (that is to say, recombinant nucleic acid molecules are mounted into plasmids) and integrated type (that is to say, recombinant nucleic acid molecules are integrated into the genomes of microorganism). Preferably, recombinant nucleic acid molecules are integrated into the genomes of microorganism.

In another preferably optimized implementation scheme, the microorganism contain at least one genetic modification of the natural endogenous promoter to the gene encoding bifunctional N-acetyl Glucosamine-1-Phosphate Uridyltransferase (GlmU). Preferably, the natural endogenous promoter with the gene encoding bifunctional N-acetyl Glucosamine-1-Phosphate Uridyltransferase (GlmU) is replaced by a promoter with a higher expression level, such as HCE promoter, gap promoter, trc promoter, or T7 promoter, etc.; more preferably, the natural endogenous promoter with the gene encoding bifunctional N-acetyl Glucosamine-1-Phosphate Uridyltransferase (GlmU) is replaced by trc promoter.

This Invention is further involved with the following preferably optimized implementation schemes:

1. Based on one preferably optimized implementation scheme of the Invention, the Invention is involved with the method for production of N-Acetyl-D-Glucosamine (GlcNAc) and/or D-Glucosamine Salt by microbial fermentation, which includes:

A) Cultivation of microorganism in the fermentation medium, where the said microorganism contains: At least one genetic modification that may increase the effects of N-Acetyl-D-Mannosamine Kinase (NanK) in microorganism; at least one genetic modification that may increase the effects of N-Acetyl-D-Mannosamine-6-Phosphate Epimerase (NanE) in microorganism; and B) Collection of N-Acetyl-D-Glucosamine (GlcNAc) produced in the cultivation step A).

2. Based on another preferably optimized implementation scheme of the Invention, the Invention is involved with the method for production of N-Acetyl-D-Glucosamine (GlcNAc) and/or D-Glucosamine Salt by microbial fermentation, which includes:

A) Cultivation of microorganism in the fermentation medium, where the said microorganism contains: At least one genetic modification that may increase the effects of N-Acetyl-D-Mannosamine Kinase (NanK) in microorganism; and at least one genetic modification that may increase the effects of D-Glucosamine-6-Phosphate Deaminase (NagB) in microorganism; and B) Collection of N-Acetyl-D-Glucosamine (GlcNAc) produced in the cultivation step A).

Preferably, the said microorganism also contain at least one genetic modification that may decrease the effects of D-Glucosamine-6-Phosphate Synthase (GlmS) in microorganism.

3. Based on another preferably optimized implementation scheme of the Invention, the Invention is involved with the method for production of N-Acetyl-D-Glucosamine (GlcNAc) and/or D-Glucosamine Salt by microbial fermentation, which includes:

A) Cultivation of microorganism in the fermentation medium, where the said microorganism contains: At least one genetic modification that may increase the effects of N-Acetyl-D-Mannosamine Kinase (NanK) in microorganism; at least one genetic modification that may increase the effects of Glucosamine-6-Phosphate Synthase (GlmS) in microorganism; and at least one genetic modification that may decrease the effects of D-Glucosamine-6-Phosphate Deaminase (NagB); and B) Collection of N-Acetyl-D-Glucosamine (GlcNAc) produced in the cultivation step A).

4. Based on another preferably optimized implementation scheme of the Invention, the Invention is involved with the method for production of N-Acetyl-D-Glucosamine (GlcNAc) and/or D-Glucosamine Salt by microbial fermentation, which includes:

A) Cultivation of microorganism in the fermentation medium, where the said microorganism contains: At least one genetic modification that may increase the effects of N-Acetyl-D-Mannosamine Kinase (NanK) in microorganism; at least one genetic modification that may increase the effects of N-Acetyl-D-Mannosamine-6-Phosphate Epimerase (NanE) in microorganism; and at least one genetic modification that may increase the effects of D-Glucosamine-6-Phosphate Deaminase (NagB) in microorganism; and B) Collection of N-Acetyl-D-Glucosamine (GlcNAc) produced in the cultivation step A).

Preferably, the said microorganism also contain at least one genetic modification that may decrease the effects of D-Glucosamine-6-Phosphate Synthase (GlmS) in microorganism.

5. Based on another preferably optimized implementation scheme of the Invention, the Invention is involved with the method for production of N-Acetyl-D-Glucosamine (GlcNAc) and/or D-Glucosamine Salt by microbial fermentation, which includes:

A) Cultivation of microorganism in the fermentation medium, where the said microorganism contains: At least one genetic modification that may increase the effects of N-Acetyl-D-Mannosamine Kinase (NanK) in microorganism; at least one genetic modification that may increase the effects of N-Acetyl-D-Mannosamine-6-Phosphate Epimerase (NanE) in microorganism; at least one genetic modification that may increase the effects of Glucosamine-6-Phosphate Synthase (GlmS) in microorganism; and at least one genetic modification that may decrease the effects of D-Glucosamine-6-Phosphate Deaminase (NagB); and B) Collection of N-Acetyl-D-Glucosamine (GlcNAc) produced in the cultivation step A).

6. Based on another preferably optimized implementation scheme of the Invention, the Invention is involved with the method for production of N-Acetyl-D-Glucosamine (GlcNAc) and/or D-Glucosamine Salt by microbial fermentation, which includes:

A) Cultivation of microorganism in the fermentation medium, where the said microorganism contains: At least one genetic modification that may increase the effects of N-Acetyl-D-Mannosamine Kinase (NanK) in microorganism; and at least one genetic modification that may increase the effects of UDP-N-Acetyl-D-Glucosamine-2-Epimerase (WecB) in microorganism; and B) Collection of N-Acetyl-D-Glucosamine (GlcNAc) produced in the cultivation step A).

7. Based on another preferably optimized implementation scheme of the Invention, the Invention is involved with the method for production of N-Acetyl-D-Glucosamine (GlcNAc) and/or D-Glucosamine Salt by microbial fermentation, which includes:

A) Cultivation of microorganism in the fermentation medium, where the said microorganism contains: At least one genetic modification that may increase the effects of N-Acetyl-D-Mannosamine Kinase (NanK) in microorganism; at least one genetic modification that may increase the effects of N-Acetyl-D-Mannosamine-6-Phosphate Epimerase (NanE) in microorganism; and at least one genetic modification that may increase the effects of UDP-N-Acetyl-D-Glucosamine-2-Epimerase (WecB) in microorganism; and B) Collection of N-Acetyl-D-Glucosamine (GlcNAc) produced in the cultivation step A).

8. Based on another preferably optimized implementation scheme of the Invention, the Invention is involved with the method for production of N-Acetyl-D-Glucosamine (GlcNAc) and/or D-Glucosamine Salt by microbial fermentation, which includes:

A) Cultivation of microorganism in the fermentation medium, where the said microorganism contains: At least one genetic modification that may increase the effects of N-Acetyl-D-Mannosamine Kinase (NanK) in microorganism; at least one genetic modification that may increase the effects of D-Glucosamine-6-Phosphate Deaminase (NagB) in microorganism; and at least one genetic modification that may increase the effects of UDP-N-Acetyl-D-Glucosamine-2-Epimerase (WecB) in microorganism; and B) Collection of N-Acetyl-D-Glucosamine (GlcNAc) produced in the cultivation step A).

Preferably, the said microorganism also contain at least one genetic modification that may decrease the effects of D-Glucosamine-6-Phosphate Synthase (GlmS) in microorganism.

9. Based on another preferably optimized implementation scheme of the Invention, the Invention is involved with the method for production of N-Acetyl-D-Glucosamine (GlcNAc) and/or D-Glucosamine Salt by microbial fermentation, which includes:

A) Cultivation of microorganism in the fermentation medium, where the said microorganism contains: At least one genetic modification that may increase the effects of N-Acetyl-D-Mannosamine Kinase (NanK) in microorganism; at least one genetic modification that may increase the effects of Glucosamine-6-Phosphate Synthase (GlmS) in microorganism; at least one genetic modification that may decrease the effects of D-Glucosamine-6-Phosphate Deaminase (NagB); and at least one genetic modification that may increase the effects of UDP-N-Acetyl-D-Glucosamine-2-Epimerase (WecB) in microorganism; and B) Collection of N-Acetyl-D-Glucosamine (GlcNAc) produced in the cultivation step A).

10. Based on another preferably optimized implementation scheme of the Invention, the Invention is involved with the method for production of N-Acetyl-D-Glucosamine (GlcNAc) and/or D-Glucosamine Salt by microbial fermentation, which includes:

A) Cultivation of microorganism in the fermentation medium, where the said microorganism contains: At least one genetic modification that may increase the effects of N-Acetyl-D-Mannosamine Kinase (NanK) in microorganism; at least one genetic modification that may increase the effects of N-Acetyl-D-Mannosamine-6-Phosphate Epimerase (NanE) in microorganism; at least one genetic modification that may increase the effects of D-Glucosamine-6-Phosphate Deaminase (NagB) in microorganism; and at least one genetic modification that may increase the effects of UDP-N-Acetyl-D-Glucosamine-2-Epimerase (WecB) in microorganism; and B) Collection of N-Acetyl-D-Glucosamine (GlcNAc) produced in the cultivation step A).

Preferably, the said microorganism also contain at least one genetic modification that may decrease the effects of D-Glucosamine-6-Phosphate Synthase (GlmS) in microorganism.

11. Based on another preferably optimized implementation scheme of the Invention, the Invention is involved with the method for production of N-Acetyl-D-Glucosamine (GlcNAc) and/or D-Glucosamine Salt by microbial fermentation, which includes:

A) Cultivation of microorganism in the fermentation medium, where the said microorganism contains: At least one genetic modification that may increase the effects of N-Acetyl-D-Mannosamine Kinase (NanK) in microorganism; at least one genetic modification that may increase the effects of N-Acetyl-D-Mannosamine-6-Phosphate Epimerase (NanE) in microorganism; at least one genetic modification that may increase the effects of Glucosamine-6-Phosphate Synthase (GlmS) in microorganism; at least one genetic modification that may decrease the effects of D-Glucosamine-6-Phosphate Deaminase (NagB); and at least one genetic modification that may increase the effects of UDP-N-Acetyl-D-Glucosamine-2-Epimerase (WecB) in microorganism; and B) Collection of N-Acetyl-D-Glucosamine (GlcNAc) produced in the cultivation step A).

In the above preferably optimized implementation schemes, further include C) Deacetylation of N-Acetyl-D-Glucosamine (GlcNAc) to produce D-Glucosamine Salt.

In the above preferably optimized implementation schemes, the microorganism further contain: At least one genetic modification that may decrease the effects of Mannose transporter EIIM, P/III$^{man}$ (ManXYZ) in microorganism; at least one genetic modification that may decrease the effects of N-Acetylneuraminate Lyase (NanA) in microorganism; at least one genetic modification that may decrease the effects of N-Acetyl-D-Glucosamine-6-Phosphate Deactylase (NagA) in microorganism; at least one genetic modification that may decrease the effects of N-Acetyl-D-Glucosamine Specific Enzyme II$^{Nag}$ (NagE) in microorganism.

On one hand for any of the above implementation schemes, the above recombinant nucleic acid molecules may be induced, including but not limited to induction by lactose; for example, it may realize expression induced by lactase, by adding lactose to the culture solution.

A technician in this field may understand that, various known common fermentation media in this field may be used in this Invention. On the one hand, the fermentation media contain carbon source. On the other hand, the fermentation media contain nitrogen sources. On the other hand, the fermentation media contain both carbon sources and nitrogen sources. On the other hand, the fermentation media contain carbon sources, nitrogen sources, and inorganic salts.

A technician in this field may understand that, various known carbon sources in this field may be used in this Invention, including organic and/or inorganic carbon sources. Preferably, carbon sources are selected from one or more of glucose, fructose, sucrose, galactose, dextrin, glycerin, starch, syrup, and molasses. Preferably, the concentration of a carbon source is maintained in the range of approximately 0.1%-approximately 5%. A technician in this field may understand that, various known nitrogen sources in this field may be used in this Invention, including organic and/or inorganic nitrogen sources. Preferably, nitrogen sources are selected from one or more of ammonia water, ammonium chloride, ammonium sulfate, ammonium nitrate, ammonium acetate, sodium nitrate, urea, yeast extract, meat extract, peptone, fish meal, bean flour, malt, corn syrup, and cotton seed meal.

Preferably, this Invention uses feed-batch fermentation method. Base on one aspect of this Invention, the carbohydrate supplement solution contains glucose and ribose; preferably, the concentration of glucose is 10%-85% (w/v), and that of ribose is 0.5%-15% (w/v); further preferably, the concentration of glucose is 55%-75% (w/v), and that of ribose is 5%-7% (w/v). Base on one aspect of this Invention, the carbohydrate supplement solution contains glucose and gluconate; preferably, the concentration of glucose is 10%-85% (w/v), and that of gluconate is 0.5%-15% (w/v); further preferably, the concentration of glucose is 55%-75% (w/v), and that of gluconate is 2%-3% (w/v). Base on one aspect of this Invention, the carbohydrate supplement solution contains glucose, ribose, and gluconate; preferably, the concentration of glucose is 10%-85% (w/v), that of gluconate is 0.5%-15% (w/v), and that of gluconate is 0.5%-15% (w/v); further preferably, the concentration of glucose is 55%-75% (w/v), that of gluconate is 5%-7% (w/v), and that of gluconate is 2%-3% (w/v); Preferably, gluconate is sodium gluconate.

In preferably optimized implementation schemes, the said cultivation step is carried out at approximately 20° C.~approximately 45° C.; further preferably, the said cultivation step is carried out at approximately 33° C.~approximately 37° C.

In preferably optimized implementation schemes, the said cultivation stem is carried out at approximately pH4.5~approximately pH8.5. Further preferably, the said cultivation step is carried out at approximately pH6.7~approximately pH7.2.

A technician in this field may understand that, various known common methods may be used to collect N-Acetyl-D-Glucosamine in this Invention. Preferably, N-Acetyl-D-Glucosamine may be collected from extracellular products in the fermentation medium. Further preferably, the collection step includes one selected from the following steps: (a) N-Acetyl-D-Glucosamine is precipitated in the fermentation liquid in which microorganism are removed; (b) N-Acetyl-D-Glucosamine is crystallized from the fermentation liquid in which microorganism are removed.

Based on this Invention, the collection step further includes a decoloration step of the fermentation liquid. The decoloration step may include but not limited to conduction prior to precipitation or crystallization of the fermentation liquid, and after one or multiple redissolution of precipitates or crystals in the fermentation liquid; the decoloration include activated charcoal treatment and/or chromatographic decoloration. The said chromatographic decoloration includes a step for exposure of the said fermentation liquid to an ion exchange resin. The said ion exchange resins include but not limited to anion exchange resin and/or cation exchange resin; for example, the fermentation liquid is exposed to a mixed bed containing anion and cation exchange resins.

Based on this Invention, N-Acetyl-D-Glucosamine may be deacetylated to produce a D-Glucosamine salt. The said salts include but not limited to hydrochloride, sulfate, sodium salt, phosphate, and bisulfate, etc. For example, N-Acetyl-D-Glucosamine may be deacetylated and hydrolized under acidic and heating conditions a D-Glucosamine salt. Preferably, N-Acetyl-D-Glucosamine may be deacetylated and hydrolized in 30%-37% hydrochloric acid and at 60-90° C. to produce N-Glucosamine Hydrochloride; N-Acetyl-D-Glucosamine may also be hydrolyzed under UDP-3-O—N-Acetylglucosamine Deacetylase to produce D-Glucosamine and further to produce a salt.

Based on another implementation scheme of this Invention, this Invention is involved with one microorganism. The said microorganism contains at least one genetic modification that may increase the effects of N-Acetyl-D-Mannosamine Kinase (NanK) in microorganism. The above text has described detailedly the genetic modification.

Based on the preferably optimized implementation scheme, the said microorganism contains one or more of the following genetic modifications:

(1) Contain at least one genetic modification that may increase the effects of N-Acetyl-D-Mannosamine-6-Phosphate Epimerase (NanE) in microorganism;

(2) Contain at least one genetic modification that may increase the effects of D-Glucosamine-6-Phosphate Deaminase (NagB) in microorganism, and preferably contain at lest one genetic modification that may decrease the effects of Glucosamine-6-Phosphate Synthase (GlmS);

(3) Contain at least one genetic modification that may increase the effects of D-Glucosamine-6-Phosphate Synthase (GlmS) in microorganism, and preferably contain at lest one genetic modification that may decrease the effects of D-Glucosamine-6-Phosphate Deaminase (NagB)

(4) Contain at least one genetic modification that may increase the effects of UDP-N-Acetyl-D-Glucosamine-2-Epimerase (WecB) in microorganism; The above text has described detailedly the genetic modifications.

Based on the preferably optimized implementation scheme, the said microorganism contains one or more of the following genetic modifications:

(1) Contain at least genetic modification that may decrease the effects of Mannose transporter EIIM, P/III$^{man}$ (ManXYZ) in microorganism;

(2) Contain at least one genetic modification that may decrease the effects of N-Acetylneuraminate Lyase (NanA) in microorganism;

(3) Contain at least one genetic modification that may decrease the effects of N-Acetyl-D-Glucosamine-6-Phosphate Deactylase (NagA) in microorganism;

(4) Contain at least one genetic modification that may decrease the effects of N-Acetyl-D-Glucosamine Specific Enzyme II$^{Nag}$ (NagE) in microorganism;

(5) Contain at least one genetic modification that may increase the effects of PhosphoGlucosamine Mutase (GlmM) in microorganism;

(6) Contain at least one genetic modification that may increase the effects of bifunctional N-acetyl Glucosamine-1-Phosphate Uridyltransferase (GlmU) in microorganism; The above text has described detailedly the genetic modifications.

This Invention is further involved with the following preferably optimized implementation schemes:

1. Based on one preferably optimized implementation scheme of this Invention, this Invention is involved with one microorganism. The said microorganism contains at least one genetic modification that may increase the effects of N-Acetyl-D-Mannosamine Kinase (NanK) in microorganism; and at least one genetic modification that may increase the effects of N-Acetyl-D-Mannosamine-6-Phosphate Epimerase (NanE) in microorganism;

2. Based on another preferably optimized implementation scheme of this Invention, this Invention is involved with one microorganism. The said microorganism contains at least one genetic modification that may increase the effects of N-Acetyl-D-Mannosamine Kinase (NanK) in microorganism; and at least one genetic modification that may increase the effects of D-Glucosamine-6-Phosphate Deaminase (NagB) in microorganism.

Preferably, the said microorganism also contain at least one genetic modification that may decrease the effects of D-Glucosamine-6-Phosphate Synthase (GlmS) in microorganism.

3. Based on another preferably optimized implementation scheme of this Invention, this Invention is involved with one microorganism. The said microorganism contains at least one genetic modification that may increase the effects of N-Acetyl-D-Mannosamine Kinase (NanK) in microorganism; at least one genetic modification that may increase the effects of Glucosamine-6-Phosphate Synthase (GlmS) in microorganism; and east one genetic modification that may decrease the effects of D-Glucosamine-6-Phosphate Deaminase (NagB).

4. Based on one preferably optimized implementation scheme of this Invention, this Invention is involved with one microorganism. The said microorganism contains at least one genetic modification that may increase the effects of N-Acetyl-D-Mannosamine Kinase (NanK) in microorganism; at least one genetic modification that may increase the effects of N-Acetyl-D-Mannosamine-6-Phosphate Epimerase (NanE) in microorganism; and at least one genetic modification that may increase the effects of D-Glucosamine-6-Phosphate Deaminase (NagB) in microorganism.

Preferably, the said microorganism also contain at least one genetic modification that may decrease the effects of D-Glucosamine-6-Phosphate Synthase (GlmS) in microorganism.

5. Based on one preferably optimized implementation scheme of this Invention, this Invention is involved with one microorganism. The said microorganism contains at least one genetic modification that may increase the effects of N-Acetyl-D-Mannosamine Kinase (NanK) in microorganism; at least one genetic modification that may increase the effects of N-Acetyl-D-Mannosamine-6-Phosphate Epimerase (NanE) in microorganism; at least one genetic modification that may increase the effects of Glucosamine-6-Phosphate Synthase (GlmS) in microorganism; and east one genetic modification that may decrease the effects of D-Glucosamine-6-Phosphate Deaminase (NagB).

6. Based on one preferably optimized implementation scheme of this Invention, this Invention is involved with one microorganism. The said microorganism contains at least one genetic modification that may increase the effects of N-Acetyl-D-Mannosamine Kinase (NanK) in microorganism; and at least one genetic modification that may increase the effects of UDP-N-Acetyl-D-Glucosamine-2-Epimerase (WecB) in microorganism.

7. Based on one preferably optimized implementation scheme of this Invention, this Invention is involved with one microorganism. The said microorganism contains at least one genetic modification that may increase the effects of N-Acetyl-D-Mannosamine Kinase (NanK) in microorganism; at least one genetic modification that may increase the effects of N-Acetyl-D-Mannosamine-6-Phosphate Epimerase (NanE) in microorganism; and at least one genetic modification that may increase the effects of UDP-N-Acetyl-D-Glucosamine-2-Epimerase (WecB) in microorganism.

8. Based on another preferably optimized implementation scheme of this Invention, this Invention is involved with one microorganism. The said microorganism contains at least one genetic modification that may increase the effects of N-Acetyl-D-Mannosamine Kinase (NanK) in microorganism; at least one genetic modification that may increase the effects of D-Glucosamine-6-Phosphate Deaminase (NagB) in microorganism; and at least one genetic modification that may increase the effects of UDP-N-Acetyl-D-Glucosamine-2-Epimerase (WecB) in microorganism.

Preferably, the said microorganism also contain at least one genetic modification that may decrease the effects of D-Glucosamine-6-Phosphate Synthase (GlmS) in microorganism.

9. Based on another preferably optimized implementation scheme of this Invention, this Invention is involved with one microorganism. The said microorganism contains at least one genetic modification that may increase the effects of N-Acetyl-D-Mannosamine Kinase (NanK) in microorganism; at least one genetic modification that may increase the effects of Glucosamine-6-Phosphate Synthase (GlmS) in microorganism; at least one genetic modification that may decrease the effects of D-Glucosamine-6-Phosphate Deaminase (NagB); and at least one genetic modification that may increase the effects of UDP-N-Acetyl-D-Glucosamine-2-Epimerase (WecB) in microorganism.

10. Based on one preferably optimized implementation scheme of this Invention, this Invention is involved with one microorganism. The said microorganism contains at least one genetic modification that may increase the effects of N-Acetyl-D-Mannosamine Kinase (NanK) in microorganism; at least one genetic modification that may increase the effects of N-Acetyl-D-Mannosamine-6-Phosphate Epimerase (NanE) in microorganism; at least one genetic modification that may increase the effects of D-Glucosamine-6-Phosphate Deaminase (NagB) in microorganism; and at least one genetic modification that may increase the effects of UDP-N-Acetyl-D-Glucosamine-2-Epimerase (WecB) in microorganism.

Preferably, the said microorganism also contain at least one genetic modification that may decrease the effects of D-Glucosamine-6-Phosphate Synthase (GlmS) in microorganism.

11. Based on one preferably optimized implementation scheme of this Invention, this Invention is involved with one microorganism. The said microorganism contains at least one genetic modification that may increase the effects of N-Acetyl-D-Mannosamine Kinase (NanK) in microorganism; at least one genetic modification that may increase the effects of N-Acetyl-D-Mannosamine-6-Phosphate Epimerase (NanE) in microorganism; at least one genetic modification that may increase the effects of Glucosamine-6-Phosphate Synthase (GlmS) in microorganism; at least one genetic modification that may decrease the effects of D-Glucosamine-6-Phosphate Deaminase (NagB); and at least one genetic modification that may increase the effects of UDP-N-Acetyl-D-Glucosamine-2-Epimerase (WecB) in microorganism.

In the above preferably optimized implementation schemes, the microorganism further contain: At least one genetic modification that may decrease the effects of Mannose transporter EIIM, P/III$^{man}$ (ManXYZ) in microorganism; at least one genetic modification that may decrease the effects of N-Acetylneuraminate Lyase (NanA) in microorganism; at least one genetic modification that may decrease the effects of N-Acetyl-D-Glucosamine-6-Phosphate Deactylase (NagA) in microorganism; at least one genetic modification that may decrease the effects of N-Acetyl-D-Glucosamine Specific Enzyme II$^{Nag}$ (NagE) in microorganism.

Based on another implementation scheme of this Invention, this Invention is involved with one N-Acetyl-D-Mannosamine Kinase (NanK) with higher activities, which has the amino acid sequence as shown in SEQ ID NO: 27. This Invention is further involved with nucleic acid molecules encoding the above N-Acetyl-D-Mannosamine Kinase (NanK); the said nucleic acid molecules have the nucleic acid sequence as shown in SEQ ID NO: 26. This Invention is further involved with a carrier containing the above nucleic acid molecules. This Invention is further involved with a microorganism containing the above carrier. This Invention is further involved with a microorganism with genomes containing above nucleic acid molecules.

In this Invention, microorganism may be any one (such as bacteria, protozoan, algae, fungi, or other microorganisms). In a preferably optimized implementation scheme, the microorganisms include but not limited to bacteria, yeast, or fungi. Preferably, the said microorganism is selected from bacteria or yeasts. Further preferably, the bacteria include but not limited to bacteria selected from *Escherichia, Bacillus, Lactobacillus, Pseudomonas*, or *Streptomyces*; more preferably, the bacteria include but not limited to bacteria selected from *Escherichia coli, Bacillus subtilis, Bacillus licheniformis, Lactobacillus brevis, Pseudomonas aeruginosa*, or *Streptomyces lividans*. More preferably, the yeasts include but not limited to yeasts selected from *Saccharomyces, Schizosaccharomyces, Candida, Hansenula, Pichia, Kluveromyces*, and *Phaffia*; more preferably, the yeasts include but not limited to yeasts selected from *Saccharomyce scerevisiae, Schizosaccharo mycespombe, Candida albicans, Hansenulapolymorpha, Pichia pastoris, Pichia canadensis, Kluyveromyces marxianus*, or *Phaffia rohodozyma*. Preferably, the said microorganism is a fungus; more preferably, the said fungi include but not limited to fungi selected from *Aspergillus, Absidia, Rhizopus, Chrysosporium, Neurospora*, or *Trichoderma*; more preferably, the fungi include but not limited to those selected from *Aspergillus niger, Aspergillus nidulans, Absidia coerulea, Rhizopus oryzae, Chrysosporium lucknowense, Neurospora crassa, Neurospora intermedia*, or *Trichoderma reesei*. Particularly more preferably, the *Escherichia coli* strains include K-12, B, and W, and most preferably, include K-12. Although *Escherichia coli* are used as preferably optimized microorganism, and are used as example of the various implementation schemes of this Invention, it should be understood that this Invention may use any other microorganisms that may produce N-Acetyl-D-Glucosamine and may increase output of N-Acetyl-D-Glucosamine by a genetic modification. The microorganism used in this Invention may also be called as production organism.

In this Invention, the term N-Acetyl-D-Glucosamine may be called as 2-acetamido-2-deoxy-D-glucose. The terms N-Acetyl-D-Glucosamine, N-Acetyl-D-Glucosamine-6-

Phosphate and N-Acetyl-D-Glucosamine-1-Phosphate may be abbreviated to GlcNAc, GlcNAc-6-P, and GlcNAc-1-P, respectively. N-Acetyl-D-Glucosamine may also be abbreviated to NAG. Similar to N-Acetyl-D-Glucosamine and its derivatives, the terms D-Glucosamine, D-Glucosamine-6-Phosphate, and D-Glucosamine-1-Phophate may also be abbreviated to GlcN, GlcN-6-P, and GlcN-1-P. Similarly, the terms N-Acetyl-D-Mannosamine, N-Acetyl-D-Mannosamine-6-Phosphate, glucose, Glucose-6-Phosphate, and Fructose-6-Phosphate may also be abbreviated to ManNAc, ManNAc-6-P, Glc, Glc-6-P, and Fru-6-P, respectively.

The term "increasing the effects of an enzyme in microorganism" means increased activities the enzyme and/or overexpression of the enzyme, thus to increase output of the product manufactured from the substrate catalyzed by the enzyme in microorganism.

The term "decreasing the effects of an enzyme in microorganism" means decreased activities the enzyme and/or reduced expression of the enzyme, thus to decrease output of the product manufactured from the substrate catalyzed by the enzyme in microorganism.

The term "increased activities of an enzyme" means increased capacity of the enzyme to catalyze a certain chemical reaction. It encompasses increased capacity of the enzyme to catalyze an chemical reaction where the inhibition of the enzyme by the product, and the affinity of the enzyme to the substrate remain unchanged, and/or increased capacity resulted from decreased inhibition of the enzyme by the product, and/or from increased affinity of the enzyme to the substrate. The term "decreased inhibition of the enzyme by the product" means decreased activities of the enzyme to catalyze a reaction, due to specific inhibition of the enzyme by its end product. The term "increased affinity of the enzyme to the substrate" means increased affinity of the enzyme to the substrate to be catalyzed.

In FIG. 1, using *Escherichia coli* as example, it illustrates the major aspect of the genetic modification in the Glucosamine metabolic pathway used to manufacture N-Acetyl-D-Glucosamine in large scale, as disclosed in this Invention. In regard to FIG. 1, the bold arrow means metabolic produced and/or increased through genetic modification in this Invention. FIG. 1 discloses several synthetic methods used to synthesize N-Acetyl-D-Glucosamine, including a modification to NanK, may further include a modification to NanE, NagB, GlmS, or WecB, or their combination, and may also further include a modification to ManXYZ, NanA, NagA, NagE, GlmM, or GlmU, or their combination. A technician in this Field may understand that, other microorganisms have a similar carbohydrate metabolic pathway, and in such a metabolic pathway, the genes and proteins have similar structure and function. Therefore, the contents discussed in this Invention are applicable for both *Escherichia coli* and other microorganisms, and other microorganisms are obviously included in this Invention.

The enzyme known with the same biological activities in this field may have different names, dependent on the microorganism from which the enzyme is originated. Optional names of many enzymes and the name of a specific gene encoding such enzymes are provided below. The names of those enzymes may be used interchangeably, or may be used for a given sequence or organism if appropriate; however, this Invention is intended to include an enzyme with the specific function, originated from any organism.

For example, the enzyme generally called as "N-Acetyl-D-Mannosamine Kinase" in this article catalyzes phosphorylation of N-Acetyl-D-Mannosamine into N-Acetyl-D-Mannosamine-6-P. N-Acetyl-D-Mannosamine Kinase originated from *Escherichia coli* is generally called as NanK. N-Acetyl-D-Mannosamine Kinase originated from various organisms is well known in this field, and may be used in the genetic modification strategy in this Invention. For example, this article describes that N-Acetyl-D-Mannosamine Kinase originated from *Escherichia coli* has the nucleic acid sequence codes represented by SEQ ID NO: 16, and the amino acid sequence represented by SEQ ID NO: 17.

The enzyme generally called as "N-Acetyl-D-Mannosamine-6-P Epimerase" in this article catalyzes transformation of N-Acetyl-D-Mannosamine-6-P into N-Acetyl-D-Glucosamine-6-P. N-Acetyl-D-Mannosamine-6-P Epimerase originated from *Escherichia coli* is generally called as NanE. N-Acetyl-D-Mannosamine-6-P Epimerase originated from various organisms is well known in this field, and may be used in the genetic modification strategy in this Invention. For example, this article describes that N-Acetyl-D-Mannosamine-6-P Epimerase originated from *Escherichia coli* has the nucleic acid sequence codes represented by SEQ ID NO: 28, and the amino acid sequence represented by SEQ ID NO: 29.

The enzyme generally called as "UDP-N-Acetyl-D-Glucosamine-2-Epimerase" in this article catalyzes transformation of UDP-N-Acetyl-D-Glucosamine into N-Acetyl-D-Mannosamine. UDP-N-Acetyl-D-Glucosamine-2-Epimerase originated from *Escherichia coli* is generally called as WecB. UDP-N-Acetyl-D-Glucosamine-2-Epimerase originated from various organisms is well known in this field, and may be used in the genetic modification strategy in this Invention. For example, this article describes that UDP-N-Acetyl-D-Glucosamine-2-Epimerase originated from *Escherichia coli* has the nucleic acid sequence codes represented by SEQ ID NO: 49, and the amino acid sequence represented by SEQ ID NO: 50.

The enzyme generally called as "D-Glucosamine-6-Phosphate Deaminase" in this article catalyzes a reversible reaction of D-Glucosamine-6-Phosphate and water to produce Glucose-6-Phosphate and ammonium. The enzyme is also called as D-Glucosamine-6-Phosphate Epimerase, GlcN6P Deaminase, Phospho-D-GlucosamineEpimerase, Phospho-D-GlucosamineEpimerase, D-Glucosamine Phosphate Ester Deaminase, and 2-Amino-2-Deoxy-D-Glucose-6-Phosphate Ketol Epimerase (deamination). D-Glucosamine-6-Phosphate Deaminase originated from various organisms is well known in this field, and may be used in the genetic modification strategy in this Invention. The enzyme is generally called as NagB in *Escherichia coli* or other bacteria.

The enzyme generally called as "D-Glucosamine-6-Phosphate Synthase" in this article catalyzes Glucose-6-Phosphate and Glutamine to produce D-Glucosamine-6-Phosphate and glutamic acid. The enzyme is also called as D-Glucosamine-Fructose-6-Phosphate Aminotransferase (isomerization), Phosphohexose Aminotransferase, D-Fructose-6-Phosphate Transamidase, D-Glucosamine-6-Phosphate Epimerase (to produce glutamin), L-Glutamine-Fructose-6-Phosphate Transamidase, and GlcN6P Synthase. D-Glucosamine-6-Phosphate Synthase originated from various organisms is well known in this field, and may be used in the genetic modification strategy in this Invention. D-Glucosamine-6-Phosphate Synthase originated from *Escherichia coli* or other bacteria is generally called as GlmS.

The enzyme generally called as "N-Acetyl-D-Glucosamine-6-Phosphate Deacetylase" may hydrolyze N-Acetyl-D-Glucosamine-6-Phosphate into D-Glucosamine-6-Phosphate and acetate ester. N-Acetyl-D-Glucosamine-6-Phosphate Deacetylase originated from various organisms is well known in this field, and may be used in the genetic modification strategy in this Invention. For example, this article describes the enzyme called as NagA, originated from *Escherichia coli*.

The enzyme generally called as "N-Acetylneuraminate Lyase" catalyze degradation of N-Acetyl-D-Mannosamine into N-Acetylneuraminic Acid. N-Acetylneuraminate Lyase originated from various organisms is well known in this field, and may be used in the genetic modification strategy in this Invention. For example, this article describes that N-Acetylneuraminate Lyase originated from *Escherichia coli* is called as NanA.

The enzyme generally called as "PhosphoGlucosamine Mutase" in this article catalyzes transformation of D-Glucosamine-6-Phosphate into D-Glucosamine-1-Phosphate. Phospho-D-Glucosamine Mutase originated from various organisms is well known in this field and may be used in the genetic modification strategy of this Invention. The enzyme PhosphoGlucosamine Mutase is generally called as GlmM in *Escherichia coli* or other bacteria.

The enzyme generally called as "D-Glucosamine-1-PhosphateN-Acetyltransferase" in this article catalyzes transformation of D-Glucosamine-1-Phosphate and Acetyl Coenzyme A into N-Acetyl-D-Glucosamine-1-Phosphate, and release of CoA. As a bifunctional enzyme, it also has the function of N-Acetyl-D-Glucosamine-1-Phosphate Uridyltransferase, and is also called as UDP-N-Acetyl-D-Glucosamine Pyrophosphorylase, UDP-N-Acetyl-D-Glucosamine Diphosphorylase, and catalyze further transformation of N-Acetyl-D-Glucosamine-1-Phosphate into UDP-N-Acetyl-D-Glucosamine. D-Glucosamine-1-PhosphateN-Acetyltransferase and N-Acetyl-D-Glucosamine-1-Phosphate Uridyltransferase originated from various organisms are well known in this field, and may be used in the genetic modification strategy in this Invention. The enzyme is generally called as GlmU in *Escherichia coli* or other bacteria.

Through a crafty design, "Trc promoter" may be used for prokaryotic expression, such as *Escherichia coli* expression system. Trc promoter is well known in this field and may be used in the genetic modification strategy of this Invention. For example, this article describes that Trc promoter has a nucleotide sequence represented by SEQ ID NO: 32.

As disclosed by the WO2004/003175 Invention, D-Glucosamine is very unstable in the common pH range for growth of *Escherichia coli*. D-Glucosamine and/or its degradation products produce toxic effects to the strains. Toxic effects may be evenly observed when D-Glucosamine in a low concentration of up to 20 g/L is preincubated in the culture medium (pH7.0), prior to cell inoculation. Toxic effects are partially caused by the degradation products of D-Glucosamine in the culture medium with an initial pH 7.0. GlcN is more stable in low pH conditions, and D-Glucosamine may not be degraded below pH4.7. However, *Escherichia coli* grow slowly under pH 6-7 conditions. Therefore, the scheme is difficult to implement production of D-Glucosamine in the fermentation tank under relatively low pH.

Based on this this Invention, D-Glucosamine-6-P (GlcN-6-P) is catalyzed by GlmM and GlmU to produce UDP-N-Acetyl-D-Glucosamine (UDP-GlcNAc) in cells, and is catalyzed by UDP-N-Acetyl-Glucosamine-2-Epimerase (WecB) to produce N-Acetyl-D-Mannosamine (ManNAc). Through overexpression of NanK and NanE, they are further transformed into N-Acetyl-D-Glucosamine-6-Phosphate (GlcNAc-6-P), and dephosphorylated under action of phosphatase and then excreted out of cells to produce N-Acetyl-D-Glucosamine (GlcNAc) The method in this Invention may avoid production of D-Glucosamine, and thus avoid toxic effects of D-Glucosamine and/or its degradation products to the strains.

Therefore, the beneficial effects of this Invention lie in: This Invention has demonstrated that natural N-Acetyl-D-Glucosamine may be produced directly by microbial fermentation method; The new production method has no risk for contamination by heavy metals, and no risk for residue of antibiotics or drugs; the production is not influenced by supply of raw materials, and may produce stably for a long term, with high yield and low cost; The produced N-Acetyl-D-Glucosamine and D-Glucosamine products are characterized by non-animal source. The production does not use chitin from shrimp shell, and does use glucose, etc., as carbohydrate source for fermentation. The products are vegetarian products, without any allergens of aquatic products.

The whole contents of the public literatures and references cited or described in this article are attached for reference in this article.

DESCRIPTION FOR ATTACHED FIGURES

FIG. 1, Biosynthesis Strategy and Metabolic Engineering Strategy for N-Acetyl-D-Glucosamine in *Escherichia coli*

ACTUAL IMPLEMENTATION MODES

Hereafter this Invention is further described detailedly in combination with the implementation examples. The following examples are just used as ones to clarify and explain this Invention, and cannot be explained as any limitation to the protection range of this Invention. The technology realized, based on the contents of this Invention, are covered in the protection range of this Invention.

Unless otherwise specified, the raw materials and reagents used in the implementation examples are commercially available goods.

The list of various modified microorganisms involved in and/or described by this Invention is provided below.

| Strain No. | Genotype Description | Remarks |
|---|---|---|
| AT-001 | ATCC 27325, F-IN(rrnD-rrnE)1 lambda-, a prototrophic derivative strain of *Escherichia coli* K-12 | Parent strain of engineering bacterial, obtained from American Type Culture Collection (ATCC) |
| AT-002-01 | AT-001,* manXYZ:: fKanrf | Example 1 |
| AT-002-02 | AT-001,* manXYZ | Example 1 |
| AT-003-01 | AT-002-02,* nanA:: fKanrf | Example 1 |
| AT-003-02 | AT-002-02,* nanA | Example 1 |
| AT-004-01 | AT-003-02,* nagA:: fKanrf | Example 1 |
| AT-004-02 | AT-003-02,* nagA | Example 1 |
| AT-005-01 | AT-004-02,* nagE::fKanrf | Example 1 |
| AT-005-02 | AT-004-02,* nagE | Example 1 |
| AT-006-01 | AT-004-02,* nagE::pTrc-nanK-fKanrf | Example 2 |
| AT-006-02 | AT-004-02,* nagE::pTrc-nanK | Example 2 |
| AT-007-01 | AT-004-02,* nagE::pTrc-nanKM-fKanrf | Example 3 |
| AT-007-02 | AT-004-02,* nagE::pTrc-nanKM | Example 3 |
| AT-008 | AT-007-02,* nanE/pTrc99A | Example 4 |
| AT-009 | AT-007-02, nanE promoter::Trc promoter | Example 4 |

-continued

| Strain No. | Genotype Description | Remarks |
| --- | --- | --- |
| AT-010 | AT-007-02,• nagB promotor::Trc promoter | Example 5 |
| AT-011 | AT-010,• glmS promotor | Example 5 |
| AT-012 | AT-007-02,• glmS promotor::Trc promoter | Example 5 |
| AT-013 | AT-012,• nagB promotor | Example 5 |
| AT-014 | AT-011, nanE/pTrc99A | Example 6 |
| AT-015 | AT-011,• nanE promotor::Trc promoter | Example 6 |
| AT-016 | AT-013, nanE/pTrc99A | Example 6 |
| AT-017 | AT-013,• nanE promotor::Trc promoter | Example 6 |
| AT-018 | AT-007-02, wecB/pTrc99A | Example 7 |
| AT-019 | AT-007-02,• wecB promotor::Trc promoter | Example 7 |
| AT-020 | AT-009, wecB/pTrc99A | Example 8 |
| AT-021 | AT-009,• wecB promotor::Trc promoter | Example 8 |
| AT-022 | AT-011, wecB/pTrc99A | Example 9 |
| AT-023 | AT-011,• wecB promotor::Trc promoter | Example 9 |
| AT-024 | AT-013, wecB/pTrc99A | Example 9 |
| AT-025 | AT-013,• wecB promotor::Trc promoter | Example 9 |
| AT-026 | AT-015, wecB/pTrc99A | Example 10 |
| AT-027 | AT-015,• wecB promotor::Trc promoter | Example 10 |
| AT-028 | AT-017, wecB/pTrc99A | Example 10 |
| AT-029 | AT-017,• wecB promotor::Trc promoter | Example 10 |
| AT-030-01 | AT-004-02,• nagE::pTrc-nanE-fKanrf | Example 13 |
| AT-030-02 | AT-004-02,• nagE::pTrc-nanE | Example 13 |
| AT-031-01 | AT-004-02,• nagE:: pTrc-nanEM-fKanrf | Example 13 |
| AT-031-02 | AT-004-02,• nagE::pTrc-nanEM | Example 13 |
| AT-042-01 | AT-004-02,• nagE::pTrc-wecB-f Kanrf | Example 14 |
| AT-042-02 | AT-004-02,• nagE::pTrc-wecB | Example 14 |
| AT-043-01 | AT-004-02,• nagE::pTrc-wecBM-fKanrf | Example 14 |
| AT-043-02 | AT-004-02,• nagE::pTrc-wecBM | Example 14 |

EXAMPLE 1

This implementation describes construction of a mutant strain of *Escherichia coli*, for which the relevant metabolic pathways for intake of N-Acetyl-D-Glucosamine is blocked and degradation of beneficial intermediate products are blocked.

The said parent strain of the production strain is AT-001 (*Escherichia coli* ATCC 27325), belonging to K-12 derivative strain of *Escherichia coli*, and is obtained from American Type Culture Collection.

Blockage of intake of N-Acetyl-D-Glucosamine into the strain, and of degradation of intermediate products may reduce consumption during metabolism, and increase accumulation of the target product (N-Acetyl-D-Glucosamine).

To construct such mutant host strain, manXYZ, nanA, nagA, and nagE gene sequences in its chromosomal genomes may be deleted completely or partially, to deactivate its function, and thus result in accumulation of N-Acetyl-D-Glucosamine.

Such deletion of gene sequence in the chromosome may be accomplished by Red recombinant technology. Red recombination is an homologous recombination technology, based on Red operon in λ phage, and mediated by RecE/RecT system in Rac phage. By the technology, it may carry out simply and rapidly multiple modifications such as insertion, knockout, and mutation to any large DNA molecules. Simply speaking, for Red recombination technology, pKD46 plasmids with the recombinase-expressing gene are introduced into thalli, then the prepared linear DNA segment for targeting is electrotransformed, positive clones are screened, and finally the resistance gene in the strain is removed.

The specific operational process is described hereafter:

1. Deletion of manXYZ Gene Sequence

Mannose transporter EIIM, P/III$^{man}$ (mannose transporter EIIM, P/III$^{man}$, ManXYZ) may be used as a second transporter of N-Acetyl-D-Glucosamine; it may transport hexose such as N-Acetyl-D-Glucosamine into cells, and thus the target product excreted out of cells and accumulated is transported into cells for degradation. Deletion of manXYZ gene sequence may block transportation of extracellular N-Acetyl-D-Glucosamine into cells for degradation.

(1) Preparation of Linear DNA Full-Length PCR Segment for Targeting of Red Recombination 1) fKanrf Segment Amplified by PCR fKanrf, i.e. FRT-Kanr-FRT segment means a FRT site base sequence for specific recognition of FLP recombinase, mounted at both ends of kalamycin resistance gene (Kanr).

Primer Design: Forward primer (mfKanf-F) SEQ ID No.1, and reverse primer (mfKanf-R) SEQ ID No.2.

Template: pPic9K.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

fKanrf size: 1.28 kb. Its nucleotide sequence is SEQ ID No.3.

The PCR product is separated by 1% agarose gel electrophoresis, and purified to recover the segment.

2) PCR Amplification of Linear DNA Full-Length PCR Segment for Targeting of Red Recombination Design of Homologous Arm Primer: According to the manXYZ sequence SEQ ID No.4, it is designed to delete the homologous arm forward primer (manXYZKO-F) SEQ ID No.5 and reverse primer (manXYZKO-R) SEQ ID No.6 of the manXYZ sequence.

Template: Amplification of fKanrf PCR Segment.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product: Homologous Arm+fKanrf+Homologous Arm.

The PCR product is separated by agarose gel electrophoresis, and purified and recovered to obtain 100 ng/μL linear DNA full-length PCR segment for targeting of Red recombination.

(2) Red Recombination Operation

First, pKD46 carrier is introduced into the AT-001 strain of *Escherichia coli*. Then, the prepared linear DNA segment for targeting is electrotransformed, and positive clones are screened. Finally, the resistance gene is removed.

1) Transformation of pKD46 Plasmid pKD46 carrier is a plasmid with Red recombinase-expressing gene, which is 3-gene segment expressing Exo, Bet, and Gam; the 3 genes are placed below the arabinose promoter, and may express in a large amount by induction of L-arabinose. It is necessary to transform pKD46 plasmid into *Escherichia coli*, to achieve purpose to modify the target gene in the chromosome by Red recombination.

① Preparation of Competence: First, inoculate the bacterial suspension of *Escherichia coli* ATCC 27325 stored at −20° C. into 10 mL of LB broth medium in a ratio of 1:50-100, and shake-cultivate at 37° C. and 225 rpm for 2-3 h. then add the culture solution to a 10-mL centrifuge tube, centrifugate at 4000 g×5 min, discard the supernatant, and suspend with 5 mL 0.1M CaCl$_2$ on an ice bath for 5 min. Finally, centrifugate at 4000 g×5 min, discard the supernatant, and suspend with 5 mL of 0.1M CaCl$_2$ on an ice bath. Allow to stand at −4° C. for 12 h for spontaneous sedimentation. Here, preparation of 0.1M CaCl$_2$: Prepare a 1M CaCl$_2$ solution with anhydrous CaCl$_2$, autoclave at a steam pressure of 15 lbf/in2 for 20 min, and dispense 1.5 mL and store at −20° C.; for use, allow to thaw, and then dilute in a ratio of 1:10 to produce a 0.1M CaCl$_2$ solution.

②Plasmid Transformation: Transfer 250 μL of spontaneously sedimented thalli, add 5 μL of pKD46 plasmid, and cultivate at −4° C. for 30 min. Then heat on a water bath at 42° C. for 1.5 min, add 0.7 mL of SOC medium, and shake at 30° C. for 2 h. Transfer 0.2 mL of the bacterial suspension, and smear on a penicillin plate. Cultivate overnight (for 12-16 h) at 30° C. Pick up monoclone, add 5 mL of LB broth medium and cultivate, and withdraw plasmid for identification. Store the positive strain for use.

2) Electrotransform Linear DNA Segment for Targeting, and Screen Positive Clone

①Preparation of electrotransformed competence: Inoculate the AT-001 strain of Escherichia coli ATCC 27325, containing pKD46, into a test tube of LB medium containing Ampicillin (Amp), and shake-cultivate overnight at 250 rpm; On the next day, inoculate in a ratio of 1% into LB medium containing Amp, and cultivate at 30° C.; when OD$_{600}$ reaches approximately 0.2, add 0.2% L-Arabinose, and induce at 30° C. for 35 min until OD$_{600}$ reaches approximately 0.4. Cool on an ice bath. Wash once with ultrapure water, wash twice with 10% glycerin, and finally resuspend with 10% glycerin; the amount of glycerin used is to produce a final concentration of the thalli concentrated by 500-1000 folds.

②Transformation by electric shock: Take out a 2-mm electrotransformation cup from 70% ethanol, wash with sterilized ultrapure water, and irradiate by UV lamp for 30 min. Precool at 4° C. for 30 min. Transfer 90 μL of finally resuspended cells to a precooled centrifuge tube, add 5 μL (more than 100 ng) of the full-length PCR segment (linear DNA) obtained in Step (1), suction gently by a gun, and maintain on an ice bath for 30 min. Electrotransformation Parameters: 2500V, 200Ω, 25 μF.

③Resuscitate and screen positive clones: add 1 mL of LB broth medium, and cultivate at 37° C. and 100 rpm for 1 h. Then smear one kanamycin (Kan) plate with every 200 μL, 5 plates in total. Smear evenly and allow to air-dry. Cultivate at 30° C. for 24 h. Pick up clones grown under kanamycin resistance, and carry out PCR identification to screen positive clones.

No. of the obtained strain: AT-002-01 (AT-001, ▸manXYZ::fKanrf).

(3) Removal of the Resistance Gene

To facilitate subsequent work, the resistance gene in the obtained strain (positive clones) may be removed. Removal of the resistance gene may be accomplished by pCP20 plasmid. pCP20 is a plasmid with ampicillin and chloramphenicol resistance genes, and may express FLP recombinase after thermal induction, which may identify specifically FRT sites. The sequence between FRT sites may be deleted by recombination, to retain only one FRT site.

Introduce pCP20 into the above kanamycin-resistant clones, cultivate at 30° C. for 8 h, then increase to 42° C. and cultivate overnight, and thermally induce to express FLP recombinase; the plasmids are lost gradually. Streak the plate of antibiotics-free culture medium by an inoculating loop dipped in the bacterial suspension, pick up grown monoclones and dot on the kanamycin-resistant plate; those that cannot grown are clones of which the kanamycin resistance gene has been removed by FLP recombination. Carry out PCR with identification primer to identify clones losing kanamycin resistance.

No. of the obtained strain: AT-002-02 (AT-001, ▸manXYZ).

2. Deletion of nanA Gene Sequence

N-Acetylneuraminate Lyase (N-acetylneuraminate lyase, NanA) can degrade N-Acetyl-D-Mannosamine (ManNAc) in microorganism to produce N-Acetyl-D-Neuraminic Acid (Neu5Ac). Deletion of the nanA gene sequence in nanKETA operon may block degradation of N-Acetyl-D-Mannosamine (ManNAc) into N-Acetyl-D-Neuraminic Acid (Neu5Ac).

(1) Preparation of Linear DNA Full-Length PCR Segment for Targeting of Red Recombination Design of Homologous Arm Primer: According to the nanA sequence SEQ ID No.7 in the former segment of nanE-nanK, the homologous arm primers for deletion of nanA sequence are designed: Forward primer (nanAKO-F) SEQ ID No.8 and reverse primer (nanAKO-R) SEQ ID No.9.

Template: Amplification of fKanrf PCR Segment.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product: Homologous Arm+fKanrf+Homologous Arm.

The PCR product is separated by agarose gel electrophoresis, and purified and recovered to obtain 100 ng/μL linear DNA full-length PCR segment for targeting of Red recombination.

(2) Red Recombination Operation

First, pKD46 carrier is introduced into the AT-002-02 strain of Escherichia coli. Then, the prepared linear DNA segment for targeting is electrotransformed, and positive clones are screened. Finally, the resistance gene is removed.

1) Transformation of pKD46 Plasmid

①Preparation of Competence: First, inoculate the bacterial suspension of Escherichia coli AT-002-02 (AT-001, ▸manXYZ) stored at −20° C. into 10 mL of LB broth medium in a ratio of 1:50-100, and shake-cultivate at 37° C. and 225 rpm for 2-3 h. then add the culture solution to a 10-mL centrifuge tube, centrifugate at 4000 g×5 min, discard the supernatant, and suspend with 5 mL 0.1M CaCl$_2$ on an ice bath for 5 min. Finally, centrifugate at 4000 g×5 min, discard the supernatant, and suspend with 5 mL of 0.1M CaCl$_2$ on an ice bath. Allow to stand at −4° C. for 12 h for spontaneous sedimentation.

②Plasmid Transformation: Transfer 250 μL of spontaneously sedimented thalli, add 5 μL of pKD46 plasmid, and cultivate at −4° C. for 30 min. Then heat on a water bath at 42° C. for 1.5 min, add 0.7 mL of SOC medium, and shake at 30° C. for 2 h. Transfer 0.2 mL of the bacterial suspension, and smear on a penicillin plate. Cultivate overnight (for 12-16 h) at 30° C. Pick up monoclone, add 5 mL of LB broth medium and cultivate, and withdraw plasmid for identification. Store the positive strain for use.

2) Electrotransform Linear DNA Segment for Targeting, and Screen Positive Clone

①Preparation of Electrotransformed Competence: Inoculate the AT-002-02 strain of Escherichia coli, containing pKD46, into a test tube of LB medium containing Ampicillin (Amp), and shake-cultivate at 250 rpm. On the next day, inoculate in a ratio of 1% into LB medium containing Amp, and cultivate at 30° C.; when OD$_{600}$ reaches approximately 0.2, add 0.2% L-Arabinose, and induce at 30° C. for 35 min until OD$_{600}$ reaches approximately 0.4. Cool on an ice bath. Wash once with ultrapure water, wash twice with 10% glycerin, and finally resuspend with 10% glycerin; the amount of glycerin used is to produce a final concentration of the thalli concentrated by 500-1000 folds.

② Transformation by electric shock: Take out a 2-mm electrotransformation cup from 70% ethanol, wash with sterilized ultrapure water, and irradiate by UV lamp for 30 min. Precool at 4° C. for 30 min. Transfer 90 µL of finally resuspended cells to a precooled centrifuge tube, add 5 µL (more than 100 ng) of the full-length PCR segment (linear DNA) obtained in Step (1), suction gently by a gun, and maintain on an ice bath for 30 min. Electrotransformation Parameters: 2500V, 200Ω, 25 µF.

③ Resuscitate and screen positive clones: add 1 mL of LB broth medium, and cultivate at 37° C. and 100 rpm for 1 h. Then smear one kanamycin (Kan) plate with every 200 µL, 5 plates in total. Smear evenly and allow to air-dry. Cultivate at 30° C. for 24 h. Pick up clones grown under kanamycin resistance, and carry out PCR identification to screen positive clones.

No. of the obtained strain: AT-003-01 (AT-002-02, ▸nanA::fKanrf).

(3) Removal of the Resistance Gene

Introduce pCP20 into the above kanamycin-resistant clones, cultivate at 30° C. for 8 h, then increase to 42° C. and cultivate overnight, and thermally induce to express FLP recombinase; the plasmids are lost gradually. Streak the plate of antibiotics-free culture medium by an inoculating loop dipped in the bacterial suspension, pick up grown monoclones and dot on the kanamycin-resistant plate; those that cannot grown are clones of which the kanamycin resistance gene has been removed by FLP recombination. Carry out PCR with identification primer to identify clones losing kanamycin resistance.

No. of the obtained strain: AT-003-02 (AT-002-02, ▸nanA).

3. Deletion of nagA Gene Sequence

N-Acetyl-D-Glucosamine-6-Phosphate Deacetylase (NagA) can transform N-Acetyl-D-Glucosamine-6-Phosphate (GlcNAc-6-P) in microorganism into D-Glucosamine-6-Phosphate (GlcN-6-P). Deletion of nagA gene sequence in nag operon (nagE-nagBACD) may block transformation of N-Acetyl-D-Glucosamine-6-Phosphate (GlcNAc-6-P) into D-Glucosamine-6-Phosphate (GlcN-6-P).

(1) Preparation of Linear DNA Full-Length PCR Segment for Targeting of Red Recombination Design of Homologous Arm Primers: From NCBI, look up NC_000913, nagA sequence SEQ ID No.10 for N-Acetyl-D-Glucosamine-6-Phosphate Deacetylase, *Escherichia coli* str.K-12, design the homologous arm primers for deletion of nagA sequence: Forward primer (nagAKO-F) SEQ ID No.11 and reverse primer (nagAKO-R) SEQ ID No.12.

Template: Amplification of fKanrf PCR Segment.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product: Homologous Arm+fKanf+Homologous Arm.

The PCR product is separated by agarose gel electrophoresis, and purified and recovered to obtain 100 ng/µL linear DNA full-length PCR segment for targeting of Red recombination.

(2) Red Recombination Operation

First, pKD46 carrier is introduced into the AT-003-02 strain of *Escherichia coli*. Then, the prepared linear DNA segment for targeting is electrotransformed, and positive clones are screened. Finally, the resistance gene is removed.

1) Transformation of pKD46 Plasmid

① Preparation of Competence: First, inoculate the bacterial suspension of *Escherichia coli* AT-003-02 (AT-002-02, ▸nanA) stored at −20° C. into 10 mL of LB broth medium in a ratio of 1:50-100, and shake-cultivate at 37° C. and 225 rpm for 2-3 h. then add the culture solution to a 10-mL centrifuge tube, centrifugate at 4000 g×5 min, discard the supernatant, and suspend with 5 mL 0.1M $CaCl_2$ on an ice bath for 5 min. Finally, centrifugate at 4000 g×5 min, discard the supernatant, and suspend with 5 mL of 0.1M $CaCl_2$ on an ice bath. Allow to stand at −4° C. for 12 h for spontaneous sedimentation.

② Plasmid Transformation: Transfer 250 µL of spontaneously sedimented thalli, add 5 µL of pKD46 plasmid, and cultivate at −4° C. for 30 min. Then heat on a water bath at 42° C. for 1.5 min, add 0.7 mL of SOC medium, and shake at 30° C. for 2 h. Transfer 0.2 mL of the bacterial suspension, and smear on a penicillin plate. Cultivate overnight (for 12-16 h) at 30° C. Pick up monoclone, add 5 mL of LB broth medium and cultivate, and withdraw plasmid for identification. Store the positive strain for use.

2) Electrotransform Linear DNA Segment for Targeting, and Screen Positive Clone

① Preparation of Electrotransformed Competence: Inoculate the AT-003-02 strain of *Escherichia coli*, containing pKD46, into a test tube of LB medium containing Ampicillin (Amp), and shake-cultivate at 250 rpm, on the next day, inoculate in a ratio of 1% into LB medium containing Amp, and cultivate at 30° C.; when $OD_{600}$ reaches approximately 0.2, add 0.2% L-Arabinose, and induce at 30° C. for 35 min until $OD_{600}$ reaches approximately 0.4. Cool on an ice bath. Wash once with ultrapure water, wash twice with 10% glycerin, and finally resuspend with 10% glycerin; the amount of glycerin used is to produce a final concentration of the thalli concentrated by 500-1000 folds.

② Transformation by electric shock: Take out a 2-mm electrotransformation cup from 70% ethanol, wash with sterilized ultrapure water, and irradiate by UV lamp for 30 min. Precool at 4° C. for 30 min. Transfer 90 µL of finally resuspended cells to a precooled centrifuge tube, add 5 µL (more than 100 ng) of the full-length PCR segment (linear DNA) obtained in Step (1), suction gently by a gun, and maintain on an ice bath for 30 min. Electrotransformation Parameters: 2500V, 200Ω, 25 µL.

③ Resuscitate and screen positive clones: add 1 mL of LB broth medium, and cultivate at 37° C. and 100 rpm for 1 h. Then smear one kanamycin (Kan) plate with every 200 µL, 5 plates in total. Smear evenly and allow to air-dry. Cultivate at 30° C. for 24 h. Pick up clones grown under kanamycin resistance, and carry out PCR identification to screen positive clones.

No. of the obtained strain: AT-004-01 (AT-003-02, ▸nagA::fKanrf).

(3) Removal of the Resistance Gene

Introduce pCP20 into the above kanamycin-resistant clones, cultivate at 30° C. for 8 h, then increase to 42° C. and cultivate overnight, and thermally induce to express FLP recombinase; the plasmids are lost gradually. Streak the plate of antibiotics-free culture medium by an inoculating loop dipped in the bacterial suspension, pick up grown monoclones and dot on the kanamycin-resistant plate; those that cannot grown are clones of which the kanamycin resistance gene has been removed by FLP recombination. Carry out PCR with identification primer to identify clones losing kanamycin resistance.

No. of the obtained strain: AT-004-02 (AT-003-02, ▸nagA).

4. Deletion of nagE Gene Sequence

Deletion of the gene sequence nagE for N-Acetyl-D-Glucosamine Specific Enzyme II$^{Nag}$ (NagE) may block transport of extracellular GlcNAc into cells for degradation.

(1) Preparation of Linear DNA Full-Length PCR Segment for Targeting of Red Recombination Design of Homologous Arm Primers: From NCBI, look up NC_000913, NagB promoter and nagA gene sequence SEQ ID No.13, *Escherichia coli* str.K-12, design the homologous arm primers for deletion of nagA sequence: Forward primer (nagEKO-F1) SEQ ID No.14 and reverse primer (nagEKO-R1) SEQ ID No.15.

Template: Amplification of fKanrf PCR Segment.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product: Homologous Arm+fKanrf+Homologous Arm.

The PCR product is separated by agarose gel electrophoresis, and purified and recovered to obtain 100 ng/μL linear DNA full-length PCR segment for targeting of Red recombination.

(2) Red Recombination Operation

First, pKD46 carrier is introduced into the AT-004-02 strain of *Escherichia coli*. Then, the prepared linear DNA segment for targeting is electrotransformed, and positive clones are screened. Finally, the resistance gene is removed.

1) Transformation of pKD46 Plasmid

① Preparation of Competence: First, inoculate the bacterial suspension of *Escherichia coli* AT-004-02 (AT-003-02, nagA) stored at −20° C. into 10 mL of LB broth medium in a ratio of 1:50-100, and shake-cultivate at 37° C. and 225 rpm for 2-3 h. then add the culture solution to a 10-mL centrifuge tube, centrifugate at 4000 g×5 min, discard the supernatant, and suspend with 5 mL 0.1M CaCl$_2$ on an ice bath for 5 min. Finally, centrifugate at 4000 g×5 min, discard the supernatant, and suspend with 5 mL of 0.1M CaCl$_2$ on an ice bath. Allow to stand at −4° C. for 12 h for spontaneous sedimentation.

② Plasmid Transformation: Transfer 250 μL of spontaneously sedimented thalli, add 5 μL of pKD46 plasmid, and cultivate at −4° C. for 30 min. Then heat on a water bath at 42° C. for 1.5 min, add 0.7 mL of SOC medium, and shake at 30° C. for 2 h. Transfer 0.2 mL of the bacterial suspension, and smear on a penicillin plate. Cultivate overnight (for 12-16 h) at 30° C. Pick up monoclone, add 5 mL of LB broth medium and cultivate, and withdraw plasmid for identification. Store the positive strain for use.

2) Electrotransform Linear DNA Segment for Targeting, and Screen Positive Clone

① Preparation of Electrotransformed Competence: Inoculate the AT-004-02 strain of *Escherichia coli*, containing pKD46, into a test tube of LB medium containing Ampicillin (Amp), and shake-cultivate at 250 rpm. On the next day, inoculate in a ratio of 1% into LB medium containing Amp, and cultivate at 30° C.; when OD$_{600}$ reaches approximately 0.2, add 0.2% L-Arabinose, and induce at 30° C. for 35 min until OD$_{600}$ reaches approximately 0.4. Cool on an ice bath. Wash once with ultrapure water, wash twice with 10% glycerin, and finally resuspend with 10% glycerin; the amount of glycerin used is to produce a final concentration of the thalli concentrated by 500-1000 folds.

② Transformation by electric shock: Take out a 2-mm electrotransformation cup from 70% ethanol, wash with sterilized ultrapure water, and irradiate by UV lamp for 30 min. Precool at 4° C. for 30 min. Transfer 90 μL of finally resuspended cells to a precooled centrifuge tube, add 5 μL (more than 100 ng) of the full-length PCR segment (linear DNA) obtained in Step (1), suction gently by a gun, and maintain on an ice bath for 30 min. Electrotransformation Parameters: 2500V, 200Ω, 25 μF.

③ Resuscitate and screen positive clones: add 1 mL of LB broth medium, and cultivate at 37° C. and 100 rpm for 1 h. Then smear one kanamycin (Kan) plate with every 200 μL, 5 plates in total. Smear evenly and allow to air-dry. Cultivate at 30° C. for 24 h. Pick up clones grown under kanamycin resistance, and carry out PCR identification to screen positive clones.

No. of the obtained strain: AT-005-01 (AT-004-02, ▸nagE::fKanrf).

(3) Removal of the Resistance Gene

Introduce pCP20 into the above kanamycin-resistant clones, cultivate at 30° C. for 8 h, then increase to 42° C. and cultivate overnight, and thermally induce to express FLP recombinase; the plasmids are lost gradually. Streak the plate of antibiotics-free culture medium by an inoculating loop dipped in the bacterial suspension, pick up grown monoclones and dot on the kanamycin-resistant plate; those that cannot grown are clones of which the kanamycin resistance gene has been removed by FLP recombination. Carry out PCR with identification primer to identify clones losing kanamycin resistance.

No. of the obtained strain: AT-005-02 (AT-004-02, ▸nagE).

EXAMPLE 2

This example describes gene nanK cloning of N-Acetyl-D-Mannosamine Kinase (NanK), and transformed nanK/pTrc99A plasmids in *Escherichia coli*, as well as integration of ptrc-nanK gene cassette into the chromosome of *Escherichia coli*.

1. nanK Gene Cloning, Transformation of nanK/pTrc99A Plasmid in *Escherichia coli*, and its Influence on Output of N-Acetyl-D-Glucosamine Amplification of the gene nanK of *Escherichia coli* NanK (N-acetylmannosamine kinase, N-Acetyl-D-Mannosamine Kinase), that is controlled by Trc promoter to transform the strain for overexpression of the enzyme, may strengthen phosphorylation of ManNAc (N-Acetyl-D-mannosamine, N-Acetyl-D-Mannosamine or N-Acetyl-D-Mannosamine) into ManNAc-6-P (N-Acetyl-D-mannosamine-6-P, N-Acetyl-D-Mannosamine-6-Phosphate).

1) nanK Gene Cloning of *Escherichia coli*

From NCBI, look up U00096, to obtain the nucleotide sequence SEQ ID No.16 of the nanK gene of *Escherichia coli*, which amino acid sequence is SEQ ID No.17.

Primer Design: Forward primer (nanK-F) SEQ ID No.18 and reverse primer (nanK-R) SEQ ID No.19.

Template: *Escherichia coli* AT-001.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product Size: 0.9 kb.

The PCR product is separated by 1% agarose gel electrophoresis, and purified to recover the segment.

Connect the obtained PCR amplification segment with pUC57-T carrier, and carry out sequencing for identification, to obtain nanK/pUC57.

2) Construction and Transformation of Plasmid in which nanK Gene is Controlled by Trc Promoter ① Plasmid Construction: Amplify plasmid nanK/pUC57, digest enzymatically nanK/pUC57 and carrier pTrc99A with Nco I and Hind III, separate by agarose gel electrophoresis, purify to recover nanK segment and pTrc99A segment, connect overnight with T4 DNA ligase at 16° C., and carry out identification to obtain nanK/pTrc99A plasmid.

② Preparation of Competence: First, inoculate the bacterial suspension of AT-005-02 stored at −20° C. into 10 mL of LB broth medium in a ratio of 1:50-100, and shake-cultivate at 37° C. and 225 rpm for 2-3 h. then add the culture solution to a 10-mL centrifuge tube, centrifugate at 4000 g×5 min, discard the supernatant, and suspend with 5 mL 0.1M $CaCl_2$ on an ice bath for 5 min. Finally, centrifugate at 4000 g×5 min, discard the supernatant, and suspend with 5 mL of 0.1M $CaCl_2$ on an ice bath. Allow to stand at −4° C. for 12 h for spontaneous sedimentation.

③ Plasmid Transformation: Transfer 250 μL of spontaneously sedimented thalli, add 5 μL of nanK/pTrc99A plasmid, and cultivate at −4° C. for 30 min. Then heat on a water bath at 42° C. for 1.5 min, add 0.7 mL of SOC medium, and shake at 30° C. for 2 h. Transfer 0.2 mL of the bacterial suspension, and smear on a penicillin plate. Cultivate overnight (for 12-16 h) at 30° C. Pick up monoclone, add 5 mL of LB broth medium and cultivate, and withdraw plasmid for identification. Store the positive strain for use. Obtain Recombinant Strain nanK/pTrc99A (AT-005-02)

3) Influence of nanK/pTrc99A Plasmid Transformation on the Output of N-Acetyl-D-Glucosamine Carry out shake-flask fermentation trial with the recombinant strain and nanK/pTrc99A (AT-005-02) reference strain. Transfer the monoclonal strain freshly cultivated in culture medium of the LB plate, inoculate into a test tube (13×150 mm) containing 3 mL of the LB broth culture medium, and shake-cultivate at 30° C. for 8 h. Components of LB Broth Medium: 5 g/L yeast powder, 10 g/L peptone, and 10 g/L NaCl. Then transfer the seed culture solution, inoculate in 3% into a 250-mL shake-flask containing 50 mL of the fermentation culture solution (M9 culture solution). The initial $OD_{600}$ is approximately 0.5; shake-cultivate at 37° C. and 225 rpm. The fermentation cycle is 72 h. At 24 h and 48 h, adjust to pH 7.0 with 10M NaOH. According to glucose consumption in the fermentation broth, add 65% glucose solution to maintain a glucose concentration of 20 g/L. After completion of fermentation, transfer 1 mL of the fermentation broth and centrifugate. Measure the content of N-Acetyl-D-Glucosamine by HPLC method.

① HPLC Method to Measure the Content of N-Acetyl-D-Glucosamine

Buffer: Add 3.5 g of dipotassium hydrogen phosphate to 1-L volumetric flask, add water to dissolve, add 0.25 mL of 0.25 mL of ammonia water, then dilute with water and mix well, adjust to pH 7.5, and add water to volume.

Mobile Phase: Acetonitrile:Buffer (75:25).

Diluent: Acetonitrile and water (50:50).

Standard Solution: Dissolve 1.0 mg/mL USP N-Acetyl-D-Glucosamine Reference Substance (RS) in the diluent.

Sample Solution: Dissolve 1.0 mg/mL N-Acetyl-D-Glucosamine sample in the diluent.

Liquid Phase Conditions:

Model: LC

Detector: UV 195 nm

Chromatographic Column: 4.6-mm×15-cm; 3-μm packing L8

Flow Rate: 1.5 mL/min

Column Temperature: 35° C.

Injection Volume: 10 μL

② Preparation of M9 Culture Solution

First prepare 5×M9 culture medium: To approximately 800 mL of double distilled water ($ddH_2O$), add 64 g of $Na_2HPO_4 \cdot 7H_2O$, 15 g of $KH_2PO_4$, 2.5 g of NaCl, and 5.0 g of $NH_4Cl$, and after dissolution, add water to 1000 mL. Sterilize at 121° C. for 30 min. Then prepare 1M $MgSO_4$, 1M $CaCl_2$, and 20% glucose, respectively, and sterilize them separately. Then prepare M9 culture solution according to Table 1, while 1000× microelement solution is prepared according to Table 2.

TABLE 1

Components of M9 Culture Solution

| Ingredients | Amount used (mL/L) |
| --- | --- |
| 5×M9 | 200 |
| 1M $MgSO_4$ | 2 |
| 1M $CaCl_2$ | 0.1 |
| 20% Glucose | 20 |
| 1000× Microelement Solution | 1 |
| $ddH_2O$ | to 1000 |
| pH | 6.9 |

TABLE 2

Components of 1000× Microelement Solution

| Ingredients | Amount used (g/L) |
| --- | --- |
| $CoCl_2 \cdot 6H_2O$ | 0.01 |
| $CuSO_4 \cdot 5H_2O$ | 0.01 |
| $MnSO_4 \cdot H_2O$ | 0.033 |
| $FeSO_4 \cdot 7H_2O$ | 0.50 |
| $ZnSO_4 \cdot 7H_2O$ | 0.38 |
| $H_3BO_3$ | 0.01 |
| $NaMoO_4 \cdot 2H_2O$ | 0.01 |
| pH | 3 |

③ Influence of nanK/pTrc99A Plasmid Transformation on the Output of N-Acetyl-D-Glucosamine from Shake-Flask Fermentation See Table 3 for the output from shake-flask fermentation. The results show that: The output by the reference strain AT-005-02 is very low and is not detected, while the output from overexpression by nanK gene of nanK/pTrc99A (AT-005-02), controlled by Trc promoter, is increased obviously.

TABLE 3

Output from Shake-flask Fermentation by the Recombinant nanK/pTrc99A (AT-005-02)

| species | Output of N-Acetyl-D-Glucosamine (g/L) |
| --- | --- |
| AT-005-02 (AT-004-02, nagE) (Reference) | Not detected |
| NanK/pTrc99A (AT-005-02) | 2.9 ± 0.4 |

2. Integration of pTrc-nanK Gene Cassette into the Chromosome of *Escherichia coli*

Using the nagE gene site as integration site of pTrc-nanK gene cassette into the chromosome. To achieve integration of pTrc-nanK gene cassette into the chromosome of *Escherichia coli*, first amplify the nanK segment pTrc-nanK of Trc promoter, as well as the kanamycin resistance gene segment with FLP recognition site (FRT site) at its both ends: FRT-Kanr-FRT (fKanrf), and splice them. Then design homologous primers for deletion of the nagE gene sequence, and using the spliced segment of pTrc-nanK and fKanrf as template, amplify the linear DNA full-length segment for targeting of Red recombination.

The specific operating process is provided below:

(1) PCR Amplification of pTrc-nanK Segment

Template: nanK/pTrc99A.

Primer Design: Forward primer (Trcff-F) SEQ ID No.20, and reverse primer (Trcff-R) SEQ ID No.21.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Produce Size: 1.05 kb.

The PCR product is separated by 1% agarose gel electrophoresis, and purified to recover the segment.

(2) fKanrf Segment Amplified by PCR

Primer Design: Forward primer (mfKanf-F) SEQ ID No.1, and reverse primer (mfKanf-R) SEQ ID No.2.

Template: pPic9K.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

fKanrf size: 1.28kb. Its nucleotide sequence is SEQ ID No.3.

The PCR product is separated by 1% agarose gel electrophoresis, and purified to recover the segment.

(3) Amplification of fKanrf Spliced with pTrc-nanK

Primer Design: Forward primer (fKanf-F) SEQ ID No.22, and reverse primer (fKanf-R) SEQ ID No.23.

Template: fKanrf.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

fKanrf size from secondary amplification: 1.3 kb.

The PCR product is separated by 1% agarose gel electrophoresis, and purified to recover the segment.

(4) Preparation of Linear DNA Full-length PCR Segment for Targeting of Red Recombination Design of Homologous Arm Primers: Design again homologous arm primers for deletion of the nagE gene sequence: Forward primer (nagEKO-F2) SEQ ID No.24, and reverse primer (nagEKO-R2) SEQ ID No.25.

Template: Mix pTrc-nanK PCR segment, and fKanrf PCR segment from secondary amplification in the ratio of 1:1.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product: Homologous Arm+pTrc-nanK-fKanrf+Homologous Arm

The PCR product is separated by agarose gel electrophoresis, and purified and recovered to obtain 100 ng/μL linear DNA full-length PCR segment for targeting of Red recombination.

(5) Red Recombination Operation

First, pKD46 carrier is introduced into the AT-004-02 strain of *Escherichia coli*. Then, the prepared linear DNA segment for targeting is electrotransformed, and positive clones are screened. Finally, the resistance gene is removed.

1) Transformation of pKD46 Plasmid

① Preparation of Competence: First, inoculate the bacterial suspension of *Escherichia coli* AT-004-02 stored at −20° C. into 10 mL of LB broth medium in a ratio of 1:50-100, and shake-cultivate at 37° C. and 225 rpm for 2-3 h. then add the culture solution to a 10-mL centrifuge tube, centrifugate at 4000 g×5 min, discard the supernatant, and suspend with 5 mL 0.1M $CaCl_2$ on an ice bath for 5 min. Finally, centrifugate at 4000 g×5 min, discard the supernatant, and suspend with 5 mL of 0.1M $CaCl_2$ on an ice bath. Allow to stand at −4° C. for 12 h for spontaneous sedimentation.

② Plasmid Transformation: Transfer 250 μL of spontaneously sedimented thalli, add 5 μL of pKD46 plasmid, and cultivate at −4° C. for 30 min. Then heat on a water bath at 42° C. for 1.5 min, add 0.7 mL of SOC medium, and shake at 30° C. for 2 h. Transfer 0.2 mL of the bacterial suspension, and smear on a penicillin plate. Cultivate overnight (for 12-16 h) at 30° C. Pick up monoclone, add 5 mL of LB broth medium and cultivate, and withdraw plasmid for identification. Store the positive strain for use.

2) Electrotransform Linear DNA Segment for Targeting, and Screen Positive Clone

① Cool on an ice bath. Wash once with ultrapure water, wash twice with 10% glycerin, and finally resuspend with 10% glycerin; the amount of glycerin used is to produce a final concentration of the thalli concentrated by 500-1000 folds.

② Transformation by electric shock: Take out a 2-mm electrotransformation cup from 70% ethanol, wash with sterilized ultrapure water, and irradiate by UV lamp for 30 min. Precool at 4° C. for 30 min. Transfer 90 μL of finally resuspended cells to a precooled centrifuge tube, add 5 μL (more than 100 ng) of the full-length PCR segment (linear DNA) obtained in Step (4), suction gently by a gun, and maintain on an ice bath for 30 min. Electrotransformation Parameters: 2500V, 200Ω, 25 μF.

③ Resuscitate and screen positive clones: add 1 mL of LB broth medium, and cultivate at 37° C. and 100 rpm for 1 h. Then smear one kanamycin (Kan) plate with every 200 μL, 5 plates in total. Smear evenly and allow to air-dry. Cultivate at 30° C. for 24 h. Pick up clones grown under kanamycin resistance, and carry out PCR identification to screen positive clones.

No. of the obtained strain: AT-006-01 (AT-004-02, ·nagE::pTrc-nanK-fKanrf).

(6) Removal of the Resistance Gene

Introduce pCP20 into the above kanamycin-resistant clones, cultivate at 30° C. for 8 h, then increase to 42° C. and cultivate overnight, and thermally induce to express FLP recombinase; the plasmids are lost gradually. Streak the plate of antibiotics-free culture medium by an inoculating loop dipped in the bacterial suspension, pick up grown monoclones and dot on the kanamycin-resistant plate; those that cannot grown are clones of which the kanamycin resistance gene has been removed by FLP recombination. Carry out PCR with identification primer to identify clones losing kanamycin resistance.

No. of the obtained strain: AT-006-02 (AT-004-02, ·nagE::pTrc-nanK).

3. Influence of pTrc-nanK Gene Cassette Integration on the Output of N-Acetyl-D-Glucosamine Carry out a shake-flask fermentation trial with the recombinant strain AT-006-02 of which the nagE gene site in the chromosome is integrated with pTrc-nanK gene cassette, and the reference strain. Transfer the monoclonal strain freshly cultivated in culture medium of the LB plate, inoculate into a test tube (13×150 mm) containing 3 mL of the LB broth culture medium, and shake-cultivate at 30° C. for 8 h. Then transfer the seed culture solution, inoculate in 3% into a 250-mL shake-flask containing 50 mL of the fermentation culture solution (M9 culture solution). The initial $OD_{600}$ is approximately 0.5; shake-cultivate at 37° C. and 225 rpm. The fermentation cycle is 72 h. At 24 h and 48 h, adjust to pH 7.0 with 10M NaOH. According to glucose consumption in the fermentation broth, add 65% glucose solution to maintain a glucose concentration of 20 g/L. After completion of fermentation, transfer 1 mL of the fermentation broth and centrifugate. Measure the content of N-Acetyl-D-Glucosamine by HPLC method.

See Table 4 for the output from shake-flask fermentation. The results show that: The outputs by the reference strains AT-001 and AT-005-02 are very low and are not detected, while the output by the recombinant strain integrated with pTrc-nanK gene cassette is increased obviously, and is also increased significantly than that by the recombinant strain nanK/pTrc99A (AT-005-02) not integrated.

TABLE 4

Output from Shake-flask Fermentation by the Recombinant Strain integrated with pTrc-nanK Gene Cassette

| species | Output of N-Acetyl-D-Glucosamine (g/L) |
|---|---|
| AT-001 (Reference) | Not detected |
| AT-005-02 (AT-004-02,˙ nagE) (Reference) | Not detected |
| nanK/pTrc99A(AT-005-02) | 2.8 ± 0.5 |
| AT-006-02 (AT-004-02,˙ nagE::pTrc-nanK) | 4.2 ± 0.5 |

EXAMPLE 3

This implementation example describes screening for a gene mutant of N-Acetyl-D-Mannosamine Kinase (NanK); the said gene encodes N-Acetyl-D-Mannosamine Kinase (NanK) with increased activities.

To further increase synthetic quantity of N-Acetyl-D-Glucosamine by the production strain, screen a gene mutant encoding N-Acetyl-D-Mannosamine Kinase (NanK) with increased activities. To achieve the purpose, amplify the cloned gene by error-prone PCR technology; used for amplified DNA polymerase, amplify the said gene under conditions leading to high-frequency mismatch, so as to obtain a high-frequency mutation in PCR products.

The specific operating process is provided below:

1. Amplification of the Gene nanK of N-Acetyl-D-Mannosamine Kinase in *Escherichia coli* by Error-Prone PCR By means of Taq DNA polymerase without the property of 3'-5' proofreading function, control the frequency of random mutation under high magnesium ion concentration (8 mmol/L) and different dNTP concentrations (where, the concentration of dATP and dGTP is 1.5 mmol/L; and the concentration of dTTP and dCTP is 3.0 mmol/L), introduce random mutations into the target gene, and construct a mutant library; The template concentration A260 value is 1000 ng/mL, the enzyme concentration is 5 U/μL, and the primer concentration is 100 μM.

Error-prone PCR reaction system (50 μL): 10×PCR reaction buffer 5 μl, dNTP (22.5 mM) 5 μL, $MgCl_2$ (2.5 mM) 5 μL, Forward primer (nanK-F, SEQ ID No.18) 1 μL, reverse primer (nanK-R, SEQ ID No.19) 1 μL, DNA template (nanK/pUC57) 0.1 μL, Taq DNA polymerase 0.5 μL, and $ddH_2O$ 32.4 μL.

PCR procedure: Predegenerate at 96° C. for 4 min; degenerate at 94° C. for 1 min, anneal at 56° C. for 1 min, extend at 75° C. for 2 min, and repeat for 45 cycles; finally extend at 75° C. for 15 min, recover PCR product (product size: 0.9 kb) by gel recovery method; transfer 5 μL of the product and carry out 1% agarose gel electrophoresis test; the product is store at −20° C. for use.

2. Construction of the Gene Mutant Library of N-Acetyl-D-Mannosamine Kinase

Digest the above PCR product by two enzymes of restriction endonuclease Nco I and Hind III, carry out a ligation reaction with pTrc99A digested by Nco I and Hind III, then transform *Escherichia coli* AT-005-02 with the mixture of the ligated products to obtain a large amount of cloned transformants, and construct a mutant library of transformed thalli.

3. Screening for Mutants with High Enzyme Activities

Using the wild type NanK/pTrc99A (AT-005-02) as reference, pick up randomly 300 mutant clones from the mutant library of transformed thalli, inoculate into 5 mL of LB medium containing 50 μg/mL Ampicillin (Amp), shake-cultivate at 37° C. and 150 rpm for 18 h, and then centrifugate at 10000 rpm for 5 mim and collect thalli. Discard the supernatant, then resuspend at 4° C. in 1 mL of PBS solution (pH 7.5, 10 mmol/L), carry out ultrasonicate at a voltage of 300 V for 10 min (ultrasonicate for 3 s and pause for 6 s), centrifugate, transfer the supernatant as crude extract of enzyme, and carry out a method for determination of enzyme activity.

Determination of N-Acetyl-D-Mannosamine Kinase (NanK) Activity: Based on the phosphorylated amount of N-Acetyl-D-Mannosamine (ManNAc); that is to say, using the reduced amount of N-Acetyl-D-Mannosamine as test marker. Definition of Enzyme Activity Unit: Under the enzymatic reaction conditions, the enzyme amount reduced by the reducing sugar, equivalent to 1 μmol N-Acetyl-D-Mannosamine per minute, is defined as one enzyme activity unit (IU). The specific procedure is provided as follows: Transfer 5 mL of the reaction system as the system for determination of enzyme activity, which contains 500 mmol/L N-Acetyl-D-Mannosamine, 5 mmol/L glucose, 100 mmol/L Tris-HCl (pH8.0), and 100 μL of crude enzyme solution. Carry out the reaction for determination of enzyme activity on a water bath at 37° C., maintain for 4 h, and then place the enzymatic hydrolysate at 70° C. for 10 min to stop the reaction. Centrifugate at 3000 rpm for 10 min, and transfer the supernatant. Measure the content of N-Acetyl-D-Mannosamine by HPLC method.

The results show that: The enzyme activity of the mutant strain with maximum activity is 77.5 IU/mL, and the enzyme activity of the reference is 16.3 IU/mL. Transform NanK by error-prone PCR, to obtain a mutant strain with enzyme activity increased by 5 folds. Pick up the mutant strain with maximum enzyme activity and extract plasmids for sequencing. The results show that: The gene sequence of the mutant of N-Acetyl-D-Mannosamine Kinase is shown as SEQ ID No.26, and the corresponding amino acid is shown as SEQ ID No.27. By sequence alignment with the gene sequence of wild the type N-Acetyl-D-Mannosamine Kinase, 4 base point mutations occur in total: 107A/G, 309T/G, 669G/C, and 783A/G; There occur 3 missense mutations of amino acids, of which the mutation points are: Q36R (glutamine at Site 36 is replaced by arginine), I103M (isoleucine at Site 103 is replaced by methionine), and R223S (arginine at Site 223 is replaced by serine) The mutant gene is named as nanKM.

4. Integration of pTrc-nanK Gene Cassette into the nagE Gene Site in the Chromosome of *Escherichia coli*

Using the nagE gene site as integration site of pTrc-nanKM gene cassette into the chromosome. To achieve integration of pTrc-nanKM gene cassette into the chromosome of *Escherichia coli*, first amplify the nanK segment pTrc-nanKM of Trc promoter, as well as the kanamycin resistance gene segment with FLP recognition site (FRT site) at its both ends: FRT-Kanr-FRT (fKanrf), and splice them. Then design homologous primers for deletion of the nagE gene sequence, and using the spliced segment of pTrc-nanKM and fKanrf as template, amplify the linear DNA full-length segment for targeting of Red recombination.

The specific operating process is provided below:

(1) PCR Amplification of pTrc-nanKM Segment

Template: nanKM/pTrc99A.

Primer Design: Forward primer (Trcff-F) SEQ ID No.20, and reverse primer (Trcff-R) SEQ ID No.21.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Produce Size: 1.05kb.

The PCR product is separated by 1% agarose gel electrophoresis, and purified to recover the segment.

(2) fKanrf Segment Amplified by PCR

Primer Design: Forward primer (mfKanf-F) SEQ ID No.1, and reverse primer (mfKanf-R) SEQ ID No.2.

Template: pPic9K.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

fKanrf size: 1.28kb. Its nucleotide sequence is SEQ ID No.3.

The PCR product is separated by 1% agarose gel electrophoresis, and purified to recover the segment.

(3) Amplification of fKanrf Spliced with pTrc-nanKM

Primer Design: Forward primer (fKanf-F) SEQ ID No.22, and reverse primer (fKanf-R) SEQ ID No.23.

Template: fKanrf.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

fKanrf size from secondary amplification: 1.3 kb.

The PCR product is separated by 1% agarose gel electrophoresis, and purified to recover the segment.

(4) Preparation of Linear DNA Full-length PCR Segment for Targeting of Red Recombination Design of Homologous Arm Primers: Design again homologous arm primers for deletion of the nagE gene sequence: Forward primer (nagEKO-F2) SEQ ID No.24, and reverse primer (nagEKO-R2) SEQ ID No.25.

Template: Mix pTrc-nanKM PCR segment, and fKanrf PCR segment from secondary amplification in the ratio of 1:1.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product: Homologous Arm+pTrc-nanKM-fKanrf+Homologous Arm

The PCR product is separated by agarose gel electrophoresis, and purified and recovered to obtain 100 ng/μL linear DNA full-length PCR segment for targeting of Red recombination.

(5) Red Recombination Operation

First, pKD46 carrier is introduced into the AT-004-02 strain of *Escherichia coli*. Then, the prepared linear DNA segment for targeting is electrotransformed, and positive clones are screened. Finally, the resistance gene is removed.

1. Transformation of pKD46 Plasmid

① Preparation of Competence: First, inoculate the bacterial suspension of *Escherichia coli* AT-004-02 stored at −20° C. into 10 mL of LB broth medium in a ratio of 1:50-100, and shake-cultivate at 37° C. and 225 rpm for 2-3 h. Then add the culture solution to a 10-mL centrifuge tube, centrifugate at 4000 g×5 min, discard the supernatant, and suspend with 5 mL 0.1M $CaCl_2$ on an ice bath for 5 min. Finally, centrifugate at 4000 g×5 min, discard the supernatant, and suspend with 5 mL of 0.1M $CaCl_2$ on an ice bath. Allow to stand at −4° C. for 12 h for spontaneous sedimentation.

② Plasmid Transformation: Transfer 250 μL of spontaneously sedimented thalli, add 5 μL of pKD46 plasmid, and cultivate at −4° C. for 30 min. Then heat on a water bath at 42° C. for 1.5 min, add 0.7 mL of SOC medium, and shake at 30° C. for 2 h. Transfer 0.2 mL of the bacterial suspension, and smear on a penicillin plate. Cultivate overnight (for 12-16 h) at 30° C. Pick up monoclone, add 5 mL of LB broth medium and cultivate, and withdraw plasmid for identification. Store the positive strain for use.

2. Electrotransform Linear DNA Segment for Targeting, and Screen Positive Clone

① Preparation of Electrotransformed Competence: Inoculate the AT-004-02 strain of *Escherichia coli*, containing pKD46, into a test tube of LB medium containing Ampicillin (Amp), and shake-cultivate at 250 rpm, on the next day, inoculate in a ratio of 1% into LB medium containing Amp, and cultivate at 30° C.; when $OD_{600}$ reaches approximately 0.2, add 0.2% L-Arabinose, and induce at 30° C. for 35 min until $OD_{600}$ reaches approximately 0.4. Cool on an ice bath. Wash once with ultrapure water, wash twice with 10% glycerin, and finally resuspend with 10% glycerin; the amount of glycerin used is to produce a final concentration of the thalli concentrated by 500-1000 folds.

② Transformation by electric shock: Take out a 2-mm electrotransformation cup from 70% ethanol, wash with sterilized ultrapure water, and irradiate by UV lamp for 30 min. Precool at 4° C. for 30 min. Transfer 90 μL of finally resuspended cells to a precooled centrifuge tube, add 5 μL (more than 100 ng) of the full-length PCR segment (linear DNA) obtained in Step (4), suction gently by a gun, and maintain on an ice bath for 30 min. Electrotransformation Parameters: 2500V, 200Ω, 25 μF.

Resuscitate and screen positive clones: add 1 mL of LB broth medium, and cultivate at 37° C. and 100 rpm for 1 h. Then smear one kanamycin (Kan) plate with every 200 μL, 5 plates in total. Smear evenly and allow to air-dry. Cultivate at 30° C. for 24 h. Pick up clones grown under kanamycin resistance, and carry out PCR identification to screen positive clones.

No. of the obtained strain: AT-007-01 (AT-004-02, ΔnagE::pTrc-nanKM-fKanrf).

(6) Removal of the Resistance Gene

Introduce pCP20 into the above kanamycin-resistant clones, cultivate at 30° C. for 8 h, then increase to 42° C. and cultivate overnight, and thermally induce to express FLP recombinase; the plasmids are lost gradually. Streak the plate of antibiotics-free culture medium by an inoculating loop dipped in the bacterial suspension, pick up grown monoclones and dot on the kanamycin-resistant plate; those that cannot grown are clones of which the kanamycin resistance gene has been removed by FLP recombination. Carry out PCR with identification primer to identify clones losing kanamycin resistance.

No. of the obtained strain: AT-007-02 (AT-004-02, ΔnagE::pTrc-nanKM).

5. Influence of pTrc-nanKM Gene Cassette Integration on the Output of N-Acetyl-D-Glucosamine Carry out a shake-flask fermentation trial with the recombinant strain AT-007-02 of which the nagE gene site in the chromosome is integrated with pTrc-nanKM gene cassette, and the reference strain. Transfer the monoclonal strain freshly cultivated in culture medium of the LB plate, inoculate into a test tube (13×150 mm) containing 3 mL of the LB broth culture medium, and shake-cultivate at 30° C. for 8 h. Then transfer the seed culture solution, inoculate in 3% into a 250-mL shake-flask containing 50 mL of the fermentation culture solution (M9 culture solution). The initial $OD_{600}$ is approximately 0.5; shake-cultivate at 37° C. and 225 rpm. The fermentation cycle is 72 h. At 24 h and 48 h, adjust to pH 7.0 with 10M NaOH. According to glucose consumption in the fermentation broth, add 65% glucose solution to maintain a glucose concentration of 20 g/L. After completion of fermentation, transfer 1 mL of the fermentation broth and centrifugate. Measure the content of N-Acetyl-D-Glucosamine by HPLC method.

See Table 5 for the output from shake-flask fermentation. The results show that: The output by the reference strain AT-005-02 is very low and is not detected, while the output by the recombinant strain AT-007-02 integrated with pTrc-nanKM gene cassette is increased obviously, and is also increased significantly than that by the unmutant reference strain (AT-006-02).

TABLE 5

Output from Shake-flask Fermentation by the Recombinant Strain integrated with pTrc-nanKM Gene Cassette

| Species | Output of N-Acetyl-D-Glucosamine (g/L) |
|---|---|
| AT-005-02 (AT-004-02,·nagE) (Reference) | Not detected |
| AT-006-02 (AT-004-02,·nagE::pTrc-nanK) | 4.5 ± 0.4 |
| AT-007-02 (AT-004-02,·nagE::pTrc-nanKM) | 11.2 ± 1.2 |

The above results show that: The output of N-Acetyl-D-Glucosamine may be increased obviously by overexpression of N-Acetyl-D-Mannosamine Kinase; moreover, the output of N-Acetyl-D-Glucosamine may also be greatly by the mutant screened by error-prone PCR technology, due to increased activities of the obtained mutant of the enzyme.

EXAMPLE 4

This implementation example describes *Escherichia coli* strains integrated with pTrc-nanKM gene cassette, and the gene (NanE) thereof for overexpression of N-Acetyl-D-Mannosamine-6-P Epimerase as well as its influence on the output of N-Acetyl-D-Glucosamine.

Amplify the gene nanE of *Escherichia coli* NanE (N-acetylmannosamine-6-phosphate epimerase, N-Acetyl-D-Mannosamine-6-P Epimerase), insert pTrc99A so that nanE is controlled by Trc promoter yp transform the strains, or the natural endogenous promoter with nanE gene is replaced by Trc promoter for overexpression of the enzyme, to strengthen transformation of N-Acetyl-D-Mannosamine-6-Phosphate (ManNAc-6-P) into N-Acetyl-D-Glucosamine-6-Phosphate (GlcNAc-6-P).

1. Amplify the nanE Gene and Insert λ pTrc99A

From NCBI, look up U00096, to obtain the nucleotide sequence SEQ ID No.28 of the nanE gene of *Escherichia coli*, which amino acid sequence is SEQ ID No.29.

Primer Design: Forward primer (nanE-F) SEQ ID No.30, and reverse primer (nanE-R) SEQ ID No.31.

Template: AT-001 (*Escherichia coli* ATCC 27325) Genome.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product Size: 690 kb.

The PCR product is separated by 1% agarose gel electrophoresis, and purified to recover the segment.

Digest enzymatically the obtained PCR amplification segment and carrier pTrc99A with Nco I and Hind III, separate by agarose gel electrophoresis, purify and recover nanE segment and pTrc99A segment, connect overnight with T4 DNA ligase at 16° C., and carry out identification to obtain nanE/pTrc99A plasmid.

2. Transformation and Integration of *Escherichia coli* Strains with pTrc-NanKM Gene Cassette by nanE/pTrc99A (1) Preparation of Competence ① Inoculate the bacterial suspension of AT-007-02 stored at −20° C. into 10 mL of LB broth medium in a ratio of 1:50-100, and shake-cultivate at 37° C. and 225 rpm for 2-3 h.

② Add the culture solution to a 10-mL centrifuge tube, centrifugate at 4000 g×5 min, discard the supernatant, and suspend with 5 mL 0.1M $CaCl_2$ on an ice bath for 5 min.

③ Centrifugate at 4000 g×5 min, discard the supernatant, and suspend with 5 mL of 0.1M $CaCl_2$ on an ice bath. Allow to stand at −4° C. for 12 h for spontaneous sedimentation.

(2) Plasmid Transformation

① Transfer 250 μL of spontaneously sedimented thalli, add 5 μL of nanE/pTrc99A plasmid, and cultivate at −4° C. for 30 min. ② Heat on a water bath at 42° C. for 1.5 min, add 0.7 mL of SOC medium, and shake at 30° C. for 2 h.

③ Transfer 0.2 mL of the bacterial suspension, and smear on a penicillin plate.

④ Cultivate overnight (for 12-16 h) at 30° C.

⑤ Pick up monoclone, add 5 mL of LB broth medium and cultivate, and withdraw plasmid for identification.

⑥ Positive clones are stored for use.

No. of the obtained strain: AT-008 (AT-007-02, nanE/pTrc99A).

3. The Natural Endogenous Promoter with nanE gene of *Escherichia coli* Strains Integrated with pTrc-nanKM Cassette is Replaced with Trc Promoter First, amplify Trc promoter sequence segment and fKanrf segment, and splice together. Then design homologous primers, and amplify linear DNA full-length segment for targeting of Red recombination.

(1) Amplification of Trc Promoter Sequence

According to public information, look up Trc promoter sequence: SEQ ID No.32.

Primer Design: Forward primer (KanTrcRed-F) SEQ ID No.33, and reverse primer (KanTrcRed-R) SEQ ID No.34.

Template: pTrc99A

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Product Size: 166 bp.

The PCR product is separated by 1% agarose gel electrophoresis, and purified to recover the segment.

(2) Amplify the Kanamycin Resistance Gene with Recognition Sites (FRT Sites) for FLP Recombinase at its Both Ends: fKanrf Primer Design: Forward primer (mfKanf-F) SEQ ID No.1, and reverse primer (mfKanf-R) SEQ ID No.2.

Template: pPic9K.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

fKanrf size: 1.28 kb. Its nucleotide sequence is SEQ ID No.3.

The PCR product is separated by 1% agarose gel electrophoresis, and purified to recover the segment.

(3) Amplification of fKanrf Spliced with Trc Promoter

Primer Design: Forward primer (fKanfRed-F1) SEQ ID No.35, and reverse primer (fKanfRed-R1) SEQ ID No.36.

Template: fKanrf.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

fKanrf size from secondary amplification: 1.3 kb.

The PCR product is separated by 1% agarose gel electrophoresis, and purified to recover the segment.

(4) Preparation of Linear DNA Full-Length PCR Segment for Targeting of Red Recombination Design homologous primers: Based on promoter sequence SEQ ID No.37 of the nanE gene. Design primers to be replaced with Trc promoter: Forward primer (Pro-NanEpTrc-F) SEQ ID No.38, and reverse primer (Pro-NanEpTrc-R) SEQ ID No.39.

Template: Mix Trc promoter PCR segment and fKanrf PCR segment from secondary amplification in the ratio of 1:1.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product: Homologous Arm+fKanrf+Trc Promoter+Homologous Arm.

The PCR product is separated by agarose gel electrophoresis, and purified and recovered to obtain 100 ng/µL linear DNA full-length PCR segment for targeting of Red recombination.

(5) Red Recombination Operation

First, pKD46 carrier is introduced into the AT-007-02 strain of *Escherichia coli*. Then, the prepared linear DNA segment for targeting is electrotransformed, and positive clones are screened. Finally, the resistance gene is removed.

No. of the obtained strain: AT-009 (AT-007-02, ·nanE promotor::Trc promoter).

4. Recombinant Strain Integrated with pTrc-nanKM Gene Cassette, and Influences of the Strain Thereof with nanE/pTrc99A by Transformation, and of the Strain Thereof with nanE Promoter Replaced by Trc Promoter on the Output of N-Acetyl-D-Glucosamine.

Carry out a shake-flask fermentation trial with the strain integrated with pTrc-nanKM gene cassette, and the strain thereof for overexpression of NanE (including the strain thereof with nanE/pTrc99A by transformation and the strain thereof with NanE promoter replaced by Trc promoter). Transfer the monoclonal strain freshly cultivated in culture medium of the LB plate, inoculate into a test tube (13×150 mm) containing 3 mL of the LB broth culture medium, and shake-cultivate at 30° C. for 8 h. Then transfer the seed culture solution, inoculate in 3% into a 250-mL shake-flask containing 50 mL of M9 culture solution. The initial $OD_{600}$ is approximately 0.5; shake-cultivate at 37° C. and 225 rpm. The fermentation cycle is 72 h. At 24 h and 48 h, adjust to pH 7.0 with 10M NaOH. According to glucose consumption in the fermentation broth, add 65% glucose solution to maintain a glucose concentration of 20 g/L. After completion of fermentation, transfer 1 mL of the fermentation broth and centrifugate. Measure the content of N-Acetyl-D-Glucosamine by HPLC method.

See Table 6 for the output from shake-flask fermentation by recombinant strains. The results show that: The output may be increased obviously from overexpression of NanE from whether NanE promoter is replaced by Trc promoter, or nanE/pTrc99A plasmid is transformed; moreover, the output is increased more significant from the recombinant strain with NanE promoter replaced by Trc promoter than that with transformed nanE/pTrc99A plasmid.

TABLE 6

Output from Shake-flask Fermentation by the Recombinant Strain integrated with pTrc-nanKM Gene Cassette, for Overexpression of NanE

| species | Output of N-Acetyl-D-Glucosamine (g/L) |
|---|---|
| AT-007-02 (Reference) | 11.5 ± 1.2 |
| AT-008 (AT-007-02, nanE/pTrc99A) | 16.3 ± 1.1 |
| AT-009 (AT-007-02,· nanE promotor::Trc promoter) | 19.7 ± 1.4 |

EXAMPLE 5

This implementation example describes *Escherichia coli* strains integrated with pTrc-nanKM, and influences of those with the natural endogenous promoter is replaced and/or deleted in the gene glmS of Glucosamine-6-Phosphate Synthase (GlmS) and/or the nagB gene of D-Glucosamine-6-Phosphate Deaminase (NagB) on the output of N-Acetyl-D-Glucosamine.

1. Influences of *Escherichia coli* strains integrated with pTrc-NanKM gene cassette on the output of N-Acetyl-D-Glucosamine, of which the natural endogenous promoter of the nagB gene is replaced by Trc promoter, or the natural endogenous promoter of the glmS gene is further deleted.

(1) The Natural Endogenous Promoter of the nagB Gene is Replaced by Trc Promoter The gene promoter of D-Glucosamine-6-Phosphate Deaminase (NagB) in nag regulon (nagE-nagBACD) is replaced by Trc promoter. The reaction catalyzed by D-Glucosamine-6-Phosphate Deaminase (NagB) is reversible; overexpression of nagB may accelerate the forward catalytic reaction by NagB, to achieve the purpose of increasing D-Glucosamine-6-Phosphate (GlcN-6-P).

First, amplify Trc promoter segment and fKanrf segment, and splice together. Then design homologous primers, and amplify linear DNA full-length segment for targeting of Red recombination.

1) Preparation of Linear DNA Full-Length PCR Segment for Targeting of Red Recombination Design of Homologous Arm Primers: From NCBI, look up NC_000913, nagB promoter sequence and nagA gene sequence SEQ ID No.13 of *Escherichia coli* str.K-12, design the homologous arm primers for deletion of nagB promoter: Forward primer (nagBKO-F1) SEQ ID No.40 and reverse primer (nagBKO-R1) SEQ ID No.41.

Template: Mix Trc promoter PCR segment and fKanrf PCR segment from secondary amplification in the ratio of 1:1.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product: Homologous Arm+fKanrf+Trc Promoter+Homologous Arm.

The PCR product is separated by agarose gel electrophoresis, and purified and recovered to obtain 100 ng/μL linear DNA full-length PCR segment for targeting of Red recombination.

2) Red Recombination Operation

First, pKD46 carrier is introduced into the AT-007-02 strain of *Escherichia coli*. Then, the prepared linear DNA segment for targeting is electrotransformed, and positive clones are screened. Finally, the resistance gene is removed.

No. of the obtained strain: AT-010 (AT-007-02, ▸ nagB promotor::Trc promoter).

(2) Deletion of the Natural Endogenous Promoter of the glmS Gene

Deletion of the gene promoter of Glucosamine-6-Phosphate Synthase (glmS). Glucosamine-6-Phosphate Synthase (GlmS), also called as L-Glutamine-D-fructose-6-phosphate aminotransferase, can catalyze amination of Glucose-6-Phosphate (Glc-6-P) into D-Glucosamine-6-Phosphate (GlcN-6-P), but has a severe problem for product inhibition. When the promoter sequence is deleted so that the enzyme cannot be expressed, it may solve product inhibition of GlcN-6-P.

First, amplify fKanrf segment; then design homologous primers, and amplify linear DNA full-length segment for targeting of Red recombination.

1) Amplify the Kanamycin Resistance Gene with Recognition Sites (FRT Sites) for FLP Recombinase at its Both Ends: fKanrf Primer Design: Forward primer (mfKanf-F) SEQ ID No.1, and reverse primer (mfKanf-R) SEQ ID No.2.

Template: pPic9K.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

fKanrf size: 1.28 kb. Its nucleotide sequence is SEQ ID No.3.

The PCR product is separated by 1% agarose gel electrophoresis, and purified to recover the segment.

2) Preparation of Linear DNA Full-Length PCR Segment for Targeting of Red Recombination Design of Homologous Primers: From NCBI, look up NC_000913, the gene promoter sequence SEQ ID No.42 of Glucosamine-6-Phosphate Synthase (GlmS) of *Escherichia coli* str.K-12, design the homologous arm primers for deletion of glmS gene promoter: Forward primer (ProglmsKO-F) SEQ ID No.43 and reverse primer (ProglmsKO-R) SEQ ID No.44.

Template: fKanrf PCR Segment.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product: Homologous Arm+fKanf+Homologous Arm.

The PCR product is separated by agarose gel electrophoresis, and purified and recovered to obtain 100 ng/μL linear DNA full-length PCR segment for targeting of Red recombination.

3) Red Recombination Operation

First, pKD46 carrier is introduced into the AT-010 strain of *Escherichia coli*. Then, the prepared linear DNA segment for targeting is electrotransformed, and positive clones are screened. Finally, the resistance gene is removed.

No. of the obtained strain: AT-011 (AT-010, ▸ glmS promotor).

(3) Influence of the Strains of which nagB Promoter Replaced by a Promoter with Higher Expression Level, or glmS Promoter is Further Deleted, on the Output of N-Acetyl-D-Glucosamine Carry out a shake-flask fermentation trial with the recombinant strains integrated with pTrc-nanKM gene cassette, of which nagB promoter is replaced by a promoter with higher expression level, or glmS promoter is further deleted. Transfer the monoclonal strain freshly cultivated in culture medium of the LB plate, inoculate into a test tube (13×150 mm) containing 3 mL of the LB broth culture medium, and shake-cultivate at 30° C. for 8 h. Then transfer the seed culture solution, inoculate in 3% into a 250-mL shake-flask containing 50 mL of the fermentation culture solution (M9 culture solution). The initial OD600 is approximately 0.5; shake-cultivate at 37° C. and 225 rpm. The fermentation cycle is 72 h. At 24 h and 48 h, adjust to pH 7.0 with 10M NaOH. According to glucose consumption in the fermentation broth, add 65% glucose solution to maintain a glucose concentration of 20 g/L. After completion of fermentation, transfer 1 mL of the fermentation broth and centrifugate. Measure the content of N-Acetyl-D-Glucosamine by HPLC method.

See Table 7 for the output from shake-flask fermentation. The results show that: The output of N-Acetyl-D-Glucosamine is obviously increased by the recombinant strains of which nagB promoter is replaced by Trc promoter, or glmS promoter is further deleted.

TABLE 7

Output from Shake-flask Fermentation by Recombinant Strains of which nagB promoter is replaced or glmS promoter is further deleted

| species | Output of N-Acetyl-D-Glucosamine (g/L) |
|---|---|
| AT-007-02 (Reference) | 11.6 ± 1.2 |
| AT-010 (AT-007-02,▸ nagB promotor::Trc promoter) | 17.2 ± 1.3 |
| AT-011 (AT-010,▸ glmS promotor) | 21.4 ± 1.5 |

2. Influences of *Escherichia coli* strains integrated with pTrc-NanKM gene cassette on the output of N-Acetyl-D-Glucosamine, of which the natural endogenous promoter of the glmS gene is replaced by Trc promoter, or the natural endogenous promoter of the glmS gene is further deleted.

(1) The Natural Endogenous Promoter of the glmS Gene is Replaced by Trc Promoter The gene promoter sequence of L-Glutamine-D-Fructose-6-Phosphate Aminotransferase is replaced by Trc promoter sequence. L-Glutamine-6-Phosphate Aminotransferase, also called as Glucosamine-6-Phosphate Synthase (GlmS); replacement of its promoter sequence is replaced by Trc promoter sequence may overexpress glmS, and accelerate GlmS catalytic function, to achieve the purpose of increasing D-Glucosamine-6-Phosphate (GlcN-6-P).

First, amplify Trc promoter sequence segment and fKanrf segment, and splice together. Then design homologous primers, and amplify linear DNA full-length segment for targeting of Red recombination.

1) Amplification of Linear DNA Full-Length PCR Segment for Targeting of Red Recombination Design of homologous arm primers: According to the glmS gene promoter sequence SEQ ID No.42, design homologous arm primers with the promoter replaced by Trc promoter: Forward primer (ProglmspTrc-F) SEQ ID No.45, and reverse primer (ProglmspTrc-R) SEQ ID No.46.

Template: Mix Trc promoter PCR segment and fKanrf PCR segment from secondary amplification in the ratio of 1:1.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product: Homologous Arm+fKanrf+Trc Promoter+Homologous Arm.

The PCR product is separated by agarose gel electrophoresis, and purified and recovered to obtain 100 ng/μL linear DNA full-length PCR segment for targeting of Red recombination.

2) Red Recombination Operation

First, pKD46 carrier is introduced into the AT-007-02 strain of *Escherichia coli*. Then, the prepared linear DNA segment for targeting is electrotransformed, and positive clones are screened. Finally, the resistance gene is removed.

No. of the obtained strain: AT-012 (AT-007-02, ▸ glmS promotor::Trc promoter).

(2) Deletion of the Natural Endogenous Promotor of NagB Gene

Deletion of the gene promoter sequence of D-Glucosamine-6-Phosphate Deaminase (NagB) in the nag regulon (nagE-nagBACD), so that nagB loses its function, may eliminate the reverse catalytic function of NagB and reduce production of Glc-6-P from GlcN-6-P.

First, amplify fKanrf segment; then design homologous primers, and prepare linear DNA full-length segment for targeting of Red recombination.

1) Preparation of Linear DNA Full-Length PCR Segment for Targeting of Red Recombination Design of Homologous Arm Primers: According to nagB promoter sequence and nagA gene sequence SEQ ID No.13, design the homologous arm primers for deletion of nagB promoter sequence: Forward primer (nagBKO-F2) SEQ ID No.47 and reverse primer (nagBKO-R2) SEQ ID No.48.

Template: fKanrf PCR Segment

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product: Homologous Arm+fKanrf+Homologous Arm.

The PCR product is separated by agarose gel electrophoresis, and purified and recovered to obtain 100 ng/μL linear DNA full-length PCR segment for targeting of Red recombination.

2) Red Recombination Operation

First, pKD46 carrier is introduced into the AT-012 strain of *Escherichia coli*. Then, the prepared linear DNA segment for targeting is electrotransformed, and positive clones are screened. Finally, the resistance gene is removed.

No. of the obtained strain: AT-013 (AT-012, ▸ nagB promotor).

(3) Influence of the Strains of which glmS Promoter Replaced by a Promoter with Higher Expression Level, or is Further Deleted, on the Output of N-Acetyl-D-Glucosamine Carry out a shake-flask fermentation trial with the recombinant strains integrated with pTrc-nanKM gene cassette, of which glmS promoter is replaced by a promoter with higher expression level, or nagB promoter is further deleted. Transfer the monoclonal strain freshly cultivated in culture medium of the LB plate, inoculate into a test tube (13×150 mm) containing 3 mL of the LB broth culture medium, and shake-cultivate at 30° C. for 8 h. Then transfer the seed culture solution, inoculate in 3% into a 250-mL shake-flask containing 50 mL of the fermentation culture solution (M9 culture solution). The initial OD600 is approximately 0.5; shake-cultivate at 37° C. and 225 rpm. The fermentation cycle is 72 h. At 24 h and 48 h, adjust to pH 7.0 with 10M NaOH. According to glucose consumption in the fermentation broth, add 65% glucose solution to maintain a glucose concentration of 20 g/L. After completion of fermentation, transfer 1 mL of the fermentation broth and centrifugate. Measure the content of N-Acetyl-D-Glucosamine by HPLC method.

See Table 8 for the output from shake-flask fermentation. The results show that: The output of N-Acetyl-D-Glucosamine is not obviously increased by the recombinant strains of which glmS promoter is replaced by Trc promoter; however, the output of N-Acetyl-D-Glucosamine is increased when nagB promoter is meanwhile deleted, than that by the reference strain.

TABLE 8

Output from Shake-flask Fermentation by Recombinant Strains of which glmS promoter is replaced or nagB promoter is further deleted

| species | Output of N-Acetyl-D-Glucosamine (g/L) |
| --- | --- |
| AT-007-02 (Reference) | 11.6 ± 1.5 |
| AT-012 (AT-007-02,▸ glmS promotor::Trc promoter) | 11.9 ± 1.4 |
| AT-013 (AT-012,▸ nagB promotor) | 21.4 ± 1.6 |

EXAMPLE 6

This implementation example describes *Escherichia coli* strains integrated with pTrc-nanKM gene cassette, and influences of those on the output of N-Acetyl-D-Glucosamine, of which the natural endogenous promoter of the gene nagB of D-Glucosamine-6-Phosphate Deaminase (NagB), and of the gene GlmS of Glucosamine-6-Phosphate Synthase (GlmS) is replaced and/or deleted to transform nanE/pTrc99A plasmid, or the natural endogenous promoter of the nanE gene is replaced by Trc promoter.

1. *Escherichia coli* strains integrated with pTrc-nanKM cassette are used to transform nanE/pTrc99A plasmid, of which the natural endogenous promoter of the nagB gene is replaced by Trc promoter, and meanwhile the natural endogenous promoter of the glmS gene is deleted (1) Preparation of Competence: First, inoculate the bacterial suspension of AT-011 stored at −20° C. into 10 mL of LB broth medium in a ratio of 1:50-100, and shake-cultivate at 37° C. and 225 rpm for 2-3 h. Then add the culture solution to a 10-mL centrifuge tube, centrifugate at 4000 g×5 min, discard the supernatant, and suspend with 5 mL 0.1M $CaCl_2$ on an ice bath for 5 min. Finally, centrifugate at 4000 g×5 min, discard the supernatant, and suspend with 5 mL of 0.1M $CaCl_2$ on an ice bath. Allow to stand at −4° C. for 12 h for spontaneous sedimentation.

(2) Plasmid Transformation: Transfer 250 μL of spontaneously sedimented thalli, add 5 μL of nanE/pTrc99A plasmid, and cultivate at −4° C. for 30 min. Then heat on a water bath at 42° C. for 1.5 min, add 0.7 mL of SOC medium, and shake at 30° C. for 2 h. Transfer 0.2 mL of the bacterial suspension, and smear on a penicillin plate. Cultivate overnight (for 12-16 h) at 30° C. Pick up monoclone, add 5 mL of LB broth medium and cultivate, and withdraw plasmid for identification. Positive clones are stored for use.

No. of the obtained strain: AT-014 (AT-011, nanE/pTrc99A).

2. In *Escherichia coli* strains integrated with pTrc-nanKM cassette, of which the natural endogenous promoter of the nagB gene is replaced by Trc promoter and meanwhile the natural endogenous promoter of the glmS gene is deleted, the natural endogenous promoter of the NanE gene is replaced by Trc promoter First, amplify Trc promoter sequence segment and fKanrf segment, and splice together. Then design homologous primers, and amplify linear DNA full-length segment for targeting of Red recombination.

(1) Preparation of Linear DNA Full-Length PCR Segment for Targeting of Red Recombination Design homologous primers: Based on promoter sequence SEQ ID No.37 of the nanE gene. Design primers to be replaced with Trc promoter: Forward primer (Pro-NanEpTrc-F) SEQ ID No.38, and reverse primer (Pro-NanEpTrc-R) SEQ ID No.39.

Template: Mix Trc promoter PCR segment and fKanrf PCR segment from secondary amplification in the ratio of 1:1.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product: Homologous Arm+fKanrf+Trc Promoter+Homologous Arm.

The PCR product is separated by agarose gel electrophoresis, and purified and recovered to obtain 100 ng/μL linear DNA full-length PCR segment for targeting of Red recombination.

(2) Red Recombination Operation

First, pKD46 carrier is introduced into the AT-011 strain of *Escherichia coli*. Then, the prepared linear DNA segment for targeting is electrotransformed, and positive clones are screened. Finally, the resistance gene is removed.

No. of the obtained strain: AT-015 (AT-011, ▸nanE promotor::Trc promoter).

3. *Escherichia coli* strains integrated with pTrc-nanKM cassette are used to transform nanE/pTrc99A plasmid, of which the natural endogenous promoter of the glmS gene is replaced by Trc promoter, and meanwhile the natural endogenous promoter of the nagB gene is deleted First, prepare competence of recombinant *Escherichia coli* strain AT-013; then, NanE/pTrc99A plasmid is transformed into AT-013 by $CaCl_2$ transformation method, pick up monoclones and cultivate, and pipet plasmid to identify positive clones.

No. of the obtained strain: AT-016 (AT-013, nanE/pTrc99A).

4. In *Escherichia coli* strains integrated with pTrc-nanKM cassette, of which the natural endogenous promoter of the glmS gene is replaced by Trc promoter and meanwhile the natural endogenous promoter of the nagB gene is deleted, the natural endogenous promoter of the NanE gene is replaced by Trc promoter (1) Preparation of Linear DNA Full-Length PCR Segment for Targeting of Red Recombination First, amplify Trc promoter sequence segment and fKanrf segment, and splice together. Then design homologous primers, and amplify linear DNA full-length segment for targeting of Red recombination.

(2) Red Recombination Operation

First, pKD46 carrier is introduced into the AT-013 strain of *Escherichia coli*. Then, the prepared linear DNA segment for targeting is electrotransformed, and positive clones are screened. Finally, the resistance gene is removed.

No. of the obtained strain: AT-017 (AT-013, ▸nanE promotor::Trc promoter).

5. Influences of the *Escherichia coli* strains integrated with pTrc-nanKM gene cassette on the output of N-Acetyl-D-Glucosamine, of which the natural endogenous promoter of the nagB gene and glmS gene is replaced and/or deleted to transform nanE/pTrc99A plasmid, and the natural endogenous promoter of the nanE gene is replaced by Trc promoter Carry out a shake-flask fermentation trial with the recombinant strains with different genotypes, obtained form the strains integrated with pTrc-nanKM gene cassette, of which the natural endogenous promoter of the glmS and nagB genes are replaced and/or deleted to transform nanE/pTrc99A plasmid, or the natural endogenous promoter of the nanE gene is replaced by Trc promoter. Transfer the monoclonal strain freshly cultivated in culture medium of the LB plate, inoculate into a test tube (13×150 mm) containing 3 mL of the LB broth culture medium, and shake-cultivate at 30° C. for 8 h. Then transfer the seed culture solution, inoculate in 3% into a 250-mL shake-flask containing 50 mL of the fermentation culture solution (M9 culture solution). The initial OD600 is approximately 0.5; shake-cultivate at 37° C. and 225 rpm. The fermentation cycle is 72 h. At 24 h and 48 h, adjust to pH 7.0 with 10M NaOH. According to glucose consumption in the fermentation broth, add 65% glucose solution to maintain a glucose concentration of 20 g/L. After completion of fermentation, transfer 1 mL of the fermentation broth and centrifugate. Measure the content of N-Acetyl-D-Glucosamine by HPLC method.

See Table 9 for the output from shake-flask fermentation. The results show that: The output of N-Acetyl-D-Glucosamine may be increased substantially from overexpression of NanE by recombinant strain with NanE promoter replaced by Trc promoter, or with transformed nanE/pTrc99A plasmid; moreover, the output of N-Acetyl-D-Glucosamine is increased more significantly by the recombinant strain with NanE promoter replaced by Trc promoter, than that with transformed nanE/pTrc99A plasmid.

TABLE 9

Output from Shake-flask Fermentation by Recombinant
Strains with Transformed NanE/pTrc99A Plasmid or
with NanE promoter replaced by Trc Promoter

| species | Output of N-Acetyl-D-Glucosamine (g/L) |
|---|---|
| AT-011 (Reference) | 21.6 ± 1.8 |
| AT-014 (AT-011, nanE/pTrc99A) | 26.1 ± 1.5 |
| AT-015 (AT-011,▪ nanE promotor::Trc promoter) | 29.8 ± 1.5 |
| AT-013 (Reference) | 21.2 ± 1.6 |
| AT-016 (AT-013, nanE/pTrc99A) | 26.7 ± 1.6 |
| AT-017 (AT-013,▪ nanE promotor::Trc promoter) | 30.9 ± 1.5 |

EXAMPLE 7

This implementation example describes *Escherichia coli* strains integrated with pTrc-nanKM gene cassette, and the gene wecB thereof for overexpression of UDP-N-Acetyl-D-Glucosamine-2-Epimerase as well as its influence on the output of N-Acetyl-D-Glucosamine.

The gene wecB of UDP-N-AcetylGlucosamine-2-Epimerase (WecB) is controlled by Trc promoter to transform strains, or the natural endogenous promoter of the wecB gene is replaced by Trc promoter for overexpression of the enzyme, to strengthen production of ManNAc (N-Acetyl-D-mannosamine, N-Acetyl-D-Mannosamine or N-Acetyl-D-Mannosamine) from UDP-GlcNAc (UDP-N-Acetyl Glucosamine, UDP-N-Acetyl-D-Glucosamine).

1. Transformation of *Escherichia coli* Strains Integrated with pTrc-NanKM Gene Cassette by wecB/pTrc99A (1) Amplify the wecB Gene of *Escherichia coli* and Insert pTrc99A According to NCBI, look up the nucleotide sequence SEQ ID No.49 of the wecB gene of *Escherichia coli*, and its amino acid sequence is SEQ ID No.50.

Primer Design: Forward primer (TrcwecB-F) SEQ ID No.51, and reverse primer (TrcwecB-R) SEQ ID No.52.

Template: AT-001 (*Escherichia coli* ATCC 27325) Genome.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product Size: 1.13 kb.

The PCR product is separated by 1% agarose gel electrophoresis, and purified to recover the segment.

Digest enzymatically the obtained PCR amplification segment and carrier pTrc99A with Nco I and Hind III, separate by agarose gel electrophoresis, purify and recover wecB segment and pTrc99A segment, connect overnight with T4 DNA ligase at 16° C., and carry out identification to obtain wecB/pTrc99A plasmid.

(2) Transformation of *Escherichia coli* Strains Integrated with pTrc-NanKM Gene Cassette by wecB/pTrc99A (1) Preparation of Competence: First, inoculate the bacterial suspension of AT-007-02 stored at −20° C. into 10 mL of LB broth medium in a ratio of 1:50-100, and shake-cultivate at 37° C. and 225 rpm for 2-3 h. Then add the culture solution to a 10-mL centrifuge tube, centrifugate at 4000 g×5 min, discard the supernatant, and suspend with 5 mL 0.1M CaCl$_2$ on an ice bath for 5 min. Finally, centrifugate at 4000 g×5 min, discard the supernatant, and suspend with 5 mL of 0.1M CaCl$_2$ on an ice bath. Allow to stand at −4° C. for 12 h for spontaneous sedimentation.

(2) Plasmid Transformation: Transfer 250 µL of spontaneously sedimented thalli, add 5 µL of wecB/pTrc99A plasmid, and cultivate at −4° C. for 30 min. Then heat on a water bath at 42° C. for 1.5 min, add 0.7 mL of SOC medium, and shake at 30° C. for 2 h. Transfer 0.2 mL of the bacterial suspension, and smear on a penicillin plate. Cultivate overnight (for 12-16 h) at 30° C. Pick up monoclone, add 5 mL of LB broth medium and cultivate, and withdraw plasmid for identification. Positive clones are stored for use.

No. of the obtained strain: AT-018 (AT-007-02, wecB/pTrc99A).

2. The Natural Endogenous Promoter of the wecB Gene of *Escherichia coli* Strains Integrated with pTrc-nanKM Cassette is Replaced with Trc Promoter First, amplify Trc promoter sequence segment and fKanrf segment, and splice together. Then design homologous primers, and amplify linear DNA full-length segment for targeting of Red recombination.

(1) Preparation of Linear DNA Full-Length PCR Segment for Targeting of Red Recombination Design of Homologous Arm Primers: According to NCBI, look up NC_000913 to obtain the nucleotide sequence SEQ ID No.53 of the gene promoter of *Escherichia coli* UDP-N-AcetylGlucosamine-2-Epimerase (WecB), design homologous arm primers with the promoter replaced by Trc promoter: Forward primer (ProwecBpTrc-F) SEQ ID No.54, and reverse primer (Pro wecBpTrc-R) SEQ ID No.55.

Template: Mix Trc promoter PCR segment and fKanrf PCR segment from secondary amplification in the ratio of 1:1.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product: Homologous Arm+fKanrf+Trc Promoter+Homologous Arm.

The PCR product is separated by agarose gel electrophoresis, and purified and recovered to obtain 100 ng/µL linear DNA full-length PCR segment for targeting of Red recombination.

(2) Red Recombination Operation

First, pKD46 carrier is introduced into the AT-007-02 strain of *Escherichia coli*. Then, the prepared linear DNA segment for targeting is electrotransformed, and positive clones are screened. Finally, the resistance gene is removed.

No. of the obtained strain: AT-019 (AT-007-02, ▪wecB promotor::Trc promoter).

3. Recombinant strain integrated with pTrc-nanKM gene cassette, and influences of the strain thereof with transformed wecB/pTrc99A plasmid, and of the strain thereof with nanE promoter replaced by Trc promoter on the output of N-Acetyl-D-Glucosamine.

Carry out a shake-flask fermentation trial with the strain integrated with pTrc-nanKM gene cassette, and the recombinant strain produced thereof for overexpression of wecB (including the strain thereof with transformed wecB/pTrc99A and the strain thereof with wecB promoter replaced by Trc promoter). Transfer the monoclonal strain freshly cultivated in culture medium of the LB plate, inoculate into a test tube (13×150 mm) containing 3 mL of the LB broth culture medium, and shake-cultivate at 30° C. for 8 h. Then transfer the seed culture solution, inoculate in 3% into a 250-mL shake-flask containing 50 mL of M9 culture solution. The initial OD$_{600}$ is approximately 0.5; shake-cultivate at 37° C. and 225 rpm. The fermentation cycle is 72 h. At 24 h and 48 h, adjust to pH 7.0 with 10M NaOH. According to glucose consumption in the fermentation broth, add 65% glucose solution to maintain a glucose concentration of 20 g/L. After completion of fermentation, transfer 1 mL of the fermentation broth and centrifugate. Measure the content of N-Acetyl-D-Glucosamine by HPLC method.

See Table 10 for the output from shake-flask fermentation. The results show that: Compared with the reference strain AT-007-02, the output of N-Acetyl-D-Glucosamine is increased obviously by recombinant strain with transformed wecB/pTrc99A, and is increased more greatly by recombinant strain with wecB promoter replaced by Trc promoter.

TABLE 10

Output from Shake-flask Fermentation by Recombinant Strains with Transformed wecB/ pTrc99A Plasmid or with wecB promoter replaced by Trc Promoter

| species | Output of N-Acetyl-D-Glucosamine (g/L) |
|---|---|
| AT-007-02 (Reference) | 11.8 ± 1.4 |
| AT-018 (AT-007-02, wecB/pTrc99A) | 16.3 ± 1.5 |
| AT-019 (AT-007-02,• wecB promotor::Trc promoter) | 23.2 ± 2.0 |

EXAMPLE 8

This implementation example describes influences of recombinant strains integrated with pTrc-nanKM gene cassette on the output of N-Acetyl-D-Glucosamine, of which the natural endogenous promoter of the nanE gene is replaced by Trc promoter to transform wecB/pTrc99A plasmid, or the natural endogenous promoter of the wecB gene is replaced by Trc promoter.

1. *Escherichia coli* strains integrated with pTrc-nanKM cassette are used to transform wecB/pTrc99A plasmid, of which the natural endogenous promoter of the nanE Gene is Replaced by Trc Promoter Preparation of competence: Transform wecB/pTrc99A plasmid with $CaCl_2$ into *Escherichia coli* strain AT-009 integrated with pTrc-NanKM gene cassette, of which the natural endogenous promoter of the nanE gene is replaced by Trc promoter, pick up monoclones and cultivate, and pipet plasmid to identify positive clones.

No. of the obtained strain: AT-020 (AT-009, wecB/pTrc99A).

2. In *Escherichia coli* strains integrated with pTrc-nanKM Cassette, of which the natural endogenous promoter of the nanE gene is replaced by Trc Promoter, the natural endogenous promoter of the NanE gene is replaced by Trc promoter First, pKD46 carrier is introduced into the AT-009 strain of *Escherichia coli*. Then, the prepared linear DNA segment for targeting is electrotransformed, and positive clones are screened. Finally, the resistance gene is removed.

No. of the obtained strain: AT-021 (AT-009, • wecB promotor::Trc promoter).

3. Influences of recombinant strains integrated with pTrc-nanKM gene cassette on the output of N-Acetyl-D-Glucosamine, of which the natural endogenous promoter of the nanE gene is replaced by Trc promoter to transform wecB/pTrc99A plasmid, and wecB promoter is replaced by Trc promoter Carry out a shake-flask fermentation trial with the strain integrated with pTrc-nanKM gene cassette, of which the natural endogenous promoter of the nanE gene is replaced by Trc promoter, and the recombinant strain produced thereof for overexpression of wecB (including the strain thereof with transformed wecB/pTrc99A and the strain with wecB promoter replaced by Trc promoter). Transfer the monoclonal strain freshly cultivated in culture medium of the LB plate, inoculate into a test tube (13×150 mm) containing 3 mL of the LB broth culture medium, and shake-cultivate at 30° C. for 8 h. Then transfer the seed culture solution, inoculate in 3% into a 250-mL shake-flask containing 50 mL of M9 culture solution. The initial $OD_{600}$ is approximately 0.5; shake-cultivate at 37° C. and 225 rpm. The fermentation cycle is 72 h. At 24 h and 48 h, adjust to pH 7.0 with 10M NaOH. According to glucose consumption in the fermentation broth, add 65% glucose solution to maintain a glucose concentration of 20 g/L. After completion of fermentation, transfer 1 mL of the fermentation broth and centrifugate. Measure the content of N-Acetyl-D-Glucosamine by HPLC method.

See Table 11 for the output from shake-flask fermentation. The results show that: Compared with the reference strain AT-009, the output of N-Acetyl-D-Glucosamine is increased obviously by recombinant strain with transformed wecB/pTrc99A, and is increased more greatly by recombinant strain with wecB promoter replaced by Trc promoter.

TABLE 11

Output from Shake-flask Fermentation by Recombinant Strains with Transformed wecB/pTrc99A Plasmid or with wecB promoter replaced by Trc Promoter

| species | Output of N-Acetyl-D-Glucosamine (g/L) |
|---|---|
| AT-009 (Reference) | 19.5 ± 1.5 |
| AT-020 (AT-009, wecB/pTrc99A) | 26.5 ± 1.8 |
| AT-021 (AT-009,• wecB promotor::Trc promoter) | 31.6 ± 2.1 |

EXAMPLE 9

This implementation example describes influences of the *Escherichia coli* strains integrated with pTrc-nanKM gene cassette on the output of N-Acetyl-D-Glucosamine, of which the natural endogenous promoter of the glmS gene and nagB gene is replaced and/or deleted to transform nanE/pTrc99A plasmid, and the natural endogenous promoter of the wecB gene is replaced by Trc promoter 1. *Escherichia coli* strains integrated with pTrc-nanKM cassette are used to transform wecB/pTrc99A plasmid, of which the natural endogenous promoter of the nagB gene is replaced by Trc promoter, and meanwhile the natural endogenous promoter of the glmS gene is deleted Preparation of competence: Transform wecB/pTrc99A plasmid with $CaCl_2$ into *Escherichia coli* strain AT-011 integrated with pTrc-NanKM gene cassette, of which the natural endogenous promoter of the nagB gene is replaced by Trc promoter and meanwhile the natural endogenous promoter of the glmS gene is deleted, pick up monoclones and cultivate, and pipet plasmid to identify positive clones.

No. of the obtained strain: AT-022 (AT-011, wecB/pTrc99A).

2. In *Escherichia coli* strains integrated with pTrc-nanKM cassette, of which the natural endogenous promoter of the nagB gene is replaced by Trc promoter and meanwhile the natural endogenous promoter of the glmS gene is deleted, the natural endogenous promoter of the wecB gene is replaced by Trc promoter First, pKD46 carrier is introduced into the AT-011 strain of *Escherichia coli*. Then, the prepared linear DNA segment for targeting is electrotransformed, and positive clones are screened. Finally, the resistance gene is removed.

No. of the obtained strain: AT-023 (AT-011, wecB promotor::Trc promoter).

3. *Escherichia coli* strains integrated with pTrc-nanKM cassette are used to transform wecB/pTrc99A plasmid, of which the natural endogenous promoter of the glmS gene is replaced by Trc promoter, and meanwhile the natural endogenous promoter of the nagB gene is deleted Preparation of competence: Transform wecB/pTrc99A plasmid with $CaCl_2$ into *Escherichia coli* strain AT-013 integrated with pTrc-nanKM gene cassette, of which the natural endogenous promoter of the glmS gene is replaced by Trc promoter and meanwhile the natural endogenous promoter of the nagB gene is deleted, pick up monoclones and cultivate, and pipet plasmid to identify positive clones.

No. of the obtained strain: AT-024 (AT-013, wecB/pTrc99A).

4. In *Escherichia coli* strains integrated with pTrc-nanKM cassette, of which the natural endogenous promoter of the glmS gene is replaced by Trc promoter and meanwhile the natural endogenous promoter of the nagB gene is deleted, the natural endogenous promoter of the wecB gene is replaced by Trc promoter First, pKD46 carrier is introduced into the AT-013 strain of *Escherichia coli*. Then, the prepared linear DNA segment for targeting is electrotransformed, and positive clones are screened. Finally, the resistance gene is removed.

No. of the obtained strain: AT-025 (AT-013, wecB promotor::Trc promoter).

5. Influences of the *Escherichia coli* strains integrated with pTrc-nanKM gene cassette on the output of N-Acetyl-D-Glucosamine, of which the natural endogenous promoter of the nagB gene and glmS gene is replaced and/or deleted to transform wecB/pTrc99A plasmid, and the natural endogenous promoter of the wecB gene is replaced by Trc promoter Carry out a shake-flask fermentation trial with the recombinant strains with different genotypes, obtained form the strains integrated with pTrc-nanKM gene cassette, of which the natural endogenous promoter of the glmS and nagB genes are replaced and/or deleted to transform wecB/pTrc99A plasmid, or the natural endogenous promoter of the wecB gene is replaced by Trc promoter. Transfer the monoclonal strain freshly cultivated in culture medium of the LB plate, inoculate into a test tube (13×150 mm) containing 3 mL of the LB broth culture medium, and shake-cultivate at 30° C. for 8 h. Then transfer the seed culture solution, inoculate in 3% into a 250-mL shake-flask containing 50 mL of the fermentation culture solution (M9 culture solution). The initial $OD_{600}$ is approximately 0.5; shake-cultivate at 37° C. and 225 rpm. The fermentation cycle is 72 h. At 24 h and 48 h, adjust to pH 7.0 with 10M NaOH. According to glucose consumption in the fermentation broth, add 65% glucose solution to maintain a glucose concentration of 20 g/L. After completion of fermentation, transfer 1 mL of the fermentation broth and centrifugate. Measure the content of N-Acetyl-D-Glucosamine by HPLC method.

See Table 12 for the output from shake-flask fermentation. The results show that: Compared with the reference strains AT-011 or AT-013, the output of N-Acetyl-D-Glucosamine is increased obviously by recombinant strain with transformed wecB/pTrc99A, and is increased more greatly by recombinant strain with wecB promoter replaced by Trc promoter.

TABLE 12

Output from Shake-flask Fermentation by Recombinant Strains with Transformed wecB/pTrc99A Plasmid or with wecB promoter replaced by Trc Promoter

| species | Output of N-Acetyl-D-Glucosamine (g/L) |
|---|---|
| AT-011 (Reference) | 21.4 ± 1.5 |
| AT-022 (AT-011, wecB/pTrc99A) | 27.3 ± 1.8 |
| AT-023 (AT-011,• wecB promotor::Trc promoter) | 31.6 ± 2.2 |
| AT-013 (Reference) | 21.4 ± 1.6 |
| AT-024 (AT-013, wecB/pTrc99A) | 27.0 ± 1.7 |
| AT-025 (AT-013,• wecB promotor::Trc promoter) | 31.9 ± 2.5 |

EXAMPLE 10

This implementation example describes influences of the *Escherichia coli* strains integrated with pTrc-nanKM gene cassette on the output of N-Acetyl-D-Glucosamine, of which the natural endogenous promoter of the glmS gene and nagB gene is replaced and/or deleted and the natural endogenous promoter of the nanE gene is replaced by Trc promoter to transform nanE/pTrc99A plasmid, or the natural endogenous promoter of the wecB gene is replaced by Trc promoter 1. *Escherichia coli* strains integrated with pTrc-nanKM cassette, of which the natural endogenous promoter of the nagB gene is replaced by Trc promoter and the natural endogenous promoter of the glmS gene is deleted, and the natural endogenous promoter of the NanE gene is replaced by Trc promoter, are used to transform wecB/pTrc99A Preparation of competence: Transform wecB/pTrc99A plasmid with $CaCl_2$ into *Escherichia coli* strain AT-015 integrated with pTrc-NanKM gene cassette, of which the natural endogenous promoter of the nagB gene is replaced by Trc promoter and the natural endogenous promoter of the glmS gene is deleted, and the natural endogenous promoter of the nanE gene is replaced by Trc promoter, pick up monoclones and cultivate, and pipet plasmid to identify positive clones.

No. of the obtained strain: AT-026 (AT-015, wecB/pTrc99A).

2. In *Escherichia coli* strains integrated with pTrc-nanKM cassette, of which the natural endogenous promoter of the nagB gene is replaced by Trc promoter and the natural endogenous promoter of the glmS gene is deleted, and the natural endogenous promoter of the NanE gene is replaced by Trc promoter, the natural endogenous promoter of the wecB gene is replaced by Trc promoter First, pKD46 carrier is introduced into the AT-015 strain of *Escherichia coli*. Then, the prepared linear DNA segment for targeting is electrotransformed, and positive clones are screened. Finally, the resistance gene is removed.

No. of the obtained strain: AT-027 (AT-015, wecB promotor::Trc promoter).

3. *Escherichia coli* strains integrated with pTrc-nanKM cassette, of which the natural endogenous promoter of the glmS gene is replaced by Trc promoter and the natural endogenous promoter of the nagB gene is deleted, and the natural endogenous promoter of the NanE gene is replaced by Trc promoter, are used to transform wecB/pTrc99A Preparation of competence: Transform wecB/pTrc99A plasmid with CaCl$_2$ into *Escherichia coli* strain AT-017 integrated with pTrc-NanKM gene cassette, of which the natural endogenous promoter of the glmS gene is replaced by Trc promoter and the natural endogenous promoter of the nagB gene is deleted, and the natural endogenous promoter of the nanE gene is replaced by Trc promoter, pick up monoclones and cultivate, and pipet plasmid to identify positive clones.

No. of the obtained strain: AT-028 (AT-017, wecB/pTrc99A).

4. In *Escherichia coli* strains integrated with pTrc-nanKM cassette, of which the natural endogenous promoter of the glmS gene is replaced by Trc promoter and the natural endogenous promoter of the nagB gene is deleted, and the natural endogenous promoter of the NanE gene is replaced by Trc promoter, the natural endogenous promoter of the wecB gene is replaced by Trc promoter First, pKD46 carrier is introduced into the AT-017 strain of *Escherichia coli*. Then, the prepared linear DNA segment for targeting is electrotransformed, and positive clones are screened. Finally, the resistance gene is removed.

No. of the obtained strain: AT-029 (AT-017, ▸ wecB promotor::Trc promoter).

5. Influences of the *Escherichia coli* strains integrated with pTrc-nanKM gene cassette on the output of N-Acetyl-D-Glucosamine, of which the natural endogenous promoter of the nagB gene and glmS gene is replaced and/or deleted and the natural endogenous promoter of the nanE gene is replaced by Trc promoter to transform nanE/pTrc99A plasmid, or the natural endogenous promoter of the wecB gene is replaced by Trc promoter Carry out a shake-flask fermentation trial with recombinant strains, produced from *Escherichia coli* strains integrated with pTrc-nanKM cassette, of which the natural endogenous promoter of the glmS gene and nagB gene is replaced or deleted, and the natural endogenous promoter of the NanE gene is replaced by Trc promoter to transform wecB/pTrc99A plasmid, and wecB promoter is replaced by Trc promoter. Transfer the monoclonal strain freshly cultivated in culture medium of the LB plate, inoculate into a test tube (13×150 mm) containing 3 mL of the LB broth culture medium, and shake-cultivate at 30° C. for 8 h. Then transfer the seed culture solution, inoculate in 3% into a 250-mL shake-flask containing 50 mL of the fermentation culture solution (M9 culture solution). The initial OD$_{600}$ is approximately 0.5; shake-cultivate at 37° C. and 225 rpm. The fermentation cycle is 72 h. At 24 h and 48 h, adjust to pH 7.0 with 10M NaOH. According to glucose consumption in the fermentation broth, add 65% glucose solution to maintain a glucose concentration of 20 g/L. After completion of fermentation, transfer 1 mL of the fermentation broth and centrifugate. Measure the content of N-Acetyl-D-Glucosamine by HPLC method.

See Table 13 for the output from shake-flask fermentation. The results show that: Compared with the reference strains AT-015 or AT-017, the output of N-Acetyl-D-Glucosamine is increased obviously by recombinant strain with transformed wecB/pTrc99A, and is increased more greatly by recombinant strain with wecB promoter replaced by Trc promoter.

TABLE 13

Output from Shake-flask Fermentation by Recombinant Strains with Transformed wecB/pTrc99A Plasmid or with wecB promoter replaced by Trc Promoter

| species | Output of N-Acetyl-D-Glucosamine (g/L) |
|---|---|
| AT-015 (Reference) | 29.5 ± 1.6 |
| AT-026 (AT-015, wecB/pTrc99A) | 34.8 ± 1.7 |
| AT-027 (AT-015,▸ wecB promotor::Trc promoter) | 39.5 ± 2.5 |
| AT-017 (Reference) | 30.5 ± 1.7 |
| AT-028 (AT-017, wecB/pTrc99A) | 35.3 ± 1.6 |
| AT-029 (AT-017,▸ wecB promotor::Trc promoter) | 39.9 ± 2.3 |

EXAMPLE 11

This implementation example describes a fermentation trial for production of N-Acetyl-D-Glucosamine by 10-L fermentation tank Carry a fermentation trial for production of N-Acetyl-D-Glucosamine by 10-L fermentation tank, using recombinant engineering strain AT-029 as production strain.

1. Seed Cultivation (1) Cultivation of Primary Seed: Pick monoclonal strain freshly cultivated in the LB plate medium, inoculate into 8 mL of LB broth medium, and shake-cultivate at 37° C. and 225 rpm for 8 h.

(2) Cultivation of Secondary Seed: Transfer 6 mL of the primary seed culture solution, inoculate into 1000-mL shake flask containing 200 mL of M9 culture solution, and shake-cultivate at 37° C. and 225 rpm for 16 h, until OD$_{600}$ value is 6.0-10, approximately the medium stage of log growth.

(3) Prepare the fermentation medium according to Table 14, where the microelement solution is prepared according to Table 15, and the complex vitamins solution is prepared according to Table 16.

TABLE 14

Fermentation Medium

| Ingredients | Amount (/L) |
|---|---|
| K$_2$HPO$_4$ | 1.30 g |
| KH$_2$PO$_4$ | 1.00 g |
| MgSO$_4$•7H$_2$O | 0.10 g |
| NH$_4$Cl | 0.02 g |
| (NH$_4$)$_2$SO$_4$ | 0.20 g |
| NaH$_2$PO$_4$ | 0.60 g |
| Polyether Defoamer | 10 mL |
| Microelement Solution | 4 ml |
| Complex Vitamins Solution | 4 ml |
| Glucose | 6.00 g |

NOTE:
① The microelement solution is sterilized separately and then added, and the vitamins solution is filtered and then added;
② Glucose: Concentration 65% (w/v); it is sterilized separately and is added prior to inoculation. Amount to be added: 6.0 g/L;
③ The above solutions are combined, and then adjust to pH 7.0 with 10M NH$_4$OH;
④ The fermentation medium is a basal medium prior to addition of glucose; initial loading amount of the basal medium (initial volume accounting for the total capacity of the fermentation tank): 50%.

TABLE 15

Microelement Solution

| Ingredients | Amount used (g/L) |
|---|---|
| $CaCl_2 \cdot 2H_2O$ | 10 |
| $FeCl_3 \cdot 6H_2O$ | 10 |
| $MnSO_4 \cdot 5H_2O$ | 2.5 |
| $AlCl_3 \cdot 6H_2O$ | 2.5 |
| $CoCl_2 \cdot 6H_2O$ | 1.75 |
| $ZnSO_4 \cdot 2H_2O$ | 0.5 |
| $NaMoO_4 \cdot 2H_2O$ | 0.5 |
| $CuSO_4 \cdot 5H_2O$ | 0.25 |
| $H_3BO_3$ | 0.125 |
| pH | 3 to 4 |

TABLE 16

Complex Vitamins Solution

| Ingredients | Amount (mg/L) |
|---|---|
| Folic Acid | 2 |
| Vitamin $B_2$ Riboflavin | 100 |
| Vitamin $B_1$ Thiamine HCl | 1500 |
| Nicotinic Acid | 500 |
| Vitamin $B_6$ Pyridoxine HCl | 500 |
| Calcium Pantothenate, Ca-panthothenate | 500 |
| Biotin | 1 |
| Vitamin $B_{12}$ | 10 |

2. Inoculation

Inoculate the secondary seed solution to the fermentation tank in the ratio of 40 mL/L; inoculation size: 2.5-5% (v/v); the initial $OD_{600}$ is 0.3-0.5.

3. Process Parameters

Carry out a high-density fermentation by 10-L self-control fermentation tank, and collect data by software equipped in the machine to realize online control by computer. The control parameters are: The air flow is 0.5-1 vvm.; dissolved oxygen is >=20%, to increase regulation of rotational speed and ventilation; temperature 37° C.; pH 7.0, the automatic flow is maintained stable by addition of saturated ammonia water. Supplement glucose when glucose in the basal medium is consumed up, i.e. dissolved oxygen is risen again. Glucose is supplemented in a speed to control residual glucose concentration is not more than 0.45 g/L. The glucose-supplementing solution contains 65% (w/v) of glucose, is added with 2.5% Sodium Gluconate or 6% Ribose. The fermentation is stopped after 60-72 h. Total loading amount: 75%-80%.

4. Example (10-L fermentation tank)

(1) Strain No.: AT-029. Batch No.: 0072.

(2) Concentration of Seed Solution: $OD_{600}$为 2.7.

(3) Base Stock: 4 L.

(4) Inoculation Size 200 mL.

(5) Glucose supplementation speed: The residual glucose concentration is controlled as not more than 0.45 g/L.

(6) Glucose-supplementing solution: The solution contains glucose in a concentration of 65% (w/v) and is added with 2.5% sodium gluconate.

(7) Track Indicators: Measure $OD_{600}$ and residual glucose content (residual glucose in the fermentation solution).

(8) Product: N-Acetyl-D-Glucosamine. Potency: 72 h, 145.5 g/L.

EXAMPLE 12

This implementation example describes the processing process after separation and purification of N-Acetyl-D-Glucosamine and D-Glucosamine Hydrochloride 1. Refinement of N-Acetyl-D-Glucosamine (1) Deactivation: The fermentation solution is placed at 80° C. for 30 min.

(2) Solid-liquid separation: Centrifugate at 4000-8000 rpm, discard the bacterial residue and proteins, and transfer the fermentation solution. It may also be filtered via ceramic membrane.

(3) Decoloration: Product:Water:Activated Charcoal=1: (1.5-3):(0.01-0.1); stir for 0.5-5 h.

(4) Desalt: Desalt by electroosmosis. Initial salt concentration of the fermentation loaded into the concentrated chamber tank: 0.01-0.05 mol/L. Flow rate of the dilute-chamber fermentation solution: 40-80 L/h; flow rate of the concentrated-chamber fermentation solution: 40-80 L/h; the voltage of single membrane pair is 0.5-1.4 V. It may also be desalted by anion or cation ion exchange resin.

(5) Concentration: The fermentation solution desalted is heated at 50-80° C. under vacuum conditions (0.095 MPa) for 8-15 h until oversaturation, by approximately 4-6 folds.

(6) Concentration: The concentrated fermentation solution is cooled to 25-35° C. in water at 25° C., then cooled for 1-3 h to 0-10° C. in water at 0° C. Add anhydrous alcohol (in an amount of approximately 5-20 times the product weight), and stir at 700-1500 rpm for 15 min-1 h.

(7) Washing: Add anhydrous alcohol (same amount as that of the product) and stir for 10-100 rpm, 0.5-2 h.

(8) Drying: 50-100° C., 3-10 h. Purity: 99.93%. The total yield is 91.1%.

2. Refinement of D-Glucosamine Hydrochloride (1) Deactivation: The fermentation solution is placed at 80° C. for 30 min.

(2) Solid-liquid separation: Centrifugate at 4000-8000 rpm, discard the bacterial residue and proteins, and transfer the fermentation solution. It may also be filtered via ceramic membrane.

(3) Decoloration: Product:Water:Activated Charcoal=1: (1.5-3):(0.01-0.1); stir for 0.5-5 h.

(4) Desalt: Desalt by electroosmosis. Initial salt concentration of the fermentation loaded into the concentrated chamber tank: 0.01-0.05 mol/L. Flow rate of the dilute-chamber fermentation solution: 40-80 L/h; flow rate of the concentrated-chamber fermentation solution: 40-80 L/h; the voltage of single membrane pair is 0.5-1.4 V. It may also be desalted by anion or cation ion exchange resin.

(5) Concentration: The fermentation solution desalted is heated at 50-80° C. under vacuum conditions (0.095 MPa) for 8-15 h until oversaturation, by approximately 4-6 folds.

(6) Hydrolysis: Introduce the concentrated fermentation solution to an enamel or glass container, add concentrated hydrochloric acid (37%) to a final concentration of 12%46%, stir thoroughly, and maintain at 70° C. for 90 min. Hydrochloric Acid may be used in a recycling way.

(7) Crystalliation: First cool to 25-35° C. in water at 25° C., and then cool to 4° C. in water at 0° C. for 1-3 h.

(8) Washing: Add anhydrous alcohol (same amount as that of the product) and stir for 10-100 rpm, 0.5-2 h. Centrifugate at 700-1500 rpm for 15-60 min to obtain Glucosamine Hydrochloride; the conversion rate is 90.2%.

(9) Dissolution: Dissolve the washed product in water in an similar volume to that of the original fermentation solution.

(10) Decoloration: Add activated charcoal (in an amount of 1%). Mix for 30 min. Then centrifugate at 700-1500 rpm for 15-60 min. Or filter to obtain a colorless filtrate.

(11) Recrystallisation: Evaporate at 50° C. and 55 cmHg vacuum until oversaturation. Add anhydrous alcohol (in an amount of approximately 5-20 times the product weight), and stir at 700-1500 rpm for 15 min-1 h.

(12) Washing: Add anhydrous alcohol (same amount as that of the product) and stir for 10-100 rpm, 0.5-2 h. Then centrifugate at 700-1500 rpm for 15-60 min.

(13) Drying: 50-100° C., 3-10 h. Purity: 99.91%. The total yield is 83.8%.

EXAMPLE 13

This implementation example describes screening for a gene mutant of N-Acetyl-D-Mannosamine-6-P Epimerase (NanE); the said gene encodes N-Acetyl-D-Mannosamine-6-P Epimerase (NanE) with increased activities.

To further increase synthetic quantity of N-Acetyl-D-Glucosamine by the production strain, screen a gene mutant encoding the enzyme with increased activities. To achieve the purpose, amplify the cloned gene by error-prone PCR technology; used for amplified DNA polymerase, amplify the said gene under conditions leading to high-frequency mismatch, so as to obtain a high-frequency mutation in PCR products.

The specific operating process is provided below:

1. Amplification of the Gene nanE of N-Acetyl-D-Mannosamine-6-P Epimerase in *Escherichia coli* by Error-Prone PCR By means of Taq DNA polymerase without the property of 3'-5' proofreading function, control the frequency of random mutation under high magnesium ion concentration (8 mmol/L) and different dNTP concentrations (where, the concentration of dATP and dGTP is 1.5 mmol/L; and the concentration of dTTP and dCTP is 3.0 mmol/L), introduce random mutations into the target gene, and construct a mutant library; the template concentration A260 value is 1000 ng/mL, the enzyme concentration is 5 U/μL, and the primer concentration is 100 μM.

Error-prone PCR reaction system (50 μL): 10×PCR reaction buffer 5 μl, dNTP (2.5 mM) 5 μL, MgCl$_2$ (2.5 mM) 5 μL, Forward primer (nanE-F, SEQ ID No.30) 1 μL, reverse primer (nanE-R, SEQ ID No.31) 1 μL, DNA template (nanE/pUC57) 0.1 μL, Taq DNA polymerase 0.5 μL, and ddH$_2$O 32.4 μL.

PCR procedure: Predegenerate at 96° C. for 4 min; degenerate at 94° C. for 1 min, anneal at 56° C. for 1 min, extend at 75° C. for 2 min, and repeat for 45 cycles; finally extend at 75° C. for 15 min, recover PCR product (product size: 0.7 kb) by gel recovery method; transfer 5 μL of the product and carry out 1% agarose gel electrophoresis test; the product is store at −20° C. for use.

2. Construction of the Gene Mutant Library of N-Acetyl-D-Mannosamine-6-P Epimerase Digest the above PCR product by two enzymes of restriction endonuclease Nco I and Hind III, carry out a ligation reaction with pTrc99A digested by Nco I and Hind III, then transform *Escherichia coli* AT-005-02 with the mixture of the ligated products to obtain a large amount of cloned transformants, and construct a mutant library of transformed thalli.

3. Screening for Mutants with High Enzyme Activities

Using the wild type NanE/pTrc99A (AT-005-02) as reference, pick up randomly 350 mutant clones from the mutant library of transformed thalli, inoculate into 5 mL of LB medium containing 50 μg/mL Ampicillin (Amp), shake-cultivate at 37° C. and 150 rpm for 18 h, and then centrifugate at 10000 rpm for 5 mim and collect thalli. Discard the supernatant, then resuspend at 4° C. in 1 mL of PBS solution (pH 7.5, 10 mmol/L), carry out ultrasonicate at a voltage of 300 V for 10 min (ultrasonicate for 3 s and pause for 6 s), centrifugate, transfer the supernatant as crude extract of enzyme, and carry out a method for determination of enzyme activity.

Determination of N-Acetyl-D-Mannosamine-6-P Epimerase Activity: Based on the amount of N-Acetyl-D-Mannosamine-6-Phosphate (ManNAc-6-P) transformed into N-Acetyl-D-Glucosamine-6-Phosphate (GlcNAc-6-P); that is to say, using the reduced amount of N-Acetyl-D-Mannosamine-6-Phosphate as test marker. Definition of Enzyme Activity Unit: Under the enzymatic reaction conditions, the enzyme amount reduced, equivalent to 1 μmol N-Acetyl-D-Mannosamine-6-Phosphate per minute, is defined as one enzyme activity unit (IU). The specific procedure is provided as follows: First, prepare isotope-labelled ManNAc-6-P as substrate. Prepare a reaction solution in a total volume of 225 uL, containing ManNAc Kinase (NanK) crude solution (containing 1-5 mg protein), 20 mM ATP disodium, 60 mM Tris-HCl, pH8.1, 20 mM MgCl$_2$, 5 mM ManNAc, and 50 nCi [$^{14}$C]ManNAc. Incubate at 37° C. for 30 min. Add 350 uL of alcohol to stop the reaction. The product is eluted and lyophilized with water. Secondly, prepare a reaction solution in a total volume of 26.5 uL as the determination system for enzyme activity, containing 1 mM isotope-labelled ManNAc-6-P, 37 mM Tris-HCl, pH 8.0, and 19 mM MgCl$_2$. Incubate at 37° C. for 30 min, heat the reaction solution to boil for 3 min, then add 0.1 volume of alkaline phosphatase buffer to adjust pH and 20 U of alkaline phosphatase. Incubate at 37° C. for 1 h, draw a sample and add on a dry chromatography paper, and presoak with 1% sodium tetraborate. The used solvent system is a mixture of ethyl acetate:isopropanol:pyridine:water (50:22:14:14). Separate radioactive compounds by paper chromatography. Measure the radioactive intensity by a liquid scintillation counter, and calculate the activity units of N-Acetyl-D-Mannosamine-6-P Epimerase, based on the amount of ManNAc-6-P transformed into GlcNAc-6-P.

The results show that: The enzyme activity of the mutant strain with maximum activity is 72 IU/mL, and the enzyme activity of the reference is 9.5 IU/mL. Transform NanE by error-prone PCR, to obtain a mutant strain with enzyme activity increased greatly. Pick up the mutant strain with maximum enzyme activity and extract plasmids for sequencing. The results show that: The mutant gene sequence of N-Acetyl-D-Mannosamine-6-P Epimerase is shown as SEQ ID No.56, and the corresponding amino acid sequence is shown as SEQ ID No.57. Through gene sequence alignment with the wild type of N-Acetyl-D-Mannosamine-6-P Epimerase, 3 base point mutations occur in total: 198C/T, 397T/C, and 559T/C. There occur 2 missense mutations of amino acids, of which the mutation points are: Q133R (cysteine at Site 133 is replaced by arginine), and Y187H (tyrosine at Site 187 is replaced by histidine). The mutant gene is named as nanEM.

4. Integration of pTrc-nanEM Gene Cassette into the nagE Gene Site in the Chromosome of *Escherichia coli*

Using the nagE gene site as integration site of pTrc-nanEM gene cassette into the chromosome. To achieve integration of pTrc-nanEM gene cassette into the chromosome of *Escherichia coli*, first amplify the nanEM segment (i.e. pTrc-nanEM) of Trc promoter, as well as the kanamycin resistance gene segment with FLP recognition site (FRT site)

at its both ends: FRT-Kanr-FRT (fKanrf), and splice them. Then design homologous primers for deletion of the nagE gene sequence, and using the spliced segment of pTrc-nanEM and fKanrf as template, amplify the linear DNA full-length segment for targeting of Red recombination.

The specific operating process is provided below:

(1) PCR Amplification of pTrc-nanEM Segment

Template: nanEM/pTrc99A.

Primer Design: Forward primer (Trcff-F) SEQ ID No.20, and reverse primer (Trcff-R) SEQ ID No.21.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Product Size: 0.86 kb.

The PCR product is separated by 1% agarose gel electrophoresis, and purified to recover the segment.

(2) PCR Amplification of fKanrf Segment

Primer Design: Forward primer (mfKanf-F) SEQ ID No.1, and reverse primer (mfKanf-R) SEQ ID No.2.

Template: pPic9K.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

fKanrf size: 1.28 kb. Its nucleotide sequence is SEQ ID No.3.

The PCR product is separated by 1% agarose gel electrophoresis, and purified to recover the segment.

(3) Amplification of fKanrf Spliced with pTrc-nanEM

Primer Design: Forward primer (fKanf-F) SEQ ID No.22, and reverse primer (fKanf-R) SEQ ID No.23.

Template: fKanrf.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

fKanrf size from secondary amplification: 1.3 kb.

The PCR product is separated by 1% agarose gel electrophoresis, and purified to recover the segment.

(4) Preparation of Linear DNA Full-Length PCR Segment for Targeting of Red Recombination Design of Homologous Arm Primers: Design again homologous arm primers for deletion of the nagE gene sequence: Forward primer (nagEKO-F2) SEQ ID No.24, and reverse primer (nagEKO-R2) SEQ ID No.25.

Template: Mix pTrc-nanEM PCR segment, and fKanrf PCR segment from secondary amplification in the ratio of 1:1.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product: Homologous Arm+pTrc-nanEM-fKanrf+Homologous Arm

The PCR product is separated by agarose gel electrophoresis, and purified and recovered to obtain 100 ng/μL linear DNA full-length PCR segment for targeting of Red recombination.

(5) Red Recombination Operation

First, pKD46 carrier is introduced into the AT-004-02 strain of *Escherichia coli*. Then, the prepared linear DNA segment for targeting is electrotransformed, and positive clones are screened. Finally, the resistance gene is removed.

1) Transformation of pKD46 Plasmid

① Preparation of Competence: First, inoculate the bacterial suspension of *Escherichia coli* AT-004-02 stored at −20° C. into 10 mL of LB broth medium in a ratio of 1:50-100, and shake-cultivate at 37° C. and 225 rpm for 2-3 h. Then add the culture solution to a 10-mL centrifuge tube, centrifugate at 4000 g×5 min, discard the supernatant, and suspend with 5 mL 0.1M $CaCl_2$ on an ice bath for 5 min. Finally, centrifugate at 4000 g×5 min, discard the supernatant, and suspend with 5 mL of 0.1M $CaCl_2$ on an ice bath. Allow to stand at −4° C. for 12 h for spontaneous sedimentation.

② Plasmid Transformation: Transfer 250 μL of spontaneously sedimented thalli, add 5 μL of pKD46 plasmid, and cultivate at −4° C. for 30 min. Then heat on a water bath at 42° C. for 1.5 min, add 0.7 mL of SOC medium, and shake at 30° C. for 2 h. Transfer 0.2 mL of the bacterial suspension, and smear on a penicillin plate. Cultivate overnight (for 12-16 h) at 30° C. Pick up monoclone, add 5 mL of LB broth medium and cultivate, and withdraw plasmid for identification. Store the positive strain for use.

2) Electrotransform Linear DNA Segment for Targeting, and Screen Positive Clone

① Preparation of Electrotransformed Competence: Inoculate the AT-004-02 strain of *Escherichia coli*, containing pKD46, into a test tube of LB medium containing Ampicillin (Amp), and shake-cultivate at 250 rpm; on the next day, inoculate in a ratio of 1% into LB medium containing Amp, and cultivate at 30° C.; when OD600 reaches approximately 0.2, add 0.2% L-Arabinose, and induce at 30° C. for 35 min until $OD_{600}$ reaches approximately 0.4. Cool on an ice bath. Wash once with ultrapure water, wash twice with 10% glycerin, and finally resuspend with 10% glycerin; the amount of glycerin used is to produce a final concentration of the thalli concentrated by 500-1000 folds.

② Transformation by electric shock: Take out a 2-mm electrotransformation cup from 70% ethanol, wash with sterilized ultrapure water, and irradiate by UV lamp for 30 min. Precool at 4° C. for 30 min. Transfer 90 μL of finally resuspended cells to a precooled centrifuge tube, add 5 μL (more than 100 ng) of the full-length PCR segment (linear DNA) obtained in Step (4), suction gently by a gun, and maintain on an ice bath for 30 min. Electrotransformation Parameters: 2500V, 200Ω, 25 μF.

③ Resuscitate and screen positive clones: add 1 mL of LB broth medium, and cultivate at 37° C. and 100 rpm for 1 h. Then smear one kanamycin (Kan) plate with every 200 μL, 5 plates in total. Smear evenly and allow to air-dry. Cultivate at 30° C. for 24 h. Pick up clones grown under kanamycin resistance, and carry out PCR identification to screen positive clones.

No. of the obtained strain: AT-031-01 (AT-004-02, ▸ nagE::pTrc-nanEM-fKanrf).

As described above, prepare the strain AT-030-01 (AT-004-02, ▸ nagE::pTrc-nanE-fKanrf).

(6) Removal of the Resistance Gene

Introduce pCP20 into the above kanamycin-resistant clones, cultivate at 30° C. for 8 h, then increase to 42° C. and cultivate overnight, and thermally induce to express FLP recombinase; the plasmids are lost gradually. Streak the plate of antibiotics-free culture medium by an inoculating loop dipped in the bacterial suspension, pick up grown monoclones and dot on the kanamycin-resistant plate; those that cannot grown are clones of which the kanamycin resistance gene has been removed by FLP recombination. Carry out PCR with identification primer to identify clones losing kanamycin resistance.

No. of the obtained strain: AT-031-02 (AT-004-02, ▸ nagE::pTrc-nanEM).

As described above, prepare the strain AT-030-02 (AT-004-02, ▸ nagE::pTrc-nanE).

5. Influence of the Integration of pTrc-nanE and pTrc-nanKM Gene Cassettes on the Output of N-Acetyl-D-Glucosamine Carry out a shake-flask fermentation trial with the recombinant strains AT-030-02 and AT-031-02, of which the nagE gene site in the chromosome is integrated with pTrc-nanE and pTrc-nanEM gene cassettes, and the reference strain. Transfer the monoclonal strain freshly cultivated in culture medium of the LB plate, inoculate into a test tube (13×150 mm) containing 3 mL of the LB broth culture medium, and shake-cultivate at 30° C. for 8 h. Then transfer the seed culture solution, inoculate in 3% into a 250-mL shake-flask containing 50 mL of the fermentation culture solution (M9 culture solution). The initial OD600 is approximately 0.5; shake-cultivate at 37° C. and 225 rpm. The fermentation cycle is 72 h. At 24 h and 48 h, adjust to pH 7.0 with 10M NaOH. According to glucose consumption in the fermentation broth, add 65% glucose solution to maintain a glucose concentration of 20 g/L. After completion of fermentation, transfer 1 mL of the fermentation broth and centrifugate. Measure the content of N-Acetyl-D-Glucosamine by HPLC method.

See Table 17 for the output from shake-flask fermentation. The results show that: The output by the reference strain AT-005-02 is very low and is not detected, while the output by the recombinant strain AT-031-02 integrated with pTrc-nanEM gene cassette is increased obviously, and is also increased significantly than that by the unmutant reference strain AT-030-02.

TABLE 17

Output from Shake-flask Fermentation by the Recombinant Strain integrated with pTrc-nanEM Gene Cassette

| species | Output of N-Acetyl-D-Glucosamine (g/L) |
|---|---|
| AT-005-02 (AT-004-02,▸ nagE) (Reference) | Not detected |
| AT-030-02 (AT-004-02,▸ nagE::pTrc-nanE) | 2.6 ± 0.5 |
| AT-031-02 (AT-004-02,▸ nagE::pTrc-nanEM) | 5.9 ± 0.8 |

The above results show that: The output of N-Acetyl-D-Glucosamine may be increased obviously by overexpression of N-Acetyl-D-Mannosamine-6-P Epimerase; moreover, the output of N-Acetyl-D-Glucosamine may also be greatly by the mutant screened by error-prone PCR technology, due to increased activities of the obtained mutant of the epimerase.

EXAMPLE 14

This implementation example describes screening for a gene mutant of UDP-N-AcetylGlucosamine-2-Epimerase (WecB); the said gene encodes UDP-N-AcetylGlucosamine-2-Epimerase (WecB) with increased activities.

To further increase synthetic quantity of N-Acetyl-D-Glucosamine by the production strain, screen a gene mutant encoding UDP-N-AcetylGlucosamine-2-Epimerase with increased activities. To achieve the purpose, amplify the cloned gene by error-prone PCR technology; used for amplified DNA polymerase, amplify the said gene under conditions leading to high-frequency mismatch, so as to obtain a high-frequency mutation in PCR products.

The specific operating process is provided below:
1. Amplification of UDP-N-AcetylGlucosamine-2-Epimerase Gene wecB by Error-Prone PCR.

By means of Taq DNA polymerase without the property of 3'-5' proofreading function, control the frequency of random mutation under high magnesium ion concentration (8 mmol/L) and different dNTP concentrations (where, the concentration of dATP and dGTP is 1.5 mmol/L; and the concentration of dTTP and dCTP is 3.0 mmol/L), introduce random mutations into the target gene, and construct a mutant library; the template concentration A260 value is 1000 ng/mL, the enzyme concentration is 5 U/µL, and the primer concentration is 100 µM.

Error-prone PCR reaction system (50 µL): 10×PCR reaction buffer 5 µl, dNTP (2.5 mM) 5 µL, MgCl$_2$ (2.5 mM) 5 µL, Forward primer (TrcwecB-F, SEQ ID No.51) 1 µL, reverse primer (TrcwecB-R, SEQ ID No.52) 1 µL, DNA template (wecB/pUC57) 0.1 µL, Taq DNA polymerase 0.5 µL, and ddH$_2$O 32.4 µL.

PCR procedure: Predegenerate at 96° C. for 4 min; degenerate at 94° C. for 1 min, anneal at 56° C. for 1 min, extend at 75° C. for 2 min, and repeat for 45 cycles; finally extend at 75° C. for 15 min, recover PCR product (product size: 1.13 kb) by gel recovery method; transfer 5 µL of the product and carry out 1% agarose gel electrophoresis test; the product is store at −20° C. for use.

2. Construction of the Gene Mutant Library of UDP-N-AcetylGlucosamine-2-Epimerase Digest the above PCR product by two enzymes of restriction endonuclease Nco I and Hind III, carry out a ligation reaction with pTrc99A digested by Nco I and Hind III, then transform *Escherichia coli* AT-005-02 with the mixture of the ligated products to obtain a large amount of cloned transformants, and construct a mutant library of transformed thalli.

3. Screening for Mutants with High Enzyme Activities

Using the wild type WecB/pTrc99A (AT-005-02) as reference, pick up randomly 640 mutant clones from the mutant library of transformed thalli, inoculate into 5 mL of LB medium containing 50 µg/mL Ampicillin (Amp), shake-cultivate at 37° C. and 150 rpm for 18 h, and then centrifugate at 10000 rpm for 5 mim and collect thalli. Discard the supernatant, then resuspend at 4° C. in 1 mL of PBS solution (pH 7.5, 10 mmol/L), carry out ultrasonicate at a voltage of 300 V for 10 min (ultrasonicate for 3 s and pause for 6 s), centrifugate, transfer the supernatant as crude extract of enzyme, and carry out a method for determination of enzyme activity.

Determination of UDP-N-AcetylGlucosamine-2-Epimerase Activity: Based on the amount of UDP-N-Acetyl-D-Glucosamine transformed into N-Acetyl-D-Mannosamine. That is to say, the reduced amount of UDP-N-Acetyl-D-Glucosamine is used as test marker. Definition of Enzyme Activity Unit: Under the enzymatic reaction conditions, the enzyme amount reduced, equivalent to 1 µmol UDP-N-Acetyl-D-Glucosamine per minute, is defined as one enzyme activity unit (IU). The specific procedure is provided as follows: Transfer 20 mL of the reaction system as the system for determination of enzyme activity, which contains 45 mmol/L phosphate buffer (pH7.5), 10 mM MgCl2 and 100 nCi of UDPGlcNAc, and 5 mg crude enzyme solution. Carry out the enzyme activity reaction by incubating on a water bath at 37° C. for 30 min. Add alcohol to stop the reaction. Separate radioactive compounds by paper chromatography. Measure the radioactive intensity by a liquid scintillation counter. The solvent system used is a mixture of n-propanol:1M sodium acetate, pH 5.0:water (7:1:2). Calculate the activity units of UDP-N-AcetylGlucosamine-2-Epimerase, based on the amount of UDPGlcNAc transformed into ManNAc.

The results show that: The enzyme activity of the mutant strain with maximum activity is 653 IU/mL, and the enzyme activity of the reference is 21.0 IU/mL. Transform WecB by error-prone PCR, to obtain a mutant strain with enzyme activity increased greatly. Pick up the mutant strain with maximum enzyme activity and extract plasmids for sequencing. The results show that: The mutant gene sequence of UDP-N-AcetylGlucosamine-2-Epimerase is shown as SEQ ID No.58, and the corresponding amino acid sequence is shown as SEQ ID No.59. Compared with gene sequence of the wild type UDP-N-AcetylGlucosamine-2-Epimerase, 5 base point mutations occur in total: 101G/C, 433C/G, 677G/T, 734T/G, and 1038T/C; There occur 4 missense mutations of amino acids, of which the mutation points are: C34S (cysteine at Site 34 is replaced by serine), H145D (histidine at Site 145 is replaced by aspartate), C226F (cysteine at Site 226 is replaced by phenylalanine), and V245G (valine at Site 245 is replaced by glycine). The mutant gene is named as wecBM.

4. Integration of pTrc-wecBM Gene Cassette into the nagE Gene Site in the Chromosome of *Escherichia coli*

Using the nagE gene site as integration site of pTrc-wecBM gene cassette into the chromosome. To achieve integration of pTrc-wecBM gene cassette into the chromosome of *Escherichia coli*, first amplify the wecBM segment (i.e. pTrc-wecBM) of Trc promoter, as well as the kanamycin resistance gene segment with FLP recognition site (FRT site) at its both ends: FRT-Kanr-FRT (fKanrf), and splice them. Then design homologous primers for deletion of the nagE gene sequence, and using the spliced segment of pTrc-wecBM and fKanrf as template, amplify the linear DNA full-length segment for targeting of Red recombination.

The specific operating process is provided below:

(1) PCR Amplification of pTrc-wecBM Segment

Template: wecBM/pTrc99A.

Primer Design: Forward primer (Trcff-F) SEQ ID No.20, and reverse primer (Trcff-R) SEQ ID No.21.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Product Size: 1.3 kb.

The PCR product is separated by 1% agarose gel electrophoresis, and purified to recover the segment.

(2) PCR Amplification of fKanrf Segment

Primer Design: Forward primer (mfKanf-F) SEQ ID No.1, and reverse primer (mfKanf-R) SEQ ID No.2.

Template: pPic9K.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

fKanrf size: 1.28 kb. Its nucleotide sequence is SEQ ID No.3.

The PCR product is separated by 1% agarose gel electrophoresis, and purified to recover the segment.

(3) Amplification of fKanrf Spliced with pTrc-wecBM

Primer Design: Forward primer (fKanf-F) SEQ ID No.22, and reverse primer (fKanf-R) SEQ ID No.23.

Template: fKanrf.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

fKanrf size from secondary amplification: 1.3 kb.

The PCR product is separated by 1% agarose gel electrophoresis, and purified to recover the segment.

(4) Preparation of Linear DNA Full-Length PCR Segment for Targeting of Red Recombination Design of Homologous Arm Primers: Design again homologous arm primers for deletion of the nagE gene sequence: Forward primer (nagEKO-F2) SEQ ID No.24, and reverse primer (nagEKO-R2) SEQ ID No.25.

Template: Mix pTrc-wecBM PCR segment, and fKanrf PCR segment from secondary amplification in the ratio of 1:1.

PCR reaction conditions: Step 1: Degenerate at 94° C. for 1 min; Step 2: Incubate at 94° C. for 30 s, at 55° C. for 30 s, and at 72° C. for 40 s, and carry out 30 cycles; Step 3: Extend at 72° C. for 10 min.

Amplification Product: Homologous Arm+pTrc-wecBM-fKanrf+Homologous Arm

The PCR product is separated by agarose gel electrophoresis, and purified and recovered to obtain 100 ng/μL linear DNA full-length PCR segment for targeting of Red recombination.

(5) Red Recombination Operation

First, pKD46 carrier is introduced into the AT-004-02 strain of *Escherichia coli*. Then, the prepared linear DNA segment for targeting is electrotransformed, and positive clones are screened. Finally, the resistance gene is removed.

1) Transformation of pKD46 Plasmid

① Preparation of Competence: First, inoculate the bacterial suspension of *Escherichia coli* AT-004-02 stored at−20° C. into 10 mL of LB broth medium in a ratio of 1:50-100, and shake-cultivate at 37° C. and 225 rpm for 2-3 h. Then add the culture solution to a 10-mL centrifuge tube, centrifugate at 4000 g×5 min, discard the supernatant, and suspend with 5 mL 0.1M $CaCl_2$ on an ice bath for 5 min. Finally, centrifugate at 4000 g×5 min, discard the supernatant, and suspend with 5 mL of 0.1M $CaCl_2$ on an ice bath. Allow to stand at −4° C. for 12 h for spontaneous sedimentation.

② Plasmid Transformation: Transfer 250 μL of spontaneously sedimented thalli, add 5 μL of pKD46 plasmid, and cultivate at −4° C. for 30 min. Then heat on a water bath at 42° C. for 1.5 min, add 0.7 mL of SOC medium, and shake at 30° C. for 2 h. Transfer 0.2 mL of the bacterial suspension, and smear on a penicillin plate. Cultivate overnight (for 12-16 h) at 30° C. Pick up monoclone, add 5 mL of LB broth medium and cultivate, and withdraw plasmid for identification. Store the positive strain for use.

2) Electrotransform Linear DNA Segment for Targeting, and Screen Positive Clone

① Preparation of Electrotransformed Competence: Inoculate the AT-004-02 strain of *Escherichia coli*, containing pKD46, into a test tube of LB medium containing Ampicillin (Amp), and shake-cultivate at 250 rpm, on the next day, inoculate in a ratio of 1% into LB medium containing Amp, and cultivate at 30° C.; when $OD_{600}$ reaches approximately 0.2, add 0.2% L-Arabinose, and induce at 30° C. for 35 min until $OD_{600}$ reaches approximately 0.4. Cool on an ice bath. Wash once with ultrapure water, wash twice with 10% glycerin, and finally resuspend with 10% glycerin; the amount of glycerin used is to produce a final concentration of the thalli concentrated by 500-1000 folds.

② Transformation by electric shock: Take out a 2-mm electrotransformation cup from 70% ethanol, wash with sterilized ultrapure water, and irradiate by UV lamp for 30 min. Precool at 4° C. for 30 min. Transfer 90 μL of finally resuspended cells to a precooled centrifuge tube, add 5 μL (more than 100 ng) of the full-length PCR segment (linear DNA) obtained in Step (4), suction gently by a gun, and maintain on an ice bath for 30 min. Electrotransformation Parameters: 2500V, 200Ω, 25 μF.

③ Resuscitate and screen positive clones: add 1 mL of LB broth medium, and cultivate at 37° C. and 100 rpm for 1 h. Then smear one kanamycin (Kan) plate with every 200 μL, 5 plates in total. Smear evenly and allow to air-dry. Cultivate at 30° C. for 24 h. Pick up clones grown under kanamycin resistance, and carry out PCR identification to screen positive clones.

No. of the obtained strain: AT-043-01 (AT-004-02, ▸ nagE::pTrc-wecBM-fKanrf).

As described above, prepare the strain AT-042-01 (AT-004-02, ▸ nagE::pTrc-wecBM-fKanrf).

(6) Removal of the Resistance Gene

Introduce pCP20 into the above kanamycin-resistant clones, cultivate at 30° C. for 8 h, then increase to 42° C. and cultivate overnight, and thermally induce to express FLP recombinase; the plasmids are lost gradually. Streak the plate of antibiotics-free culture medium by an inoculating loop dipped in the bacterial suspension, pick up grown monoclones and dot on the kanamycin-resistant plate; those that cannot grown are clones of which the kanamycin resistance gene has been removed by FLP recombination. Carry out PCR with identification primer to identify clones losing kanamycin resistance.

No. of the obtained strain: AT-043-02 (AT-004-02, ▸ nagE::pTrc-wecBM).

As described above, prepare the strain AT-042-02 (AT-004-02, ▸ nagE::pTrc-wecBM-fKanrf).

5. Influence of the Integration of pTrc-wecB and pTrc-wecBM Gene Cassettes on the Output of N-Acetyl-D-Glucosamine Carry out a shake-flask fermentation trial with the recombinant strains AT-042-02 and AT-043-02, of which the nagE gene site in the chromosome is integrated with pTrc-wecB and pTrc-wecBM gene cassettes, and the reference strain. Transfer the monoclonal strain freshly cultivated in culture medium of the LB plate, inoculate into a test tube (13×150 mm) containing 3 mL of the LB broth culture medium, and shake-cultivate at 30° C. for 8 h. Then transfer the seed culture solution, inoculate in 3% into a 250-mL shake-flask containing 50 mL of the fermentation culture solution (M9 culture solution). The initial $OD_{600}$ is approximately 0.5; shake-cultivate at 37° C. and 225 rpm. The fermentation cycle is 72 h. At 24 h and 48 h, adjust to pH 7.0 with 10M NaOH. According to glucose consumption in the fermentation broth, add 65% glucose solution to maintain a glucose concentration of 20 g/L. After completion of fermentation, transfer 1 mL of the fermentation broth and centrifugate. Measure the content of N-Acetyl-D-Glucosamine by HPLC method.

See Table 18 for the output from shake-flask fermentation. The results show that: The output by the reference strain AT-005-02 is very low and is not detected, while the output by the recombinant strain AT-043-02 integrated with pTrc-wecBM gene cassette is increased obviously, and is also increased significantly than that by the unmutant reference strain AT-042-02.

TABLE 18

Output from Shake-flask Fermentation by the Recombinant Strain integrated with pTrc-wecBM Gene Cassette

| species | Output of N-Acetyl-D-Glucosamine (g/L) |
| --- | --- |
| AT-005-02 (AT-004-02, ▸ nagE) (Reference) | Not detected |
| AT-042-02 (AT-004-02, ▸ nagE::pTrc-wecB) | 7.1 ± 0.8 |
| AT-043-02 (AT-004-02, ▸ nagE::pTrc-wecBM) | 10.9 ± 0.9 |

The above results show that: The output of N-Acetyl-D-Glucosamine may be increased obviously by overexpression of UDP-N-AcetylGlucosamine-2-Epimerase; moreover, the output of N-Acetyl-D-Glucosamine may also be greatly by the mutant screened by error-prone PCR technology, due to increased activities of the obtained mutant of the epimerase.

Although this Invention is described detailedly by common explanations and specific implementation schemes, it may be revised or improved on top of this Invention; this point is as plain as the nose on your face for a technician in this field. Therefore, such revisions or improvements that are not deviated from the spirits of this Invention still fall in the range under protection required by this Invention.

The invention claimed is:

1. A method for production of N-Acetyl-D-Glucosamine and/or D-Glucosamine by microbial fermentation, comprising:
   A) Cultivating of a microorganism in a fermentation medium, where the said microorganism contains at least one genetic modification that may increase the effects of N-Acetyl-D-Mannosamine Kinase in microorganism; and
   B) Collecting N-Acetyl-D-Glucosamine produced in the step A);
   wherein the said genetic modification contains substitutions at the following corresponding sites of SEQ ID NO: 17: substitution of glutamine at Site 36 by arginine, substitution of isoleucine at Site 103 by methionine, and substitution of arginine at Site 223 by serine.

2. The method based on claim 1, wherein the genetic modification that may increase the effects of N-Acetyl-D-Mannosamine Kinase in microorganism is selected from: a) increased effects of N-Acetyl-D-Mannosamine Kinase in microorganism; and/or b) overexpression of N-Acetyl-D-Mannosamine Kinase in microorganism.

3. The method based on claim 2, where the microorganism is transformed by molecules of at least one recombinant nucleic acid, containing one nucleotide sequence encoding N-Acetyl-D-Mannosamine Kinase;
   the nucleic acid sequence encoding N-Acetyl-D-Mannosamine Kinase contains at least one genetic modification increasing the effects of N-Acetyl-D-Mannosamine Kinase.

4. The method based on claim 3, the one nucleic acid sequence encoding N-Acetyl-D-Mannosamine Kinase is SEQ ID NO: 26.

5. The method based on claim 3, at least approximately 30% of the nucleic acid sequence of the said N-Acetyl-D-Mannosamine Kinase is the same as that of SEQ ID NO: 17, wherein the said N-Acetyl-D-Mannosamine Kinase (NanK) is active; and, the said N-Acetyl-D-Mannosamine Kinase has the amino acid sequence of SEQ ID NO: 17.

6. The method based on claim 2, wherein the microorganism contains at least one genetic modification of the natural endogenous promoter to a gene encoding N-Acetyl-D-Mannosamine Kinase; the natural endogenous promoter of the gene encoding N-Acetyl-D-Mannosamine Kinase is replaced by a promoter with higher level; the promoter with higher level is selected from HCE promoter, gap promoter, trc promoter, and T7 promoter; the promoter with higher level is trc promoter.

7. The method based on claim 1, wherein the said microorganism contains one or more of the following genetic modifications:
   (1) Contain at least one genetic modification that may increase the effects of N-Acetyl-D-Mannosamine-6-Phosphate Epimerase in microorganism;
   (2) Contain at least one genetic modification that may increase the effects of D-Glucosamine-6-Phosphate Deaminase in microorganism, or contain at least one genetic modification that may decrease the effects of Glucosamine-6-Phosphate Synthase;
   (3) Contain at least one genetic modification that may increase the effects of D-Glucosamine-6-Phosphate Synthase in microorganism, or contain at least one genetic modification that may decrease the effects of D-Glucosamine-6-Phosphate Deaminase;
   (4) Contain at least one genetic modification that may increase the effects of UDP-N-Acetyl-D-Glucosamine-2-Epimerase (WecB) in microorganism.

8. The method based on claim 7, wherein the genetic modification increasing the effects of UDP-N-Acetyl-D-Glucosamine-2-Epimerase in microorganism is selected from a) increasing the effects of UDP-N-Acetyl-D-Glucosamine-2-Epimerase in microorganism; and/or b) overexpression of UDP-N-Acetyl-D-Glucosamine-2-Epimerase in microorganism.

9. The method based on claim 8, wherein the microorganism is transformed by molecules of at least one recombinant nucleic acid, containing one nucleotide sequence encoding UDP-N-Acetyl-D-Glucosamine-2-Epimerase; the nucleic acid sequence encoding UDP-N-Acetyl-D-Glucosamine-2-Epimerase (WecB) is SEQ ID NO: 58.

10. The method based on claim 1, wherein the said microorganism contains one or more of the following genetic modifications:
    (1) Contain at least genetic modification that may decrease the effects of Mannose transporter EIIM, P/III$^{man}$(ManXYZ) in microorganism;
    (2) Contain at least one genetic modification that may decrease the effects of N-Acetylneuraminate Lyase (NanA) in microorganism;
    (3) Contain at least one genetic modification that may decrease the effects of N-Acetyl-D-Glucosamine-6-Phosphate Deactylase (NagA) in microorganism;
    (4) Contain at least one genetic modification that may decrease the effects of N-Acetyl-D-Glucosamine Specific Enzyme II$^{Nag}$(NagE) in microorganism;
    (5) Contain at least one genetic modification that may increase the effects of PhosphoGlucosamine Mutase (GlmM) in microorganism;
    (6) Contain at least one genetic modification that may increase the effects of bifunctional N-acetyl Glucosamine-1-Phosphate Uridyltransferase (GlmU) in microorganism.

11. The method based on claim 1, wherein the said cultivation step A) is carried at approximately 20° C.~approximately 45° C.; the said cultivation step A) is carried out at approximately pH 4.5~approximately pH 8.5; the said cultivation step A) uses feed-batch fermentation method.

12. The method based on claim 1, wherein the said microorganism is bacteria, yeasts, or fungi.

* * * * *

SEQUENCE LISTING

```
<160> NUMBER OF SEQ ID NOS: 59

<210> SEQ ID NO 1
<211> LENGTH: 70
<212> TYPE: DNA
<213> ORGANISM: Artificial Sequence
<220> FEATURE:
<223> OTHER INFORMATION: Product of the human mind.

<400> SEQUENCE: 1
gtaaaacgac ggccagtgga agttcctata ctttctagag aataggaact tcctcgtgaa    60
gaaggtgttg                                                           70

<210> SEQ ID NO 2
<211> LENGTH: 80
<212> TYPE: DNA
<213> ORGANISM: Artificial Sequence
<220> FEATURE:
<223> OTHER INFORMATION: Product of the human mind
```

```
<400> SEQUENCE: 2
ggaaacagct atgaccatgc ctattccgaa gttcctattc tctagaaagt ataggaactt    60
ctgttacatt gcacaagata                                                80

<210> SEQ ID NO 3
<211> LENGTH: 1283
<212> TYPE: DNA
<213> ORGANISM: Artificial Sequence
<220> FEATURE:
<223> OTHER INFORMATION: Product of the human mind.

<400> SEQUENCE: 3
gtaaaacgac ggccagtgga agttcctata ctttctagag aataggaact tcctcgtgaa    60
gaaggtgttg ctgactcata ccaggcctga atcgccccat catccagcca gaaagtgagg   120
gagccacggt tgatgagagc tttgttgtag gtggaccagt tggtgatttt gaacttttgc   180
tttgccacgg aacggtctgc gttgtcggga agatgcgtga tctgatcctt caactcagca   240
aaagttcgat ttattcaaca aagccgccgt cccgtcaagt cagcgtaatg ctctgccagt   300
gttacaacca attaaccaat tctgattaga aaaactcatc gagcatcaaa tgaaactgca   360
atttattcat atcaggatta tcaataccat attttgaaaa aagccgtttc tgtaatgaag   420
gagaaaactc accgaggcag ttccatagga tggcaagatc ctggtatcgg tctgcgattc   480
cgactcgtcc aacatcaata caacctatta atttccctc gtcaaaaata aggttatcaa   540
gtgagaaatc accatgagtg acgactgaat ccggtgagaa tggcaaaagc ttatgcattt   600
ctttccagac ttgttcaaca ggccagccat tacgctcgtc atcaaaatca ctcgcatcaa   660
ccaaaccgtt attcattcgt gattgcgcct gagcgagacg aaatacgcga tcgctgttaa   720
aaggacaatt acaaacagga atcgaatgca accggcgcag gaacactgcc agcgcatcaa   780
caatattttc acctgaatca ggatattctt ctaatacctg gaatgctgtt ttccggggga   840
tcgcagtggt gagtaaccat gcatcatcag gagtacggat aaaatgcttg atggtcggaa   900
gaggcataaa ttccgtcagc cagtttagtc tgaccatctc atctgtaaca tcattggcaa   960
cgctaccttt gccatgtttc agaaacaact ctggcgcatc gggcttccca tacaatcgat  1020
agattgtcgc acctgattgc ccgacattat cgcgagccca tttataccca tataaatcag  1080
catccatgtt ggaatttaat cgcggcctcg agcaagacgt ttcccgttga atatggctca  1140
taacacccct tgtattactg tttatgtaag cagacagttt tattgttcat gatgatatat  1200
ttttatcttg tgcaatgtaa cagaagttcc tatactttct agagaatagg aacttcggaa  1260
taggcatggt catagctgtt tcc                                           1283

<210> SEQ ID NO 4
<211> LENGTH: 2699
<212> TYPE: DNA
<213> ORGANISM: Escherichia coli

<400> SEQUENCE: 4
gtgaccattg ctattgttat aggcacacat ggttgggctg cagagcagtt gcttaaaacg    60
gcagaaatgc tgttaggcga gcaggaaaac gtcggctgga tcgatttcgt tccaggtgaa   120
aatgccgaaa cgctgattga aaagtacaac gctcagttgg caaaactcga caccactaaa   180
ggcgtgctgt ttctcgttga tacatgggga ggcagcccgt tcaatgctgc agccgcatt   240 gtcgtcgaca aagagcatta tgaagtcatt gcaggcgtta acattccaat gctcgtggaa   300
acgttaatgg cccgtgatga tgacccaagc tttgatgaac tggtggcact ggcagtagaa   360
```

```
acaggccgtg aaggcgtgaa agcactgaaa gccaaaccgg ttgaaaaagc cgcgccagca      420
cccgctgccg cagcaccaaa agcggctcca actccggcaa aaccaatggg gccaaacgac      480
tacatggtta ttggccttgc gcgtatcgac gaccgtctga ttcacggtca ggtcgccacc      540
cgctggacca aagaaaccaa tgtctcccgt attattgttg ttagtgatga agtggctgcg      600
gataccgttc gtaagacact gctcacccag gttgcacctc cgggcgtaac agcacacgta      660
gttgatgttg ccaaaatgat tcgcgtctac aacaacccga aatatgctgg cgaacgcgta      720
atgctgttat ttaccaaccc aacagatgta gagcgtctcg ttgaaggcgg cgtgaaaatc      780
acctctgtta acgtcggtgg tatggcattc cgtcagggta aaacccaggt gaataacgcg      840
gtttcggttg atgaaaaaga tatcgaggcg ttcaagaaac tgaatgcgcg cggtattgag      900
ctggaagtcc gtaaggtttc caccgatccg aaactgaaaa tgatggatct gatcagcaaa      960
atcgataagt aacgtattgt gttgattatc actcagtttt cacacttaag tcttacgtaa     1020
acaggagaag tacaatggag attaccactc ttcaaattgt gctggtattt atcgtagcct     1080
gtatcgcagg tatgggatca atcctcgatg aatttcagtt tcaccgtccg ctaatcgcgt     1140
gtaccctggt gggtatcgtt cttggggata tgaaaaccgg tattattatc ggtggtacgc     1200
tggaaatgat cgcgctgggc tggatgaaca tcggtgctgc agttgcgcct gacgccgctc     1260
tggcttctat catttctacc attctggtta tcgcaggtca tcagagcatt ggtgcaggta     1320
tcgcactggc aatccctctg gccgctgcgg gccaggtact gaccatcatc gttcgtacta     1380
ttaccgttgc tttccagcac gctgcggata aggctgctga taacggcaac ctgacagcga     1440
tttcctggat ccacgtttct tctctgttcc tgcaagcaat gcgtgtggct attccggccg     1500
tcatcgttgc gctgtctgtt ggtaccagcg aagtacagaa catgctgaat gcgattccgg     1560
aagtggtgac caatggtctg aatatcgccg gtggcatgat cgtggtggtt ggttatgcga     1620
tggttatcaa catgatgcgt gctggctacc tgatgccgtt cttctacctc ggcttcgtaa     1680
ccgcagcatt caccaacttt aacctggttg ctctgggtgt gattggtact gttatggcag     1740
tgctctacat ccaacttagc ccgaaataca accgcgtagc cggtgcgcct gctcaggcag     1800
ctggtaacaa cgatctcgat aacgaactgg actaacaggt gagcgaaatg gttgatacaa     1860
ctcaaactac caccgagaaa aaactcactc aaagtgatat tcgtggcgtc ttcctgcgtt     1920
ctaacctctt ccagggttca tggaacttcg aacgtatgca ggcactgggt ttctgcttct     1980
ctatggtacc ggcaattcgt cgcctctacc ctgagaacaa cgaagctcgt aaacaagcta     2040
ttcgccgtca cctggagttc tttaacaccc agccgttcgt ggctgcgccg attctcggcg     2100
taaccctggc gctggaagaa cagcgtgcta atggcgcaga gatcgacgac ggtgctatca     2160
acggtatcaa agtcggtttg atggggccac tggctggtgt aggcgacccg atcttctggg     2220
gaaccgtacg tccggtattt gcagcactgg gtgccggtat cgcgatgagc ggcagcctgt     2280
taggtccgct gctgttcttc atcctgttta acctggtgcg tctggcaacc cgttactacg     2340
gcgtagcgta tggttactcc aaaggtatcg atatcgttaa agatatgggt ggtggcttcc     2400
tgcaaaaact gacggaaggg gcgtctatcc tcggcctgtt tgtcatgggg gcattggtta     2460
acaagtggac acatgtcaac atcccgctgg ttgtctctcg cattactgac cagacgggca     2520
aagaacacgt tactactgtc cagactattc tggaccagtt aatgccaggc ctggtaccac     2580
tgctgctgac ctttgcttgt atgtggctac tgcgcaaaaa agttaacccg ctgtggatca     2640
tcgttggctt cttcgtcatc ggtatcgctg gttacgcttg cggcctgctg ggactgtaa      2699
```

<210> SEQ ID NO 5
<211> LENGTH: 68
<212> TYPE: DNA
<213> ORGANISM: Artificial Sequence
<220> FEATURE:
<223> OTHER INFORMATION: Product of the human mind

<400> SEQUENCE: 5

```
gtgaccattg ctattgttat aggcacacat ggttgggctg cagagcagtt gtaaaacgac    60
ggccagtg                                                             68
```

<210> SEQ ID NO 6
<211> LENGTH: 69
<212> TYPE: DNA
<213> ORGANISM: Artificial Sequence
<220> FEATURE:
<223> OTHER INFORMATION: Product of th human mind.

<400> SEQUENCE: 6

```
ttacagtccc agcaggccgc aagcgtaacc agcgataccg atgacgaaga ggaaacagct    60
atgaccatg                                                            69
```

<210> SEQ ID NO 7
<211> LENGTH: 1030
<212> TYPE: DNA
<213> ORGANISM: Escherichia coli

<400> SEQUENCE: 7

```
cacgctttgg tatgaaaatt gtagggtaca gatgcgttta tttcccctca cccggtaggg    60
gcgagcgagg ggaaacaact cacccgcgct cttgcatcaa ctgctgggcc agcgccttca   120
gttctggcag atattttca tctaccggtc caaacggttt gcggcacagc ggcacagaaa    180
cgacatccat ataatggagg acagttttca ggccgcggaa tacgcccgtt ttgatcagta   240
aatcaatgac tttattgcat tcagtttgca gtttctgcgc ggtctggata tcgccttctt   300
tcagcgcctt aacgatcccc tgatagcgcc agcccatgat gttgtaggta ctgccgatac   360
caccatcagc gcccgccagc agaccagagg cgaagatttc gtcgtaaccg ttatagagca   420
caagatcagg atgttcacga cggatctgct ccatctgata gagatcgcca gaggtctgtt   480
tcagcgcacc tacgccaggc aatgtaacaa gtgtgttgat ctgatccagg gtcagtttta   540
ccccactcag ggctggaatg ttgtacacca ccatcggcaa accatccgcc gaatcaataa   600
ttgcccgata gtgatcgcag tgttcttcaa agctgaaagg atagtagaac ggcgtgacgg   660
cggagacggc atcgaagcca taacgtttag ccgatgccgc aagttgttgg ctttcggcgg   720
tgctgacgca accgacgtgg gcgatgagtt taatcttacc tttcgcctct tcggcgacga   780
tttccagtac ctgttcacgc tcggaaaggc tttgtacaaa ggcctcgccg gtcgaaccac   840
ccacgtataa accgtcgatg ccctgctgaa tattgaactg aaccaggcga cgcagactcg   900
ctttatccag tgcttgttgt tggtcaaaag gagtcaggag tgcagccatt acgccacgta   960
aattcgttgc cataaatacc tctgaagtga tgcttgtctg ataaacgata tacctttata  1020
cctgttatac                                                         1030
```

<210> SEQ ID NO 8
<211> LENGTH: 68
<212> TYPE: DNA
<213> ORGANISM: Artificial Sequence
<220> FEATURE:
<223> OTHER INFORMATION: Product of the human mind.

<400> SEQUENCE: 8
cacgctttgg tatgaaaatt gtagggtaca gatgcgttta tttcccctca gtaaaacgac    60
ggccagtg                                                            68

<210> SEQ ID NO 9
<211> LENGTH: 76
<212> TYPE: DNA
<213> ORGANISM: Artificial Sequence
<220> FEATURE:
<223> OTHER INFORMATION: Product of the human mind.

<400> SEQUENCE: 9
gtataacagg tataaaggta tatcgtttat cagacaagca tcacttcaga ggtatttgga    60
aacagctatg accatg                                                   76

<210> SEQ ID NO 10
<211> LENGTH: 1200
<212> TYPE: DNA
<213> ORGANISM: Escherichia coli

<400> SEQUENCE: 10
tttaaaatcg ggggtcagaa tgtatgcatt aacccagggc cggatcttta ccggccacga    60
atttcttgat gaccacgcgg ttgttatcgc tgatggcctg attaaaagcg tctgtccggt   120
agcggaactg ccgccagaga tcgaacaacg ttcactgaac ggggccattc tctcccccgg   180
ttttatcgat gtgcagttaa acggctgcgg cggcgtacag tttaacgaca ccgctgaagc   240
ggtcagcgtg gaaacgctgg aaatcatgca gaaagccaat gagaaatcag gctgtactaa   300
ctatctgccg acgcttatca ccaccagcga tgagctgatg aaacagggcg tgcgcgttat   360
gcgcgagtac ctggcaaaac atccgaatca ggcgttaggt ctgcatctgg aaggtccgtg   420
gctgaatctg gtaaaaaaag cacccataa tccgaatttt gtgcgtaagc ctgatgccgc   480
gctggtcgat ttcctgtgtg aaaacgccga cgtcattacc aaagtgaccc tggcaccgga   540
aatggttcct gcggaagtca tcagcaaact ggcaaatgcc gggattgtgg tttctgccgg   600
tcactccaac gcgacgttga agaagcaaa agccggtttc cgcgcgggga ttacctttgc   660
cacccatctg tacaacgcga tgccgtatat taccggtcgt gaacctggcc tggcgggcgc   720
gatcctcgac gaagctgaca tttattgcgg tattattgct gatggcctgc atgttgatta   780
cgccaacatt cgcaacgcta acgtctgaa aggcgacaaa ctgtgtctgg ttactgacgc   840
caccgcgcca gcaggtgcca acattgaaca gttcattttt gcgggtaaaa caatatacta   900
ccgtaacgga ctttgtgtgg atgagaacgg tacgttaagc ggttcatcct aaccatgat    960 tgaaggcgtg cgtaatctgg tcgaacattg cggtatcgca ctggatgaag tgctacgtat  1020
ggcgacgctc tatccggcgc gtgcgattgg cgttgagaaa cgtctcggca cactcgccgc  1080
aggtaaagta gccaacctga ctgcattcac acctgattt aaaatcacca agaccatcgt  1140
taacggtaac gaggtcgtaa ctcaataaga gaaagtatga caccaggcgg acaagctcag  1200

<210> SEQ ID NO 11
<211> LENGTH: 68
<212> TYPE: DNA
<213> ORGANISM: Artificial Sequence
<220> FEATURE:
<223> OTHER INFORMATION: Product of the human mind.

<400> SEQUENCE: 11

<210> SEQ ID NO 12
<211> LENGTH: 69
<212> TYPE: DNA
<213> ORGANISM: Artificial Sequence
<220> FEATURE:
<223> OTHER INFORMATION: Product of the human mind.

<400> SEQUENCE: 12

```
ctgagcttgt ccgcctggtg tcatactttc tcttattgag ttacgacctc ggaaacagct    60
atgaccatg                                                            69
```

<210> SEQ ID NO 13
<211> LENGTH: 2350
<212> TYPE: DNA
<213> ORGANISM: Escherichia coli

<400> SEQUENCE: 13

```
cgcatcaggc ataaagcaga ttactttttg atttcataca gcggtgtttg acccgccaca      60
atatggccct gagctttaat gatcaagcca ctgaaatcgt cgatattgct gcaaccaccc     120
gggctaatca tcgagcgggc gttagcgttc aggtaatcca gatccatttc cagaatcggt     180
tgccctgcgc ttacctgcgc accctcttcc accagacgtt taaagccttt accttccagc     240
gctacggtgt cgatacccat atggacgacg atctccgcgc cttttcggt ttccaggcag      300
aacgcgtggt tggtgttgaa gattttcacg attgtccctg cggctggtga tacgacgatt     360
ttatctgtcg gtttcaccgc cacaccgtca cccaccgctt tgctggcgaa tgcttcgtca     420
ggaacctgat ccagtgccac gacatcaccg gtaatcggcg ataccagctc cgcgatagat     480
accgcgtttg gtacagcctg cggttttgct acaggcgcgg cagttgccgg agttgcttca     540
gctgacgcag cggctaccgg accacgggca acgactttct tcatcgcatc gccgatggat     600
tctgctttcg cgccaacaat cacctgaata gtctgtttgt tcagtttcac taccccagaa     660
gcacccagac gttacacat cgtatcgtta acgcgggcag agtcagccac tgtaaggcgc       720
agacgggtga tacaggcgtc aatcgctttc aggttgtcag tgccgccaac cgcagcaata     780
tagttggttg ccagttgagt cagaccttct tcagtgttgc tgttggcttc ttcagtaacg     840
atctcgtctt ctttatcttc acgacccggc gttttcaggt tgaacatgcg gataaccaaa     900
ctgaacacca cgaagtagat agcgaagaag ataacgccca tcaccagcag catccagacg     960
ttctggctgg cggccggcag gttatacatc aacgcgtagt cgatagcccc gcagagaaa    1020
gagaagcccg cgtggatacc cagcagcgtt gccacaaaca ggctgatacc ggtcagcagt    1080
gcgtgcagga ggtacagcag cggagcaagg aacatgaaca ggaattccag cggctcagtc    1140
acaccggtca ggaacgcagt aacagcaaca gaaagcagca taccgccaac catcggacga    1200
cgctctttcg gtgctgcgaa gtacatcgcc agcgccgcac ccggcagacc gaacatcatg    1260
atcgggaaga agccggacat gaacatcccc gcggtgccgt caccggcata aagcggtta    1320
atgtcaccgt ggaaaaccgt acccgccgcg ttggtgaatt caccaatctg gaaccaggcg    1380
atggtgttca gtacctgatg cagaccggtt gggatcagca gacggttgat gaaaccaaag    1440
ataccggaac ccagcgcgcc cgcagaaacg atccactcgc cgcctgcatg gatagcgtgc    1500
tgtaccggcg gccagacgta accaaaaatg gccgccagca ccaggcagaa gaatccggtg    1560
gcaatcggca caaagcgttt gccgccgaag aagctcagga agtccggcag tttaatatcg    1620
```

```
gaccaacggt tataggctgc gccaccaacc agaccggtaa tgatacccgc cagtacaccc    1680
atgttaattt ctgggttgat ggtcaccatc gctttggtta acacaaagta acctaccgca    1740
cccgccagcg ccgccgcacc agcgctgtct ttcgaccagc tggatgccac accgatggcg    1800
aagattaatg cgaggttatc aaaaatcgca ccgcccgcct gggcaataaa cgcaacgtta    1860
agtaaatctg gctgaccgaa tcgcagcaac agtgccgcca ccggcagcac cgcgataggg    1920
agctgtaacg ccctaccgag tcgctggaaa aaacctaaaa tattcatctt attccccta    1980 cgagaaccct atttggctcg tttcaagccg tattttatt ttgctgcaaa ttgtactgcc    2040
gatgttctgt aatcagattg ttagatcatc tgctacagag tgtgtgaaaa tttaattcgt    2100
atcgcaaatt aaacgcgtgt cttttgtgag ttttgtcacc aaatatcgtt attatcactc    2160
ccttttactg gctaaaccag aaaacttatt ttatcattca aaaaatcagg tcggattgac    2220
gcctgtctgc gcaaatccag gttacgctta aagatgccta atccgccaac ggcttacatt    2280
ttacttattg aggtgaataa tgagactgat ccccctgact accgctgaac aggtcggcaa    2340
atgggctgct                                                           2350

<210> SEQ ID NO 14
<211> LENGTH: 68
<212> TYPE: DNA
<213> ORGANISM: Artificial Sequence
<220> FEATURE:
<223> OTHER INFORMATION: Product of the human mind.

<400> SEQUENCE: 14
cgcatcaggc ataaagcaga ttacttttg atttcataca gcggtgtttg gtaaaacgac      60
ggccagtg                                                             68

<210> SEQ ID NO 15
<211> LENGTH: 68
<212> TYPE: DNA
<213> ORGANISM: Artificial Sequence
<220> FEATURE:
<223> OTHER INFORMATION: Product of the human mind.

<400> SEQUENCE: 15
agatgaatat tttaggtttt ttccagcgac tcggtagggc gttacagctg gaaacagcta    60
tgaccatg                                                             68

<210> SEQ ID NO 16
<211> LENGTH: 876
<212> TYPE: DNA
<213> ORGANISM: Escherichia coli

<400> SEQUENCE: 16
atgaccacac tggcgattga tatcggcggt actaaacttg ccgccgcgct gattggcgct    60
gacgggcaga tccgcgatcg tcgtgaactt cctacgccag ccagcagac accgaaagcc    120 ttgcgtgatg ccttatccgc attagtctct ccgttgcaag ctcatgcgca gcgggttgcc    180
atcgcttcga ccgggataat ccgtgacggc agcttgctgg cgcttaatcc gcataatctt    240
ggtggattgc tacactttcc gttagtcaaa acgctgaac aacttaccaa tttgccgacc    300
attgccatta acgacgcgca ggccgcagca tgggcggagt tcaggcgct ggatggcgat    360 ataaccgata tggtctttat caccgttccc accggcgttg gcggcggtgt agtgagcggc    420
tgcaaactgc ttaccggccc tggcggtctg gcggggcata tcgggcatac gcttgccgat    480
```

```
ccacacggcc cagtctgcgg ctgtggacgc acaggttgcg tggaagcgat tgcttctggt    540
cgcggcattg cagcggcagc gcaggggag ttggctggcg cggatgcgaa aactattttc     600
```

```
ccacacggcc cagtctgcgg ctgtggacgc acaggttgcg tggaagcgat tgcttctggt    540
cgcggcattg cagcggcagc gcaggggag ttggctggcg cggatgcgaa aactattttc     600
acgcgcgccg ggcagggtga cgagcaggcg cagcagctga ttcaccgctc cgcacgtacg    660
cttgcaaggc tgatcgctga tattaaagcc acaactgatt gccagtgcgt ggtggtcggt    720
ggcagcgttg gtctggcaga agggtatctg gcgctggtgg aaacgtatct ggcgcaggag    780
ccagcggcat tcatgttga tttactggcg gcgcattacc gccatgatgc aggtttactt     840
ggggctgcgc tgttggccca gggagaaaaa ttatga                              876
```

<210> SEQ ID NO 17
<211> LENGTH: 291
<212> TYPE: PRT
<213> ORGANISM: Escherichia coli

<400> SEQUENCE: 17

```
Met Thr Thr Leu Ala Ile Asp Ile Gly Gly Thr Lys Leu Ala Ala
 1               5                  10                  15

Leu Ile Gly Ala Asp Gly Gln Ile Arg Asp Arg Arg Glu Leu Pro Thr
                20                  25                  30

Pro Ala Ser Gln Thr Pro Glu Ala Leu Arg Asp Ala Leu Ser Ala Leu
            35                  40                  45

Val Ser Pro Leu Gln Ala His Ala Gln Arg Val Ala Ile Ala Ser Thr
        50                  55                  60

Gly Ile Ile Arg Asp Gly Ser Leu Leu Ala Leu Asn Pro His Asn Leu
    65                  70                  75                  80

Gly Gly Leu Leu His Phe Pro Leu Val Lys Thr Leu Glu Gln Leu Thr
                85                  90                  95

Asn Leu Pro Thr Ile Ala Ile Asn Asp Ala Gln Ala Ala Ala Trp Ala
            100                 105                 110

Glu Phe Gln Ala Leu Asp Gly Asp Ile Thr Asp Met Val Phe Ile Thr
        115                 120                 125

Val Ser Thr Gly Val Gly Gly Gly Val Val Ser Gly Cys Lys Leu Leu
    130                 135                 140

Thr Gly Pro Gly Gly Leu Ala Gly His Ile Gly His Thr Leu Ala Asp
145                 150                 155                 160

Pro His Gly Pro Val Cys Gly Cys Gly Arg Thr Gly Cys Val Glu Ala
                165                 170                 175

Ile Ala Ser Gly Arg Gly Ile Ala Ala Ala Gln Gly Glu Leu Ala
        180                 185                 190

Gly Ala Asp Ala Lys Thr Ile Phe Thr Arg Ala Gly Gln Gly Asp Glu
    195                 200                 205

Gln Ala Gln Gln Leu Ile His Arg Ser Ala Arg Thr Leu Ala Arg Leu
210                 215                 220

Ile Ala Asp Ile Lys Ala Thr Thr Asp Cys Gln Cys Val Val Gly
225                 230                 235                 240

Gly Ser Val Gly Leu Ala Glu Gly Tyr Leu Ala Leu Val Glu Thr Tyr
                245                 250                 255

Leu Ala Gln Glu Pro Ala Ala Phe His Val Asp Leu Leu Ala Ala His
            260                 265                 270

Tyr Arg His Asp Ala Gly Leu Leu Gly Ala Ala Leu Leu Ala Gln Gly
        275                 280                 285

Glu Lys Leu
    290
```

<210> SEQ ID NO 18
<211> LENGTH: 30
<212> TYPE: DNA
<213> ORGANISM: Artificial Sequence
<220> FEATURE:
<223> OTHER INFORMATION: Product of the human mind.

<400> SEQUENCE: 18
catgccatgg ctaccacact ggcgattgat                            30

<210> SEQ ID NO 19
<211> LENGTH: 31
<212> TYPE: DNA
<213> ORGANISM: Artificial Sequence
<220> FEATURE:
<223> OTHER INFORMATION: Product of the human mind.

<400> SEQUENCE: 19
cccaagctta ttataatttt tctccctggg c                          31

<210> SEQ ID NO 20
<211> LENGTH: 22
<212> TYPE: DNA
<213> ORGANISM: Artificial Sequence
<220> FEATURE:
<223> OTHER INFORMATION: Product of the human mind.

<400> SEQUENCE: 20
ttcgtgtcgc tcaaggcgca ct                                    22

<210> SEQ ID NO 21
<211> LENGTH: 36
<212> TYPE: DNA
<213> ORGANISM: Artificial Sequence
<220> FEATURE:
<223> OTHER INFORMATION: Product of the human mind.

<400> SEQUENCE: 21
cactggccgt cgttttacgc ttctgcgttc tgattt                     36

<210> SEQ ID NO 22
<211> LENGTH: 36
<212> TYPE: DNA
<213> ORGANISM: Artificial Sequence
<220> FEATURE:
<223> OTHER INFORMATION: Product of the human mind.

<400> SEQUENCE: 22
aaatcagaac gcagaagcgt aaaacgacgg ccagtg                     36

<210> SEQ ID NO 23
<211> LENGTH: 19
<212> TYPE: DNA
<213> ORGANISM: Artificial Sequence
<220> FEATURE:
<223> OTHER INFORMATION: Product of the human mind.

<400> SEQUENCE: 23
ggaaacagct atgaccatg                                        19

<210> SEQ ID NO 24
<211> LENGTH: 72
<212> TYPE: DNA
<213> ORGANISM: Artificial Sequence
<220> FEATURE:
<223> OTHER INFORMATION: Product of the human mind.

-continued

<400> SEQUENCE: 24
cgcatcaggc ataaagcaga ttacttttg atttcataca gcggtgtttg ttcgtgtcgc    60
tcaaggcgca ct                                                      72

<210> SEQ ID NO 25
<211> LENGTH: 68
<212> TYPE: DNA
<213> ORGANISM: Artificial Sequence
<220> FEATURE:
<223> OTHER INFORMATION: Product of the human mind.

<400> SEQUENCE: 25
agatgaatat tttaggtttt ttccagcgac tcggtagggc gttacagctg gaaacagcta    60
tgaccatg                                                            68

<210> SEQ ID NO 26
<211> LENGTH: 876
<212> TYPE: DNA
<213> ORGANISM: Escherichia coli

<400> SEQUENCE: 26
atgaccacac tggcgattga tatcggcggt actaaacttg ccgccgcgct gattggcgct    60
gacgggcaga tccgcgatcg tcgtgaactt cctacgccag ccagccggac accagaagcc   120
ttgcgtgatg ccttatccgc attagtctct ccgttgcaag ctcatgcgca gcgggttgcc   180
atcgcttcga ccgggataat ccgtgacggc agcttgctgg cgcttaatcc gcataatctt   240
ggtggattgc tacactttcc gttagtcaaa acgctggaac aacttaccaa tttgccgacc   300
attgccatga cgacgcgca ggccgcagca tgggcgagt tcaggcgct ggatggcgat     360 ataaccgata tggtctttat caccgttcc accggcgttg gcggcggtgt agtgagcggc   420
tgcaaactgc ttaccggccc tggcggtctg gcggggcata tcgggcatac gcttgccgat   480
ccacacggcc cagtctgcgg ctgtggacgc acaggttgcg tggaagcgat tgcttctggt   540
cgcggcattg cagcggcagc gcaggggag ttggctggcg cggatgcgaa aactattttc    600
acgcgcgccg gcagggtga cgagcaggcg cagcagctga ttcaccgctc cgcacgtacg   660
cttgcaagcc tgatcgctga tattaaagcc acaactgatt gccagtgcgt ggtggtcggt   720
ggcagcgttg gtctggcaga agggtatctg cgctggtgg aaacgtatct ggcgcaggag    780
ccggcggcat ttcatgttga tttactggcg gcgcattacc gccatgatgc aggtttactt   840
ggggctgcgc tgttggccca gggagaaaaa ttatga                            876

<210> SEQ ID NO 27
<211> LENGTH: 291
<212> TYPE: PRT
<213> ORGANISM: Escherichia coli

<400> SEQUENCE: 27

Met Thr Thr Leu Ala Ile Asp Ile Gly Gly Thr Lys Leu Ala Ala Ala
1               5                   10                  15

Leu Ile Gly Ala Asp Gly Gln Ile Arg Asp Arg Arg Glu Leu Pro Thr
            20                  25                  30

Pro Ala Ser Arg Thr Pro Glu Ala Leu Arg Asp Ala Leu Ser Ala Leu
        35                  40                  45

Val Ser Pro Leu Gln Ala His Ala Gln Arg Val Ala Ile Ala Ser Thr
    50                  55                  60

```
Gly Ile Ile Arg Asp Gly Ser Leu Leu Ala Leu Asn Pro His Asn Leu
 65                  70                  75                  80

Gly Gly Leu Leu His Phe Pro Leu Val Lys Thr Leu Glu Gln Leu Thr
                 85                  90                  95

Asn Leu Pro Thr Ile Ala Met Asn Asp Ala Gln Ala Ala Ala Trp Ala
            100                 105                 110

Glu Phe Gln Ala Leu Asp Gly Asp Ile Thr Asp Met Val Phe Ile Thr
        115                 120                 125

Val Ser Thr Gly Val Gly Gly Val Val Ser Gly Cys Lys Leu Leu
    130                 135                 140

Thr Gly Pro Gly Gly Leu Ala Gly His Ile Gly His Thr Leu Ala Asp
145                 150                 155                 160

Pro His Gly Pro Val Cys Gly Cys Gly Arg Thr Gly Cys Val Glu Ala
                165                 170                 175

Ile Ala Ser Gly Arg Gly Ile Ala Ala Ala Gln Gly Glu Leu Ala
                180                 185                 190

Gly Ala Asp Ala Lys Thr Ile Phe Thr Arg Ala Gly Gln Gly Asp Glu
        195                 200                 205

Gln Ala Gln Gln Leu Ile His Arg Ser Ala Arg Thr Leu Ala Ser Leu
    210                 215                 220

Ile Ala Asp Ile Lys Ala Thr Thr Asp Cys Gln Cys Val Val Val Gly
225                 230                 235                 240

Gly Ser Val Gly Leu Ala Glu Gly Tyr Leu Ala Leu Val Glu Thr Tyr
                245                 250                 255

Leu Ala Gln Glu Pro Ala Ala Phe His Val Asp Leu Ala Ala His
        260                 265                 270

Tyr Arg His Asp Ala Gly Leu Leu Gly Ala Ala Leu Leu Ala Gln Gly
        275                 280                 285

Glu Lys Leu
        290

<210> SEQ ID NO 28
<211> LENGTH: 690
<212> TYPE: DNA
<213> ORGANISM: Escherichia coli

<400> SEQUENCE: 28
atgtcgttac ttgcacaact ggatcaaaaa atcgctgcta acggtggcct gattgtctcc      60
tgccagccgg ttccggacag cccgctcgat aaacccgaaa tcgtcgccgc catggcatta     120
gcggcagaac aggcgggcgc ggttgccatt cgcattgaag gtgtggcaaa tctgcaagcc     180
acgcgtgcgg tggtgagcgt gccgattatt ggaattgtga acgcgatctg gaggattct     240 ccggtacgca tcacggccta tattgaagat gttgatgcgc tggcgcaggc gggcgcggac     300
attatcgcca ttgacggcac cgaccgcccg cgtccggtgc ctgttgaaac gctgctggca     360
cgtattcacc atcacggttt actggcgatg accgactgct caacgccgga agacggcctg     420
gcatgccaaa agctgggagc cgaaattatt ggcactacgc tttctggcta taccacgcct     480
gaaacgccag aagagccgga tctggcgctg tgtgaaacgt tgagcgacgc cggatgtcgg     540
gtgattgccg aagggcgtta caacacgcct gctcaggcgg cggatgcgat gccacggc     600 gcgtgggcgg tgacggtcgg ttctgcaatc acgcgtcttg agcacatttg tcagtggtac     660
aacacagcga tgaaaaaggc ggtgctatga                                      690

<210> SEQ ID NO 29
```

<211> LENGTH: 229
<212> TYPE: PRT
<213> ORGANISM: Escherichia coli

<400> SEQUENCE: 29

Met Ser Leu Leu Ala Gln Leu Asp Gln Lys Ile Ala Ala Asn Gly Gly
1               5                   10                  15
Leu Ile Val Ser Cys Gln Pro Val Pro Asp Ser Pro Leu Asp Lys Pro
                20                  25                  30
Glu Ile Val Ala Ala Met Ala Leu Ala Ala Glu Gln Ala Gly Ala Val
            35                  40                  45
Ala Ile Arg Ile Glu Gly Val Ala Asn Leu Gln Ala Thr Arg Ala Val
    50                  55                  60
Val Ser Val Pro Ile Ile Gly Ile Val Lys Arg Asp Leu Glu Asp Ser
65                  70                  75                  80
Pro Val Arg Ile Thr Ala Tyr Ile Glu Asp Val Asp Ala Leu Ala Gln
                85                  90                  95
Ala Gly Ala Asp Ile Ile Ala Ile Asp Gly Thr Asp Arg Pro Arg Pro
            100                 105                 110
Val Pro Val Glu Thr Leu Leu Ala Arg Ile His His His Gly Leu Leu
        115                 120                 125
Ala Met Thr Asp Cys Ser Thr Pro Glu Asp Gly Leu Ala Cys Gln Lys
    130                 135                 140
Leu Gly Ala Glu Ile Ile Gly Thr Thr Leu Ser Gly Tyr Thr Thr Pro
145                 150                 155                 160
Glu Thr Pro Glu Glu Pro Asp Leu Ala Leu Val Lys Thr Leu Ser Asp
                165                 170                 175
Ala Gly Cys Arg Val Ile Ala Glu Gly Arg Tyr Asn Thr Pro Ala Gln
            180                 185                 190
Ala Ala Asp Ala Met Arg His Gly Ala Trp Ala Val Thr Val Gly Ser
        195                 200                 205
Ala Ile Thr Arg Leu Glu His Ile Cys Gln Trp Tyr Asn Thr Ala Met
    210                 215                 220
Lys Lys Ala Val Leu
225

<210> SEQ ID NO 30
<211> LENGTH: 29
<212> TYPE: DNA
<213> ORGANISM: Artificial Sequence
<220> FEATURE:
<223> OTHER INFORMATION: Product of the human mind.

<400> SEQUENCE: 30
catgccatgg cttcgttact tgcacaact                                29

<210> SEQ ID NO 31
<211> LENGTH: 34
<212> TYPE: DNA
<213> ORGANISM: Artificial Sequence
<220> FEATURE:
<223> OTHER INFORMATION: Product of the human mind.

<400> SEQUENCE: 31
cccaagctta tcatagcacc gccttttca tcgc                           34

<210> SEQ ID NO 32
<211> LENGTH: 166
<212> TYPE: DNA

<213> ORGANISM: Artificial Sequence
<220> FEATURE:
<223> OTHER INFORMATION: Product of the human mind.

<400> SEQUENCE: 32

```
ttcgtgtcgc tcaaggcgca ctcccgttct ggataatgtt ttttgcgccg acatcataac      60
ggttctggca aatattctga aatgagctgt tgacaattaa tcatccggct cgtataatgt     120
gtggaattgt gagcggataa caatttcaca caggaaacag accatg                    166
```

<210> SEQ ID NO 33
<211> LENGTH: 41
<212> TYPE: DNA
<213> ORGANISM: Artificial Sequence
<220> FEATURE:
<223> OTHER INFORMATION: Product of the human mind.

<400> SEQUENCE: 33

```
catggtcata gctgtttcct tcgtgtcgct caaggcgcac t                          41
```

<210> SEQ ID NO 34
<211> LENGTH: 19
<212> TYPE: DNA
<213> ORGANISM: Artificial Sequence
<220> FEATURE:
<223> OTHER INFORMATION: Product of the human mind.

<400> SEQUENCE: 34

```
catggtctgt ttcctgtgt                                                   19
```

<210> SEQ ID NO 35
<211> LENGTH: 41
<212> TYPE: DNA
<213> ORGANISM: Artificial Sequence
<220> FEATURE:
<223> OTHER INFORMATION: Product of the human mind.

<400> SEQUENCE: 35

```
agtgcgcctt gagcgacacg aaggaaacag ctatgaccat g                          41
```

<210> SEQ ID NO 36
<211> LENGTH: 18
<212> TYPE: DNA
<213> ORGANISM: Artificial Sequence
<220> FEATURE:
<223> OTHER INFORMATION: Product of the human mind.

<400> SEQUENCE: 36

```
gtaaaacgac ggccagtg                                                    18
```

<210> SEQ ID NO 37
<211> LENGTH: 47
<212> TYPE: DNA
<213> ORGANISM: Escherichia coli

<400> SEQUENCE: 37

```
acatcttccc ttagcgaaag gcccggtaca tagaccgggc aacagga                    47
```

<210> SEQ ID NO 38
<211> LENGTH: 68
<212> TYPE: DNA
<213> ORGANISM: Artificial Sequence
<220> FEATURE:
<223> OTHER INFORMATION: Product of the human mind.

<400> SEQUENCE: 38

```
ccgtgccgtt tggcagcgcc aaaaacgatt tagtcaaaac caaaagttaa gtaaaacgac    60
ggccagtg                                                              68

<210> SEQ ID NO 39
<211> LENGTH: 69
<212> TYPE: DNA
<213> ORGANISM: Artificial Sequence
<220> FEATURE:
<223> OTHER INFORMATION: Product of the human mind.

<400> SEQUENCE: 39
atcaggccac cgttagcagc gattttttga tccagttgtg caagtaacga catggtctgt    60
ttcctgtgt                                                             69

<210> SEQ ID NO 40
<211> LENGTH: 69
<212> TYPE: DNA
<213> ORGANISM: Artificial Sequence
<220> FEATURE:
<223> OTHER INFORMATION: Product of the human mind.

<400> SEQUENCE: 40
cttattcccc ctacgagaac cctatttggc tcgtttcaag ccgtattttt agtaaaacga    60
cggccagtg                                                             69

<210> SEQ ID NO 41
<211> LENGTH: 67
<212> TYPE: DNA
<213> ORGANISM: Artificial Sequence
<220> FEATURE:
<223> OTHER INFORMATION: Product of the human mind.

<400> SEQUENCE: 41
agcagcccat ttgccgacct gttcagcggt agtcaggggg atcagtctca tggtctgttt    60
cctgtgt                                                               67

<210> SEQ ID NO 42
<211> LENGTH: 190
<212> TYPE: DNA
<213> ORGANISM: Escherichia coli

<400> SEQUENCE: 42
tgaggagata acataatctc cctcccacaa gcagtaacta taaaaataac cccactctct    60
acaaggctcg gggcgcccga aaaaacgggc atacaggttg accgacaacg atataaatcg   120
gaatcaaaaa ctatgtgtgg aattgttggc gcgatcgcgc aacgtgatgt agcagaaatc   180
cttcttgaag                                                           190

<210> SEQ ID NO 43
<211> LENGTH: 71
<212> TYPE: DNA
<213> ORGANISM: Artificial Sequence
<220> FEATURE:
<223> OTHER INFORMATION: Product of the human mind.

<400> SEQUENCE: 43
tgaggagata acataatctc cctcccacaa gcagtaacta taaaaataac cccgtaaaac    60
gacggccagt g                                                         71

<210> SEQ ID NO 44
```

```
<211> LENGTH: 75
<212> TYPE: DNA
<213> ORGANISM: Artificial Sequence
<220> FEATURE:
<223> OTHER INFORMATION: Product of the human mind.

<400> SEQUENCE: 44
cttcaagaag gatttctgct acatcacgtt gcgcgatcgc gccaacaatt ccacacggaa    60
acagctatga ccatg                                                    75

<210> SEQ ID NO 45
<211> LENGTH: 68
<212> TYPE: DNA
<213> ORGANISM: Artificial Sequence
<220> FEATURE:
<223> OTHER INFORMATION: Product of the human mind.

<400> SEQUENCE: 45
tgaggagata acataatctc cctcccacaa gcagtaacta taaaaataac gtaaaacgac    60
ggccagtg                                                            68

<210> SEQ ID NO 46
<211> LENGTH: 74
<212> TYPE: DNA
<213> ORGANISM: Artificial Sequence
<220> FEATURE:
<223> OTHER INFORMATION: Product of the human mind.

<400> SEQUENCE: 46
cttcaagaag gatttctgct acatcacgtt gcgcgatcgc gccaacaatt ccacacatgg    60
tctgtttcct gtgt                                                     74

<210> SEQ ID NO 47
<211> LENGTH: 69
<212> TYPE: DNA
<213> ORGANISM: Artificial Sequence
<220> FEATURE:
<223> OTHER INFORMATION: Product of the human mind.

<400> SEQUENCE: 47
cttattcccc ctacgagaac cctatttggc tcgtttcaag ccgtattttt agtaaaacga    60
cggccagtg                                                           69

<210> SEQ ID NO 48
<211> LENGTH: 70
<212> TYPE: DNA
<213> ORGANISM: Artificial Sequence
<220> FEATURE:
<223> OTHER INFORMATION: Product of the human mind.

<400> SEQUENCE: 48
agcagcccat ttgccgacct gttcagcggt agtcaggggg atcagtctca tggaaacagc    60
tatgaccatg                                                          70

<210> SEQ ID NO 49
<211> LENGTH: 1131
<212> TYPE: DNA
<213> ORGANISM: Escherichia coli

<400> SEQUENCE: 49
gtgaaagtac tgactgtatt tggtacgcgc ccggaagcca tcaagatggc gccgttggtg    60
catgcgttgg caaagatcc ttttttttgag gctaaagttt gcgtcactgc gcagcatcgg   120
```

-continued

```
gagatgctcg atcaggtgct gaaactcttt tccattgtac ctgactacga tctcaacata    180
atgcagccag gacagggcct gacagagata acctgtcgga ttctggaagg gctaaaacct    240
attcttgccg agttcaaacc agacgtcgtg ctggttcacg gcgatacgac gacgacgctg    300
gcaaccagcc tggcggcgtt ttatcagcgt attcctgttg gtcacgttga ggctggtctg    360
cgcacgggcg atctctattc gccgtggccg gaagaggcta accgtacatt gaccgggcat    420
ctggcgatgt atcacttctc tccaaccgaa acttcccggc aaaacttgct gcgtgaaaac    480
gttgcggata gccgaatctt cattaccggt aatacagtca ttgatgcact gttatgggtg    540
cgtgaccagg tgatgagcag cgacaagctg cgttcagaac tggcggcaaa ttacccgttt    600
atcgaccccg ataaaaagat gattctggtg accggtcaca gcgtgagag tttcggtcgt     660
ggctttgaag aaatctgcca cgcgctggca gacatcgcca ccacgcacca ggacatccag    720
attgtctatc cggtgcatct caacccgaac gtcagagaac cggtcaatcg cattctgggg    780
catgtgaaaa atgtcattct gatcgatccc caggagtatt taccgtttgt ctggctgatg    840
aaccacgcct ggctgatttt gaccgactca ggcggcattc aggaagaagc gccttcgctg    900
gggaaacctg tgctggtgat gcgcgatacc actgagcgtc cggaagcggt gacggcgggt    960
acggtgcgtc tggtaggcac ggataagcag cgaattgtcg aggaagtgac gcgtctttta   1020
aaagacgaaa acgaatatca agctatgagc cgcgcccata acccgtatgg tgatggtcag   1080
gcatgctctc gcattctgga agcgttaaaa aataatcgga tatcactatg a             1131
```

<210> SEQ ID NO 50
<211> LENGTH: 376
<212> TYPE: PRT
<213> ORGANISM: Escherichia coli

<400> SEQUENCE: 50

```
Met Lys Val Leu Thr Val Phe Gly Thr Arg Pro Glu Ala Ile Lys Met
1               5                   10                  15

Ala Pro Leu Val His Ala Leu Ala Lys Asp Pro Phe Phe Glu Ala Lys
                20                  25                  30

Val Cys Val Thr Ala Gln His Arg Glu Met Leu Asp Gln Val Leu Lys
            35                  40                  45

Leu Phe Ser Ile Val Pro Asp Tyr Asp Leu Asn Ile Met Gln Pro Gly
        50                  55                  60

Gln Gly Leu Thr Glu Ile Thr Cys Arg Ile Leu Glu Gly Leu Lys Pro
65                  70                  75                  80

Ile Leu Ala Glu Phe Lys Pro Asp Val Val Leu Val His Gly Asp Thr
                85                  90                  95

Thr Thr Thr Leu Ala Thr Ser Leu Ala Ala Phe Tyr Gln Arg Ile Pro
            100                 105                 110

Val Gly His Val Glu Ala Gly Leu Arg Thr Gly Asp Leu Tyr Ser Pro
        115                 120                 125

Trp Pro Glu Glu Ala Asn Arg Thr Leu Thr Gly His Leu Ala Met Tyr
130                 135                 140

His Phe Ser Pro Thr Glu Thr Ser Arg Gln Asn Leu Leu Arg Glu Asn
145                 150                 155                 160

Val Ala Asp Ser Arg Ile Phe Ile Thr Gly Asn Thr Val Ile Asp Ala
                165                 170                 175

Leu Leu Trp Val Arg Asp Gln Val Met Ser Ser Asp Lys Leu Arg Ser
            180                 185                 190
```

```
Glu Leu Ala Ala Asn Tyr Pro Phe Ile Asp Pro Asp Lys Lys Met Ile
            195                 200                 205

Leu Val Thr Gly His Arg Arg Glu Ser Phe Gly Arg Gly Phe Glu Glu
    210                 215                 220

Ile Cys His Ala Leu Ala Asp Ile Ala Thr Thr His Gln Asp Ile Gln
225                 230                 235                 240

Ile Val Tyr Pro Val His Leu Asn Pro Asn Val Arg Glu Pro Val Asn
                245                 250                 255

Arg Ile Leu Gly His Val Lys Asn Val Ile Leu Ile Asp Pro Gln Glu
            260                 265                 270

Tyr Leu Pro Phe Val Trp Leu Met Asn His Ala Trp Leu Ile Leu Thr
        275                 280                 285

Asp Ser Gly Gly Ile Gln Glu Glu Ala Pro Ser Leu Gly Lys Pro Val
    290                 295                 300

Leu Val Met Arg Asp Thr Thr Glu Arg Pro Glu Ala Val Thr Ala Gly
305                 310                 315                 320

Thr Val Arg Leu Val Gly Thr Asp Lys Gln Arg Ile Val Glu Glu Val
                325                 330                 335

Thr Arg Leu Leu Lys Asp Glu Asn Glu Tyr Gln Ala Met Ser Arg Ala
            340                 345                 350

His Asn Pro Tyr Gly Asp Gly Gln Ala Cys Ser Arg Ile Leu Glu Ala
        355                 360                 365

Leu Lys Asn Asn Arg Ile Ser Leu
    370                 375

<210> SEQ ID NO 51
<211> LENGTH: 30
<212> TYPE: DNA
<213> ORGANISM: Artificial Sequence
<220> FEATURE:
<223> OTHER INFORMATION: Product of the human mind.

<400> SEQUENCE: 51
catgccatgg tgaaagtact gactgtattt                                    30

<210> SEQ ID NO 52
<211> LENGTH: 31
<212> TYPE: DNA
<213> ORGANISM: Artificial Sequence
<220> FEATURE:
<223> OTHER INFORMATION: Product of the human mind.

<400> SEQUENCE: 52
cccaagctta ttatagtgat atccgattat t                                  31

<210> SEQ ID NO 53
<211> LENGTH: 110
<212> TYPE: DNA
<213> ORGANISM: Escherichia coli

<400> SEQUENCE: 53
tgtcgggggg ctgatcgggg ctggtgtcgc attaacccgc cgttgctcga aatagcaaca   60
ctgctgcggt gagcgcaaag gcgctcgccg cttattcgaa gagaatcgat              110

<210> SEQ ID NO 54
<211> LENGTH: 73
<212> TYPE: DNA
<213> ORGANISM: Artificial Sequence
<220> FEATURE:
<223> OTHER INFORMATION: Product of the human mind.
```

<400> SEQUENCE: 54

```
tgtcgggggg ctgatcgggg ctggtgtcgc attaacccgc cgttgctcga ataggtaaa    60
acgacggcca gtg                                                      73
```

<210> SEQ ID NO 55
<211> LENGTH: 69
<212> TYPE: DNA
<213> ORGANISM: Artificial Sequence
<220> FEATURE:
<223> OTHER INFORMATION: Product of the human mind.

<400> SEQUENCE: 55

```
atcgattctc ttcgaataag cggcgagcgc ctttgcgctc accgcagcag catggtctgt    60
ttcctgtgt                                                            69
```

<210> SEQ ID NO 56
<211> LENGTH: 690
<212> TYPE: DNA
<213> ORGANISM: Escherichia coli

<400> SEQUENCE: 56

```
atgtcgttac ttgcacaact ggatcaaaaa atcgctgcta acggtggcct gattgtctcc    60
tgccagccgg ttccggacag cccgctcgat aaacccgaaa tcgtcgccgc catggcatta   120
gcggcagaac aggcgggcgc ggttgccatt cgcattgaag gtgtggcaaa tctgcaagcc   180
acgcgtgcgg tggtgagtgt gccgattatt ggaattgtga acgcgatct ggaggattct   240
ccggtacgca tcacggccta tattgaagat gttgatgcgc tggcgcaggc gggcgcggac   300
attatcgcca ttgacggcac cgaccgcccg cgtccggtgc ctgttgaaac gctgctggca   360
cgtattcacc atcacggttt actggcgatg accgaccgct caacgccgga agacggcctg   420
gcatgccaaa agctgggagc cgaaattatt ggcactacgc tttctggcta taccacgcct   480
gaaacgccag aagagccgga tctggcgctg gtgaaaacgt tgagcgacgc cggatgtcgg   540
gtgattgccg aagggcgtca caacacgcct gctcaggcgg cggatgcgat cgccacggc   600
gcgtgggcgg tgacggtcgg ttctgcaatc acgcgtcttg agcacatttg tcagtggtac   660
aacacagcga tgaaaaaggc ggtgctatga                                    690
```

<210> SEQ ID NO 57
<211> LENGTH: 229
<212> TYPE: PRT
<213> ORGANISM: Escherichia coli

<400> SEQUENCE: 57

```
Met Ser Leu Leu Ala Gln Leu Asp Gln Lys Ile Ala Ala Asn Gly Gly
1               5                   10                  15

Leu Ile Val Ser Cys Gln Pro Val Pro Asp Ser Pro Leu Asp Lys Pro
            20                  25                  30

Glu Ile Val Ala Ala Met Ala Leu Ala Ala Glu Gln Ala Gly Ala Val
        35                  40                  45

Ala Ile Arg Ile Glu Gly Val Ala Asn Leu Gln Ala Thr Arg Ala Val
    50                  55                  60

Val Ser Val Pro Ile Ile Gly Ile Val Lys Arg Asp Leu Glu Asp Ser
65                  70                  75                  80

Pro Val Arg Ile Thr Ala Tyr Ile Glu Asp Val Asp Ala Leu Ala Gln
                85                  90                  95
```

Ala Gly Ala Asp Ile Ile Ala Ile Asp Gly Thr Asp Arg Pro Arg Pro
            100                 105                 110

Val Pro Val Glu Thr Leu Leu Ala Arg Ile His His Gly Leu Leu
        115                 120                 125

Ala Met Thr Asp Arg Ser Thr Pro Glu Asp Gly Leu Ala Cys Gln Lys
    130                 135                 140

Leu Gly Ala Glu Ile Ile Gly Thr Thr Leu Ser Gly Tyr Thr Thr Pro
145                 150                 155                 160

Glu Thr Pro Glu Glu Pro Asp Leu Ala Leu Val Lys Thr Leu Ser Asp
                165                 170                 175

Ala Gly Cys Arg Val Ile Ala Glu Gly Arg His Asn Thr Pro Ala Gln
            180                 185                 190

Ala Ala Asp Ala Met Arg His Gly Ala Trp Ala Val Thr Val Gly Ser
        195                 200                 205

Ala Ile Thr Arg Leu Glu His Ile Cys Gln Trp Tyr Asn Thr Ala Met
    210                 215                 220

Lys Lys Ala Val Leu
225

<210> SEQ ID NO 58
<211> LENGTH: 1131
<212> TYPE: DNA
<213> ORGANISM: Escherichia coli

<400> SEQUENCE: 58

| | | |
|---|---|---|
| gtgaaagtac tgactgtatt tggtacgcgc ccggaagcca tcaagatggc gccgttggtg | 60 |
| catgcgttgg caaaagatcc tttttttgag gctaaagttt ccgtcactgc gcagcatcgg | 120 |
| gagatgctcg atcaggtgct gaaactcttt tccattgtac ctgactacga tctcaacata | 180 |
| atgcagccag acagggcct gacagagata acctgtcgga ttctggaagg ctaaaaacct | 240 |
| attcttgccg agttcaaacc agacgtcgtg ctggttcacg gcgatacgac gacgacgctg | 300 |
| gcaaccagcc tggcggcgtt tatcagcgt attcctgttg gtcacgttga ggctggtctg | 360 |
| cgcacgggcg atctctattc gccgtggccg aagaggcta accgtacatt gaccgggcat | 420 |
| ctggcgatgt atgacttctc tccaaccgaa acttcccggc aaaacttgct gcgtgaaaac | 480 |
| gttgcggata cccgaatctt cattaccggt aatacagtca ttgatgcact gttatgggtg | 540 |
| cgtgaccagg tgatgagcag cgacaagctg cgttcagaac tggcggcaaa ttacccgttt | 600 |
| atcgaccccg ataaaaagat gattctggtg accggtcaca ggcgtgagag tttcggtcgt | 660 |
| ggctttgaag aaatcttcca cgcgctggca gacatcgcca ccacgcacca ggacatccag | 720 |
| attgtctatc cggggcatct caaccgaac gtcagagaac cggtcaatcg cattctgggg | 780 |
| catgtgaaaa atgtcattct gatcgatccc caggagtatt accgtttgt ctggctgatg | 840 |
| aaccacgcct ggctgatttt gaccgactca ggcggcattc aggaagaagc gccttcgctg | 900 |
| gggaaacctg tgctggtgat gcgcgatacc actgagcgtc cggaagcggt gacggcgggt | 960 |
| acggtgcgtc tggtaggcac ggataagcag cgaattgtcg aggaagtgac gcgtctttta | 1020 |
| aaagacgaaa acgaatacca agctatgagc cgcgcccata acccgtatgg tgatggtcag | 1080 |
| gcatgctctc gcattctgga agcgttaaaa ataatcgga tatcactatg a | 1131 |

<210> SEQ ID NO 59
<211> LENGTH: 376
<212> TYPE: PRT
<213> ORGANISM: Escherichia coli

```
<400> SEQUENCE: 59

Met Lys Val Leu Thr Val Phe Gly Thr Arg Pro Glu Ala Ile Lys Met
1               5                   10                  15

Ala Pro Leu Val His Ala Leu Ala Lys Asp Pro Phe Phe Glu Ala Lys
            20                  25                  30

Val Ser Val Thr Ala Gln His Arg Glu Met Leu Asp Gln Val Leu Lys
        35                  40                  45

Leu Phe Ser Ile Val Pro Asp Tyr Asp Leu Asn Ile Met Gln Pro Gly
    50                  55                  60

Gln Gly Leu Thr Glu Ile Thr Cys Arg Ile Leu Glu Gly Leu Lys Pro
65                  70                  75                  80

Ile Leu Ala Glu Phe Lys Pro Asp Val Val Leu Val His Gly Asp Thr
                85                  90                  95

Thr Thr Thr Leu Ala Thr Ser Leu Ala Ala Phe Tyr Gln Arg Ile Pro
            100                 105                 110

Val Gly His Val Glu Ala Gly Leu Arg Thr Gly Asp Leu Tyr Ser Pro
        115                 120                 125

Trp Pro Glu Glu Ala Asn Arg Thr Leu Thr Gly His Leu Ala Met Tyr
    130                 135                 140

Asp Phe Ser Pro Thr Glu Thr Ser Arg Gln Asn Leu Leu Arg Glu Asn
145                 150                 155                 160

Val Ala Asp Ser Arg Ile Phe Ile Thr Gly Asn Thr Val Ile Asp Ala
                165                 170                 175

Leu Leu Trp Val Arg Asp Gln Val Met Ser Ser Asp Lys Leu Arg Ser
            180                 185                 190

Glu Leu Ala Ala Asn Tyr Pro Phe Ile Asp Pro Asp Lys Lys Met Ile
        195                 200                 205

Leu Val Thr Gly His Arg Arg Glu Ser Phe Gly Arg Gly Phe Glu Glu
    210                 215                 220

Ile Phe His Ala Leu Ala Asp Ile Ala Thr Thr His Gln Asp Ile Gln
225                 230                 235                 240

Ile Val Tyr Pro Gly His Leu Asn Pro Asn Val Arg Glu Pro Val Asn
                245                 250                 255

Arg Ile Leu Gly His Val Lys Asn Val Ile Leu Ile Asp Pro Gln Glu
            260                 265                 270

Tyr Leu Pro Phe Val Trp Leu Met Asn His Ala Trp Leu Ile Leu Thr
        275                 280                 285

Asp Ser Gly Gly Ile Gln Glu Glu Ala Pro Ser Leu Gly Lys Pro Val
    290                 295                 300

Leu Val Met Arg Asp Thr Thr Glu Arg Pro Glu Ala Val Thr Ala Gly
305                 310                 315                 320

Thr Val Arg Leu Val Gly Thr Asp Lys Gln Arg Ile Val Glu Glu Val
                325                 330                 335

Thr Arg Leu Leu Lys Asp Glu Asn Glu Tyr Gln Ala Met Ser Arg Ala
            340                 345                 350

His Asn Pro Tyr Gly Asp Gly Gln Ala Cys Ser Arg Ile Leu Glu Ala
        355                 360                 365

Leu Lys Asn Asn Arg Ile Ser Leu
    370                 375
```